United States Patent
Slobitker et al.

(10) Patent No.: US 9,826,985 B2
(45) Date of Patent: Nov. 28, 2017

(54) FLEXIBLE BONE TOOL

(71) Applicant: T.A.G. Medical Devices—Agriculture Cooperative Ltd., Kibbutz Gaaton (IL)

(72) Inventors: Leon Slobitker, Carmiel (IL); Ran Weisman, Kfar-Vradim (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 0 days.

(21) Appl. No.: 15/115,678

(22) PCT Filed: Feb. 17, 2015

(86) PCT No.: PCT/IL2015/050178
§ 371 (c)(1),
(2) Date: Jul. 31, 2016

(87) PCT Pub. No.: WO2015/121869
PCT Pub. Date: Aug. 20, 2015

(65) Prior Publication Data
US 2016/0345986 A1    Dec. 1, 2016

Related U.S. Application Data

(60) Provisional application No. 61/940,609, filed on Feb. 17, 2014.

(51) Int. Cl.
*A61B 17/00* (2006.01)
*A61B 17/16* (2006.01)
(Continued)

(52) U.S. Cl.
CPC ...... *A61B 17/1631* (2013.01); *A61B 17/1615* (2013.01); *A61B 17/1642* (2013.01);
(Continued)

(58) Field of Classification Search
None
See application file for complete search history.

(56) References Cited

U.S. PATENT DOCUMENTS 3,060,972 A    10/1962   Sheldon
3,430,662 A    3/1969    Guarnaschelli
(Continued)

FOREIGN PATENT DOCUMENTS

WO    WO 2015/121869    8/2015
WO    WO 2017/122215    7/2017

OTHER PUBLICATIONS

International Preliminary Report on Patentability dated Sep. 1, 2016 From the International Bureau of WIPO Re. Application No. PCT/IL2015/050178.
(Continued)

*Primary Examiner* — Sameh Boles

(57) ABSTRACT

A flexible bone tool comprising a bone tissue removal element configured at a distal end of the tool, at least two links coupled proximally to the bone tissue removal element, the links connected to each other by a radial interference connection in which at least one radially outwards extending protrusion of a first link is received within a recess of a subsequent link. In some embodiments, the links are interconnected by a "snap-fit" connection. In some embodiments, the flexible bone tool is configured for transferring torque at a magnitude sufficient for drilling and/or reaming a bore in a bone.

19 Claims, 99 Drawing Sheets

(51) Int. Cl.
    *A61B 17/17*    (2006.01)
    *A61M 25/09*    (2006.01)
(52) U.S. Cl.
    CPC .......... *A61B 17/1675* (2013.01); *A61B 17/17* (2013.01); *A61M 25/09* (2013.01)

(56)         References Cited

U.S. PATENT DOCUMENTS

| | | |
|---|---|---|
| 4,108,211 A | 8/1978 | Tanaka |
| 4,328,839 A | 5/1982 | Lyons et al. |
| 4,362,520 A | 12/1982 | Perry |
| 4,600,037 A | 7/1986 | Hatten |
| 4,706,659 A | 11/1987 | Matthews et al. |
| 5,330,480 A | 7/1994 | Meloul et al. |
| 5,499,984 A | 3/1996 | Steiner et al. |
| 5,807,241 A | 9/1998 | Heimberger et al. |
| 6,053,922 A | 4/2000 | Krause et al. |
| 6,447,518 B1 | 9/2002 | Krause et al. |
| 8,382,742 B2 | 2/2013 | Hermann et al. |
| 2004/0044270 A1 | 3/2004 | Barry |
| 2004/0249367 A1 | 12/2004 | Saadat et al. |
| 2006/0058582 A1 | 3/2006 | Maahs et al. |
| 2009/0187244 A1 | 7/2009 | Dross |
| 2010/0151161 A1 | 6/2010 | Da Rolo |
| 2012/0065638 A1* | 3/2012 | Moore ................... A61B 17/72 606/62 |
| 2012/0238952 A1 | 9/2012 | Mitchell et al. |
| 2013/0165908 A1 | 6/2013 | Purdy et al. |

OTHER PUBLICATIONS

International Search Report and the Written Opinion dated Jul. 7, 2015 From the International Searching Authority Re. Application No. PCT/IL2015/050178.
International Search Report and the Written Opinion dated May 5, 2017 From the International Searching Authority Re. Application No. PCT/IL2017/050062. (11 Pages).

* cited by examiner

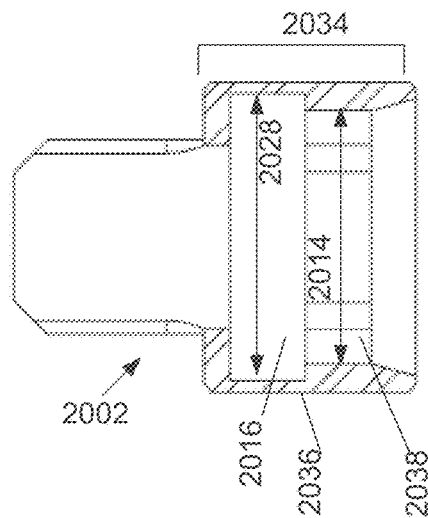
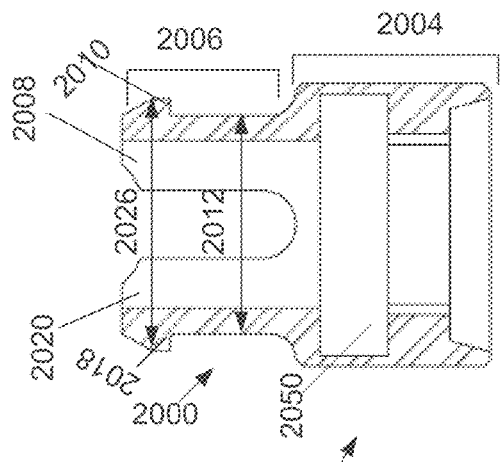
FIG. 2A2
FIG. 2A1
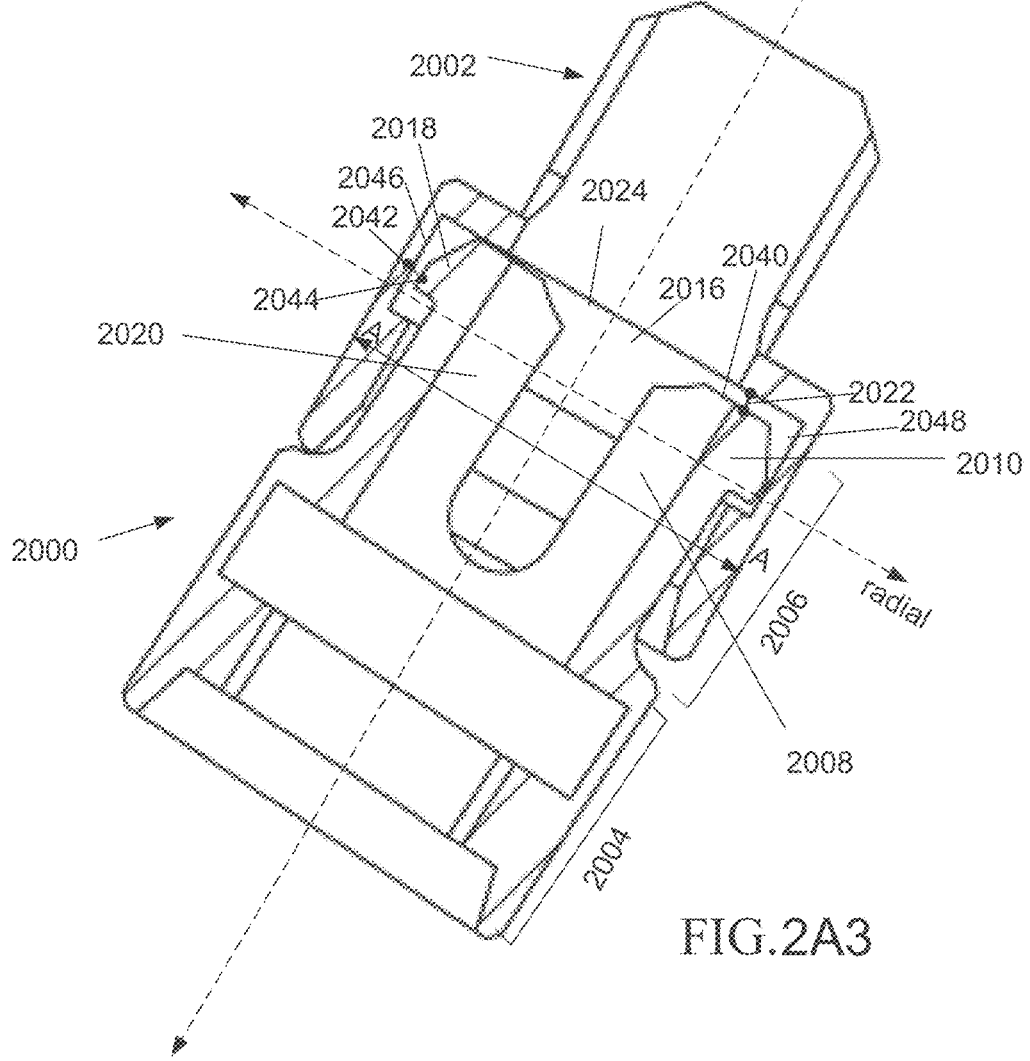
FIG. 2A3

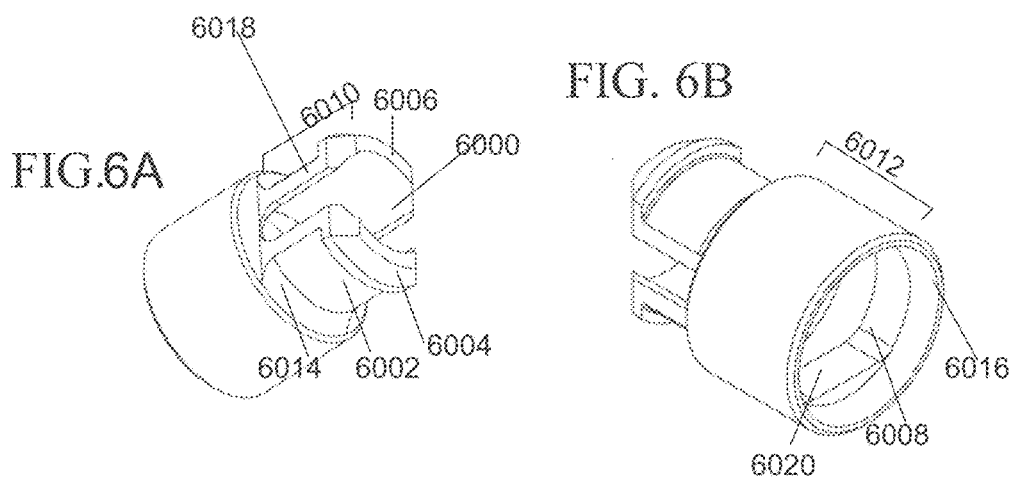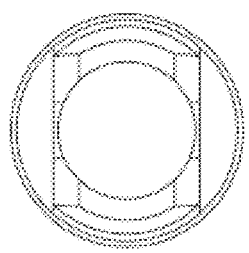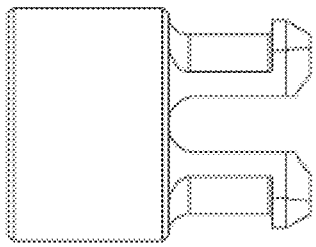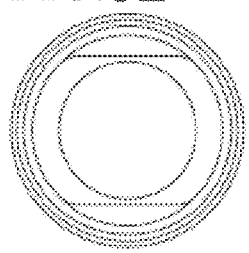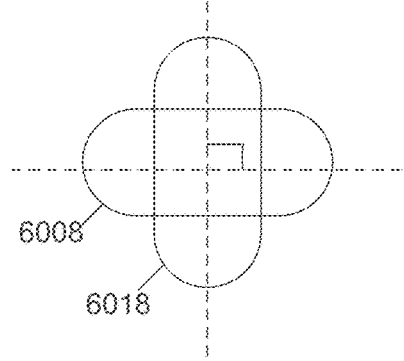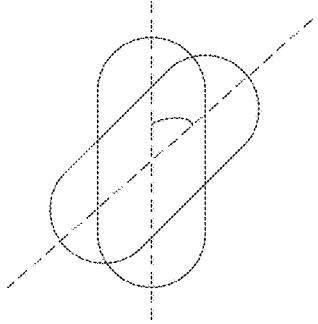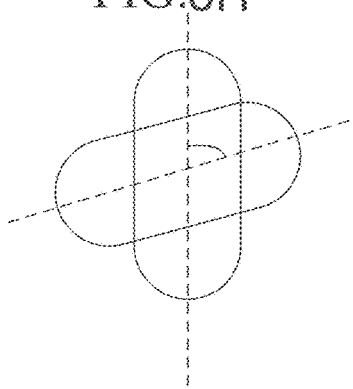

FIG. 35C
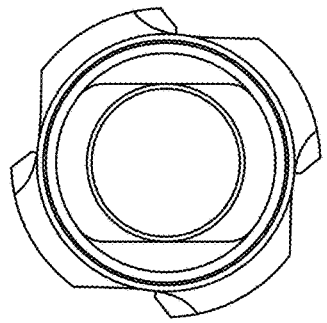
FIG. 35B
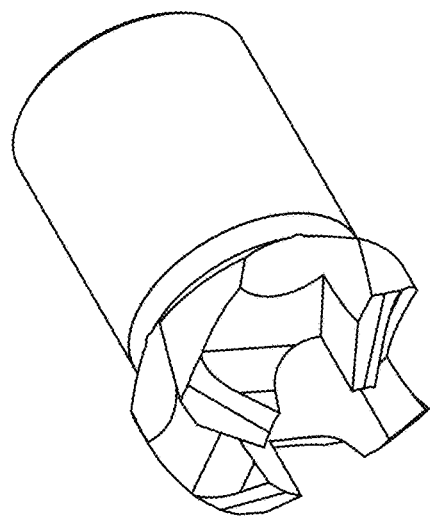
FIG. 35E
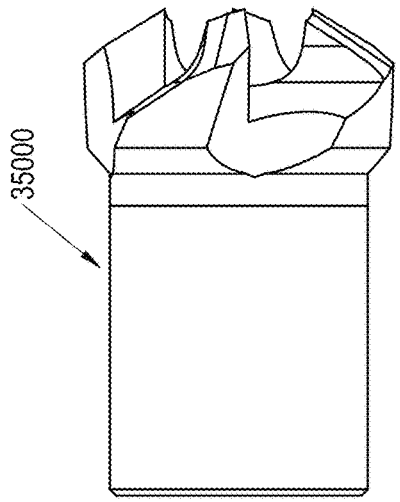
FIG. 35D
FIG. 35A
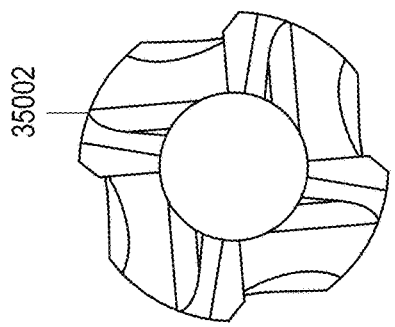
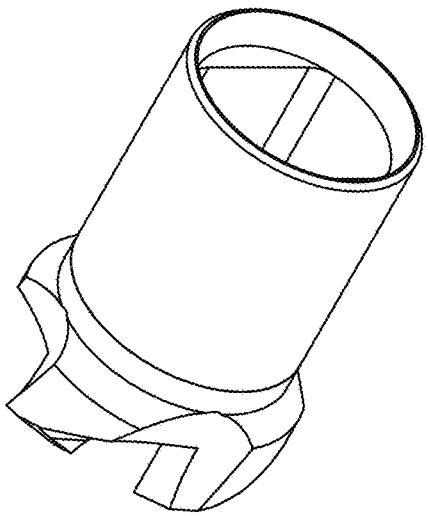

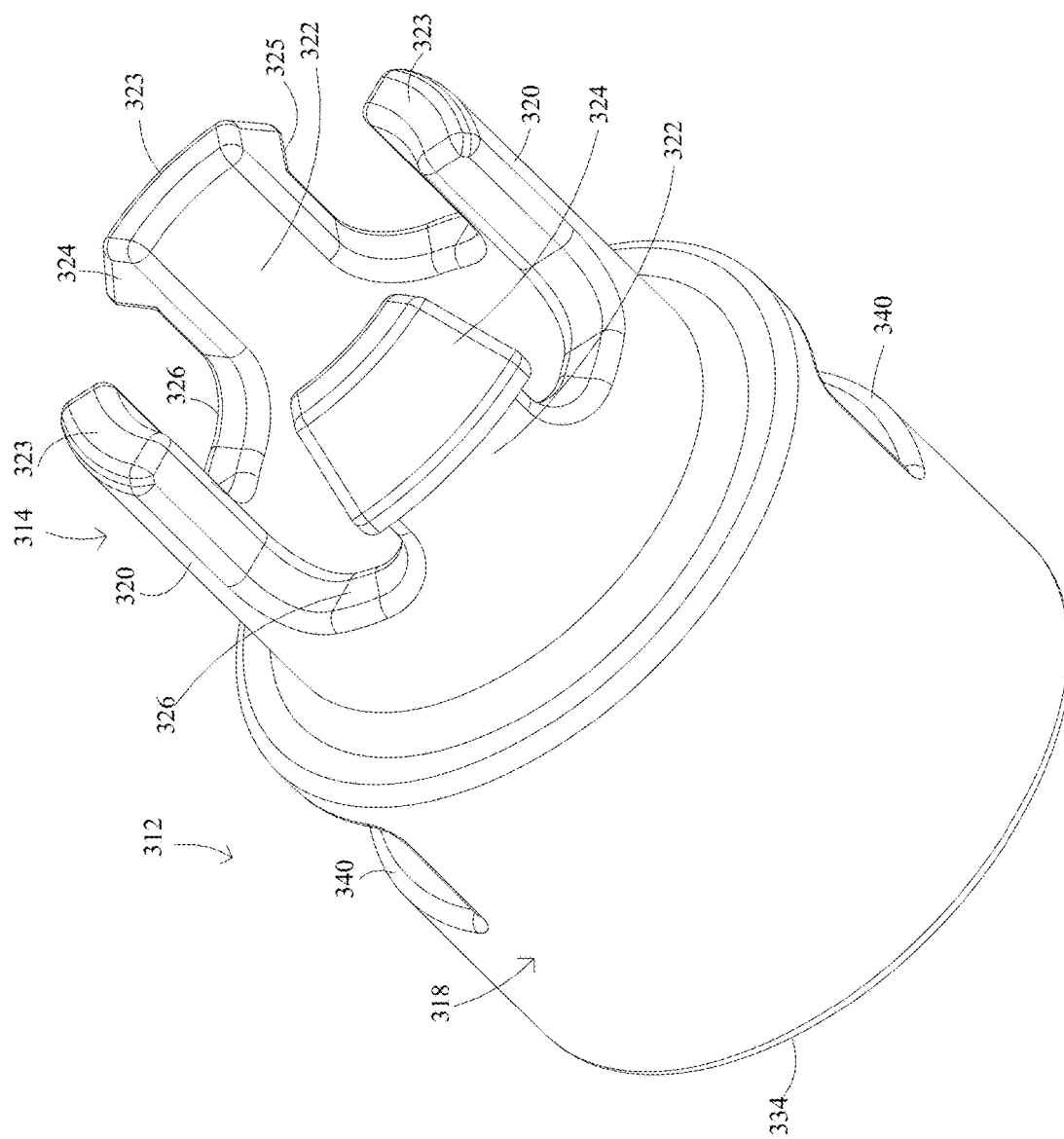

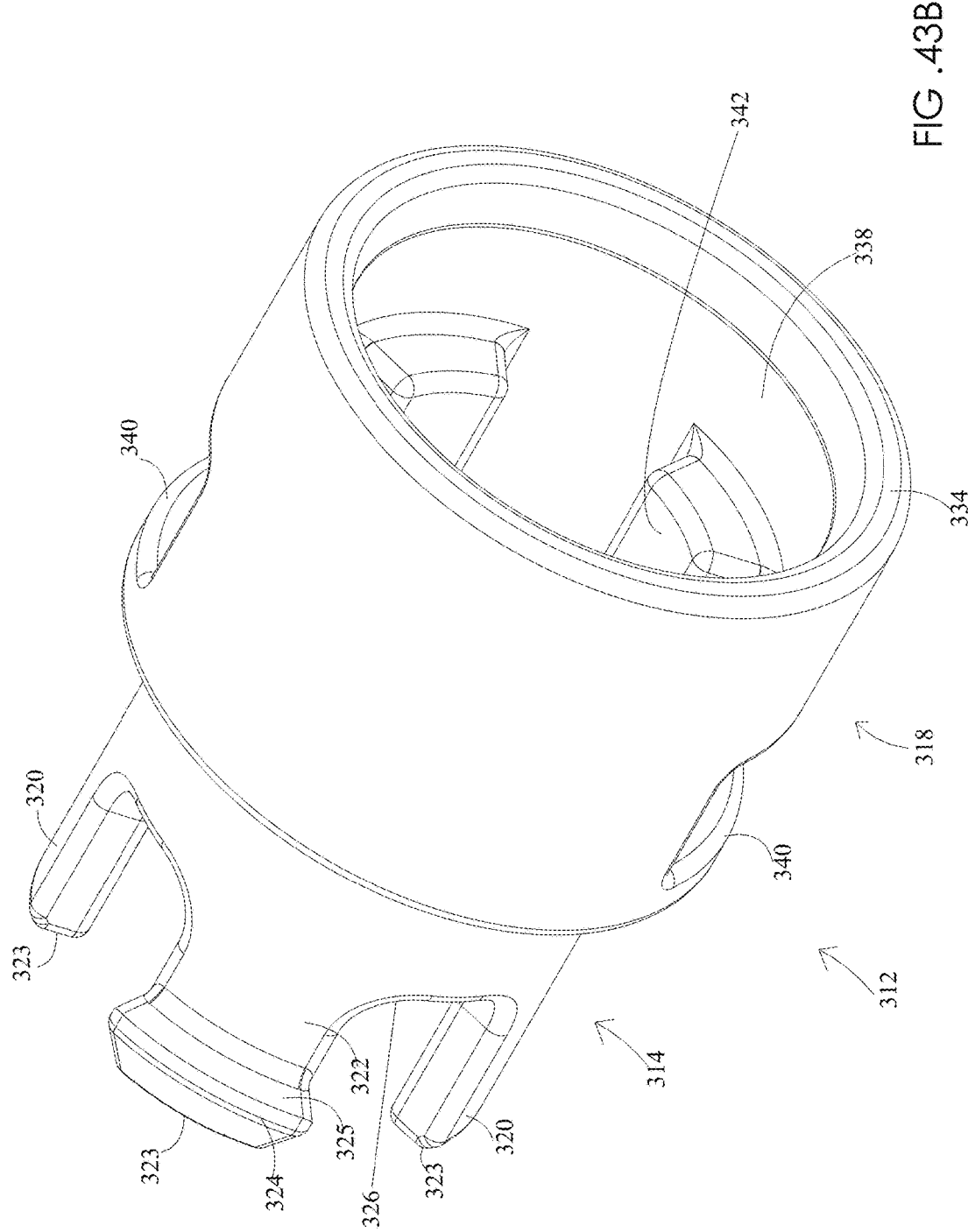

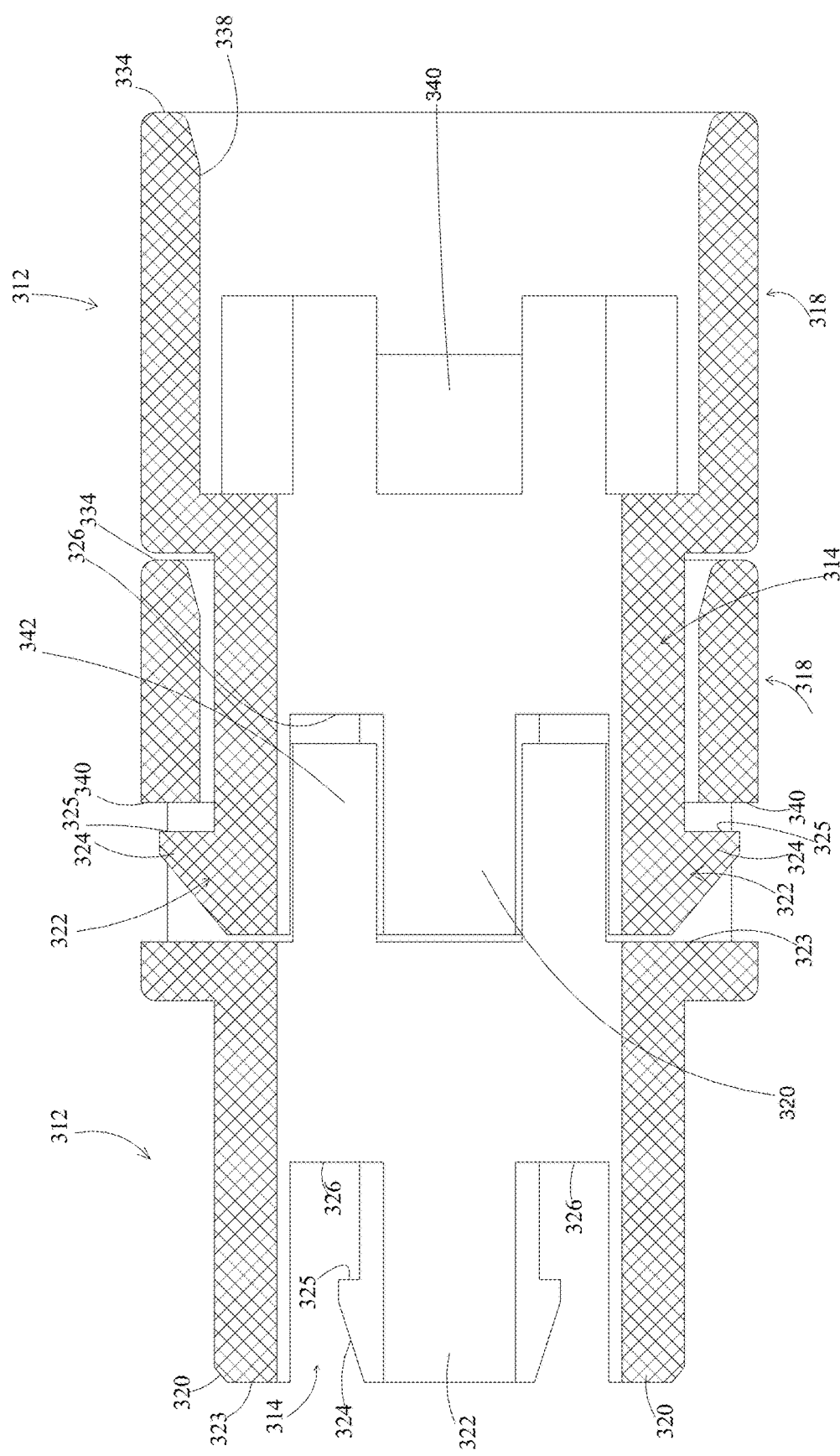

FLEXIBLE BONE TOOL

RELATED APPLICATIONS

This application is a National Phase of PCT Patent Application No. PCT/IL2015/050178 having International filing date of Feb. 17, 2015, which claims the benefit of priority under 35 USC §119(e) of U.S. Provisional Patent Application No. 61/940,609 filed Feb. 17, 2014, The contents of the above applications are all incorporated by reference as if fully set forth herein in their entirety.

FIELD AND BACKGROUND OF THE INVENTION

The present invention, in some embodiments thereof, relates to a flexible bone tool and, more particularly, but not exclusively, to a flexible bone tool configured to be advanced into a bone in an arthroscopic procedure.

US Publication number 6447518 B1 discloses: "An improved flexible shaft used in the reaming of the medullary space in bones is described. The shaft is comprised of a solid element with a longitudinal bore the entire length and an appropriately formed slot which extends spirally around the shaft either continuously or segmentally. Attached to the shaft's opposite ends respectively, are a cutting head and a means of connecting the shaft to a driving mechanism. Additionally, an improved anthropomorphic spinal element and vertebral body replacement implant are described. The anthropomorphic spinal element is composed of a solid element with a longitudinal bore and an appropriately formed slot that extends spirally around the shaft either continuously or segmentally and is completely or partially filled with an elastomeric material. The vertebral body replacement implant is composed of a suitable implant material with a longitudinal bore the entire length and an appropriately formed slot which extends spirally around the shaft either continuously or segmentally. Attached to the central section's opposite ends are a means of attachment to the adjacent vertebra allowing for height and angular adjustment."

US publication number 4362520 A discloses: "This invention is a heavy-duty flexible shaft that accommodates for misalignments between an input and output shaft. The flexible shaft is comprised of a multiplicity of hollow, individually fabricated, interfitting members housed in a tubular, bendable shaft. Each segment is intimately engaged, one within the other, yet the segments are so designed to allow for limited longitudinal movement while restricting circumferential movement between segments during torsional transmissions from the input to the output shafts."

SUMMARY OF THE INVENTION

According to an aspect of some embodiments of the invention, there is provided a flexible bone tool comprising a bone tissue removal element configured at a distal end of the tool; at least two links coupled proximally to the bone tissue removal element, the links connected to each other by a radial interference connection in which at least one radially outwards extending protrusion of a first link is received within a recess of a subsequent link.

According to some embodiments of the invention, each of the links comprises an engaging portion and a receiving portion, the engaging portion positioned distally relative to the receiving portion.

According to some embodiments of the invention, the receiving portion comprises an inner lumen open at a proximal end of the link and leading to the recess, the recess being large enough to receive the at least one protrusion without compressing it inwardly.

According to some embodiments of the invention, the connection is a snap-fit connection in which the at least one radial protrusion is compressed inwardly by the inner lumen of the subsequent link and advanced distally until the protrusion is allowed to elastically snap into the recess, interlocking the first link and the subsequent link to each other while allowing bending of the links relative to each other.

According to some embodiments of the invention, the first link and the subsequent link comprise matching geometries suitable for transferring torque between the links at a magnitude sufficient for advancing the bone tissue removal element into a bone.

According to some embodiments of the invention, the matching geometries comprise at least one surface shaped to interfere with axial rotation of the links relative to each other.

According to some embodiments of the invention, the matching geometries comprise mutual flat faces that contact each other at least one part, wherein a first flat face is configured on the engaging portion of the first link, and a second flat face is configured within the inner lumen of the receiving portion of the subsequent link.

According to some embodiments of the invention, the magnitude of torque ranges between 3 N*cm to 30 N*cm.

According to some embodiments of the invention, the first link and the subsequent link each comprise a receiving recess, wherein the recesses of both links have substantially the same design and are configured to be rotationally oriented relative to each other such that the receiving recess of the first link is configured at an angle to the receiving recess of the subsequent link.

According to some embodiments of the invention, the angle is 90 degrees.

According to some embodiments of the invention, a volume of the at least one radial protrusion occupies no more than 95% of a volume of the recess.

According to some embodiments of the invention, the recess does not extend beyond an outer edge of the receiving portion and the protrusion is internally received within the receiving portion.

According to some embodiments of the invention, the recess extends through an outer edge of the receiving portion and the protrusion is long enough to extend through the recess.

According to some embodiments of the invention, the engaging portion comprises at least one tooth like extension extending in a distal direction, and wherein the protrusion extends radially outwards from the tooth like extension.

According to some embodiments of the invention, the links define a tubular body.

According to some embodiments of the invention, the tubular body is configured to bend into a bending radius of 30 mm or higher.

According to some embodiments of the invention, the tool is cannulated, and wherein the cannulation is shaped and sized to allow delivery of the tool over a guide wire.

According to some embodiments of the invention, the bone tissue removal element is shaped and sized to form a bore in the bone.

According to some embodiments of the invention, the bone tissue removal element is shaped and sized to ream an existing bore in the bone.

According to some embodiments of the invention, the tool further comprises a holding section at proximal end of the tool, the holding section engageable by a user or a tool.

According to some embodiments of the invention, the tool is a drill.

According to an aspect of some embodiments of the invention, there is provided a method of advancing a flexible bone tool into a bone, comprising providing a flexible bone tool comprising a plurality of links interlocked to each other by a radial interference connection; introducing the flexible bone tool over a guide wire to approach the bone; rotating the tool to advance at least a distal end of the tool into the bone.

According to some embodiments of the invention, the links are rigid, and wherein the introducing comprises advancing the tool along a curved path defined by the guide wire such that the rigid links bend relative to each other.

According to some embodiments of the invention, an axial gap between adjacent links of the plurality of links is reduced upon contacting the bone.

According to some embodiments of the invention, the advancing comprises forming a bore in the bone.

According to some embodiments of the invention, the advancing comprises reaming an existing bore in the bone.

According to some embodiments of the invention, the bone is the femur and the rotating reams a tunnel in the femur for receiving a graft.

According to some embodiments of the invention, the rotating comprises coupling a drill to a proximal end of the bone tool.

According to an aspect of some embodiments of the invention, there is provided a flexible bone tool comprising a bone tissue removal element configured at a distal end of the tool; at least two links coupled proximally to the bone tissue removal element, the links interconnected to each other by a snap-fit connection in which a first link comprises at least one protrusion which is compressed inwards by an inner lumen of a subsequent link until the at least one protrusion is allowed to elastically snap into a respective recess of the subsequent link that the inner lumen leads to.

According to some embodiments of the invention, the inner lumen is open at a proximal end of the subsequent link and extends longitudinally within a receiving portion of the subsequent link, the inner lumen shaped and sized to compress the at least one protrusion radially inwards.

According to some embodiments of the invention, the snap-fit connection interlocks the first link and the subsequent link to each other while allowing bending of the links relative to each other.

According to an aspect of some embodiments of the invention, there is provided a kit for adjusting a flexible bone tool, comprising a plurality of interconnectable links, the links configured to engage each other by a snap-fit connection to form an elongated, bendable body.

According to some embodiments of the invention, the tool comprises a proximal holding portion and wherein at least one of the links is configured to engage the proximal holding portion.

According to some embodiments of the invention, the kit further comprises a plurality of cutting heads out of which one cutting head is selected, the cutting head configured to engage a distal end of at least one of the links.

According to an aspect of some embodiments of the invention, there is provided a method of adjusting a flexible bone tool, comprising: providing a flexible bone tool comprising a plurality of links interconnected to each other by a snap-fit connection; attaching or removing one or more links to adjust a length of the bone tool.

According to some embodiments of the invention, the method further comprises selecting a cutting head of a certain shape or size and connecting the cutting head to a most distal link of the plurality of links.

According to some embodiments of the invention, the attaching or removing provides at least one of audible, sensible or visible feedback to the user.

According to some embodiments of the invention, the audible feedback comprises a "click" type sound when the links interlock to each other.

According to an aspect of some embodiments of the invention, there is provided a flexible bone tool comprising a bone tissue removal element configured at a distal end of the tool; at least two links coupled proximally to the bone tissue removal element, the links interconnected to each other by a "click" type connection in which a sound indication is provided in the process of connecting the links.

According to an aspect of some embodiments there is provided a flexible reamer slidable over a guide pin, comprising:

a proximal holding portion;

an intermediate portion;

a distal portion including a plurality of interconnected links, attached in an articulated manner, which allows force transfer from one link to a subsequent link in a direction corresponding to the direction of the guide pin.

In some embodiments, the flexible reamer also comprises a distal drilling end.

In some embodiments, the guide pin is made of Nitinol.

In some embodiments, the links are inseparably interconnected.

In some embodiments, the links are interconnected by a snap-fit.

In some embodiments, a fulcrum point of said distal portion is formed at a most-proximal link.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A-H are views of a link in accordance with FIGS. 2A1-C from various directions and cross sections (A-E), and a schematic illustration of an angular orientation between receiving recesses of adjacent links (F-H), according to some embodiments of the invention;

FIGS. 35A-E illustrate another configuration of a distal cutting head configured to engage a flexible bone tool in accordance with FIG. 28, according to some embodiments of the invention;

FIGS. 43A-B are simplified pictorial illustrations of a single link of the flexible reamer of FIG. 42, shown from the distal end and from the proximal end respectively;

FIG. 46 is a simplified section view of interconnected two links of FIGS. 43A & 43B;

DESCRIPTION OF SPECIFIC EMBODIMENTS OF THE INVENTION

Figure 1:
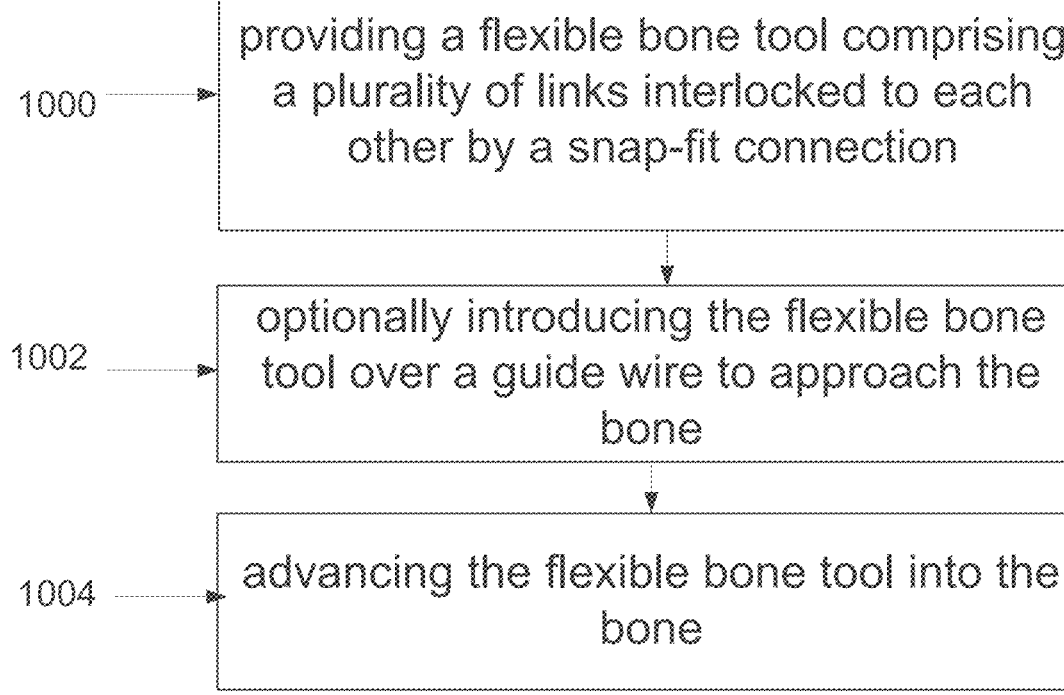
FIG. 1 is a flowchart of a method of advancing a flexible bone tool comprising a plurality of links interlocked by a snap fit connection into a bone, according to some embodiments of the invention.

The present invention, in some embodiments thereof, relates to a flexible bone tool and, more particularly, but not exclusively, to a flexible bone tool configured to be advanced into a bone, for example in an arthroscopic procedure. Some embodiments relate to a flexible bone tool comprising a bone tissue removal element at a distal end of the tool, configured for example for forming a bore in the bone and/or reaming an existing bore in the bone.

An aspect of some embodiments of the invention relates to a flexible bone tool comprising a plurality of links interconnected to each other by a radial interference connection. In some embodiments, the links are arranged along a common axis to form an elongated, optionally tubular body. In some embodiments, the radial interference connection comprises at least one protrusion of a first link which extends in a radially outwards direction relative to the long axis of the elongated body, to be received within a respective recess of a subsequent link.

In some embodiments, a link comprises a receiving portion and an engaging portion, the engaging portion configured distally to the receiving portion. Optionally, the receiving portion comprises an inner lumen leading to the recess in which the protrusion is received. In some embodiments, the protrusion is sized to occupy a volume smaller than a volume defined by the respective recess, so that during flexion of the elongated body the protrusion is free to move to at least some extent within the recess and provide for bending of the interconnected links relative to each other.

In some embodiments, the radial protrusion is received internally within the receiving portion of the link. Alternatively, the respective recess extends to an outer edge of the receiving portion of the link and the radial protrusion is long enough to extend through the recess, so that it is aligned with or extends beyond an outer edge of the link.

An aspect of some embodiments of the invention relates to a flexible bone tool comprising a plurality of links interconnected to each other by a snap-fit connection. In some embodiments, the engaging portion of a link comprises at least one elastic element on which the protrusion is configured. In some embodiments, the elastic element is a tooth-like extension, extending in a distal direction. In some embodiments, an inner lumen of the receiving portion of a subsequent link which leads to the respective recess is shaped and sized to compress the elastic element inwardly upon insertion of the link into the subsequent link, until the protrusion is allowed to spring outwardly and snap fit into the respective recess.

In some embodiments, the connection between the links provides for bending of the links relative to each other, enabling advancing of the tool along a curved path, such as when approaching the bone and/or when advancing into the bone. In some embodiments, the tool is introduced over a curved or straight guide wire which defines the path to and/or into the bone, and can be flexed to closely follow the path defined by the guide wire. Optionally, the elongated body can be flexed into a bending radius as small as 50 mm, 30 mm, 60 mm or intermediate, larger or smaller radii. I In some embodiments, the snap-fit connection is configured to maintain the coupling between the links, for example by resisting pull-out force acting on the tool during retraction from the body.

An aspect of some embodiments of the invention relates to a flexible bone tool comprising a plurality of links interconnected to each other, the links comprising a matching geometry which is structured to allow transferring of force such as torque between the links at a magnitude sufficient for advancing at least a distal end of the tool into the bone. In some embodiments, torque is applied to a proximal end of the tool, for example by a drill, and is transferred in a distal direction by the interconnected links. In some embodiments, a cutting head is configured at a distal end of the tool, and torque at a magnitude sufficient for forming a bore in the bone and/or for reaming an existing bore in the bone is transmitted by the links in the distal direction to the cutting head.

In some embodiments, the matching geometry of the links includes at least one surface shaped to interfere with axial rotation of a link relative to the adjacent link. In some embodiments, the matching geometry of the links includes flat surfaces that at least partially contact each other when the links are connected. In some embodiments, the mutual flat surfaces are positioned to limit an extent of axial rotation of a link relative to the subsequent, receiving link. Optionally, limiting the extent of rotation enables the transfer of torque between the links.

In some embodiments, adjacent links are angularly rotated relative to each other. Optionally, a receiving recess of a link is positioned at an angle relative to the receiving recess of the subsequent link, for example a 30 degree, 60 degree, 90 degree, 120 degree angle.

An aspect of some embodiments relates to adjusting a flexible bone tool. In some embodiments, the tool is adjusted on-site, based on or more of the type of procedure, the anatomy of the patient, the targeted tissue, and/or other parameters. In some embodiments, a length of the tool can be adjusted by adding or removing one or more links. Optionally, a user such as a physician selects a desired length, and adjusts the tool before and/or during procedure. In some embodiments, a cutting head of a certain shape and/or size and/or function (e.g. a head configured for drilling, a head configured for reaming) is selected and attached at a distal end of the tool, for example connected to the most distal link.

In some embodiments, a connection between the links provides tactile and/or visible and/or audible feedback to a user adjusting the tool. Optionally, audible feedback is provided, for example, by a "click" sound made when the one or more protrusions are received within their respective recesses; visible feedback is provided, for example, by externally extending recesses in which the protrusions are received so that they are visible from outside the tool; and tactile feedback may be provided, for example, by resistance of the receiving link during insertion of the engaging portion of the preceding link, until the protrusions are advanced to fit within the one or more recesses. In some embodiments, an inner receiving lumen of the subsequent link is shaped and/or sized to at least partially resist insertion of the engaging portion of the preceding link, requiring that the engaging portion will be "squeezed" into the receiving recess up to a point in which the protrusions fit within their recesses. In some embodiments, a kit is provided, comprising one or more of a tool including a proximal holding section and one or more links attached distally to the holding section; a plurality of separate links for adding to the tool; and/or a plurality of cutting heads of various shapes and/or sizes and/or functions. Some embodiments may include an adjustment device configured to assemble the links and/or to detach the links and/or to assemble, replace or detach the cutting head.

As referred to herein, a "bone tissue removal element" and/or "cutting head" may include an element shaped and sized for one or more of forming a bore in the bone, reaming an existing bore in a bone, penetrating bone tissue, fragmenting or crumbling bone tissue, grinding the bone.

As referred to herein, the term "proximal" may refer to a direction of the user end of the tool, such as an outside the body direction; the term "distal" may refer to a direction of the targeted bone, away from the user end of the tool.

In some embodiments, during various arthroscopic procedures and particularly during Anterior Cruciate Ligament Reconstruction (ACL Reconstruction), a surgical tissue graft is inserted into a bore created in the knee in order to replace the injured anterior cruciate ligament. The injured ligament is removed from the knee before the graft is inserted through the bore created by drilling. One problem which may be associated with this technique is approaching the knee joint at a certain angle. Several methods have been developed for enabling engagement between the femoral bone and the reamer at a certain angle. An exemplary method is to position a drill guide and guide pin through on the femoral bone and slide a reamer over the guide pin in order to create the femoral tunnel.

Some embodiments relate to a flexible surgical reamer, which provides for convenient positioning of the drill against the femoral bone.

The present invention relates to flexible reamers for use in arthroscopic reconstruction procedures, particularly useful in Anterior Cruciate Ligament Reconstruction (ACL) procedures.

Some embodiments of the invention seek to provide an improved flexible reamer for drilling a tunnel in a human femoral bone.

There is thus provided in accordance with an embodiment of the present invention a flexible reamer slidable over a guide pin. In some embodiments, the reamer includes a proximal holding portion, an intermediate portion, a distal portion including a plurality of interconnected links. Optionally, the links are attached in an articulated manner, which allows force transfer from one link to a subsequent link in a direction corresponding to the direction of the guide pin.

In accordance with an embodiment of the present invention, the flexible reamer also includes a distal drilling end.

Optionally, the guide pin is made of Nitinol.

Further in accordance with an embodiment of the present invention, the links are inseparably interconnected. Additionally or alternatively, the links can be separated from each other, for example by applying pull out force over a certain threshold, for example outside the body.

In some embodiments, the links are interconnected by a snap-fit.

Yet further in accordance with an embodiment of the present invention, a fulcrum point of the distal portion is formed at a most-proximal link.

Some embodiments relate to a flexible reamer slidable over a guide pin, including a proximal holding portion, an intermediate portion, a distal portion including a plurality of interconnected links, attached in an articulated manner, which allows force transfer from one link to a subsequent link in a direction corresponding to the direction of the guide pin.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a flowchart of a method for advancing a flexible bone tool comprising a plurality of links interconnected by a snap-fit connection into a bone, according to some embodiments of the invention.

In some embodiments, a flexible bone tool comprising a plurality of links interconnected by a snap-fit connection, for example as further described herein, is provided (1000). In some embodiments, the links are arranged along a common longitudinal axis. In some embodiments, the chained links define a substantially tubular, bendable body. In some embodiments, the bone tool comprises a cutting head configured at a distal end of the tubular body. Optionally, the cutting head is shaped and/or sized to cut a bore in the bone, allowing the tool to function as a drill bit. Additionally or alternatively, the cutting head is shaped and/or sized to widen an existing bore in the bone, for example when rotary motion is applied to the tool, for example to a proximal head portion of the tool, allowing the tool to function as a reamer. In some embodiments, the bone tool comprises a holding section configured proximally to the tubular body. The proximal holding section may be engaged by a user, such as a physician, and/or by an additional tool, such as a drill. In some embodiments, the tubular body and optionally the proximal holding portion are cannulated. Optionally, the cannulated tool is delivered over a guide wire, guide pin, suture and/or other elongated elements that can fit within and/or be passed through the cannulation.

In some embodiments, a guide wire is introduced to the targeted bone. Optionally, an initial bore is drilled in the bone, for example by advancing the guide wire into the bone, such as with the aid of a drill. In some embodiments, at least a portion of the guide wire is bent into an arch or other curved profile. Optionally, the guide wire is bent into a selected curvature once at least a part of it (e.g. a distal end) has been anchored to the targeted bone.

In some embodiments, the flexible bone tool is introduced over the guide wire (1002). Optionally, the guide wire defines a curved path leading the flexible bone tool to the bone. Alternatively, the guide wire defines a substantially linear path leading to the bone. In some procedures, it is necessary or preferable to access the bone by following a curved path, (i.e. rather than directly accessing the bone), for example due the anatomy of the treated area. In some procedures, the targeted bone is approached at a certain angle. A flexible tool as described herein may be particularly useful in such procedures, owing to the articulation ability of the tubular body.

In some embodiments, the flexible bone tool is advanced into the bone (1004). In some embodiments, advancing the tool comprises axially rotating the tubular body, for example by coupling a drill to the proximal holding section of the tool. Optionally, at least a portion of the tubular body of the tool is advanced into a pre-formed bore in the bone, and widens a diameter of the bore upon advancement. Alternatively, the tool produces the bore. In some embodiments, the snap-fit connection between the plurality of links of the tubular body is strong enough to withstand resisting forces of the bone, while allowing transmission of force such as torque between the links, for example from the proximal holding section to the distal head.

A method for example as described herein may be especially advantageous in arthroscopic procedures, and particularly useful in Anterior Cruciate Ligament Reconstruction procedures, in which a bore is formed in the femoral bone. In some cases, the bone is approached at a certain angle for forming the bore. Optionally, a flexible bone tool in accordance with some embodiments is introduced to the femoral bone, (optionally over a bent guide wire that was used for creating an initial bore in the bone), and functions as a reamer for widening the initial bore to produce a tunnel for receiving a graft. Optionally, the tool is introduced along a curved path to meet the bone at a desired location.

In some embodiments, for example as further described herein, one or more structural properties of the flexible bone tool such as an axial length of the tubular body, diameter of the tubular body, and/or type of cutting head positioned at the distal end of the tubular body are selected by a user, such as a physician, in preparation for the procedure and/or during the procedure. In an example, a user adjusts the length of the tubular body by adding or removing links. In another example, a user selects a cutting head suitable for performing a desired function (e.g. penetrating a bone to produce a bore, widening an existing bore, and/or other functions), and assembles the head onto the tool.

Figure 2B:
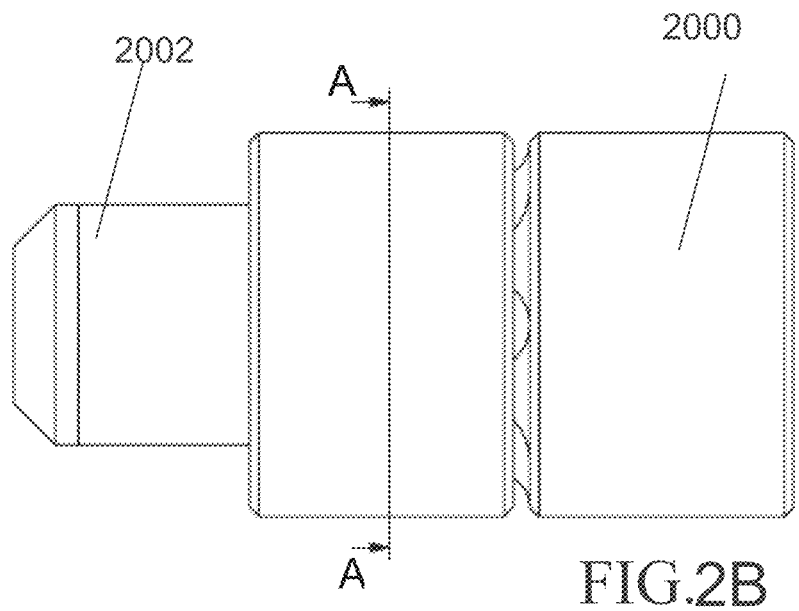
FIGS. 2A(1-3), 2B, 2C illustrate a longitudinal cross section of an exemplary structure of adjacent links of a flexible bone tool (2A1-2A3), a side view of the adjacent links (2B), and a transverse cross section along lines A-A (shown in FIG. 2B) of the adjacent links (2C) according to some embodiments of the invention.

FIGS. 2A(1-3), 2B, 2C illustrates a longitudinal cross section of an exemplary structure of adjacent links of a flexible bone tool (2A1-2A3), a side view of the adjacent links (2B), and a transverse cross section along lines A-A (shown in FIG. 2B) of the adjacent links (2C) according to some embodiments.

In the structure shown in FIGS. 2A1-2A3, a first link 2000 is connected to a subsequent, more distal link 2002 by a snap fit connection. In some embodiments, a link comprises a receiving portion 2004, and an engaging portion 2006, configured distally to the receiving portion to be received within a receiving portion of the subsequent link.

In some embodiments, engaging portion 2006 comprises a plurality of tooth-like such as extensions 2008 and 2020 extending distally from a distal end face of receiving portion 2004, each extension defining a wall that extends along at least a portion of a notional circumference of the engaging portion. In some embodiments, extensions 2008 and 2020 define a tubular outer shape. Alternatively, extensions 2008 define a different outer profile, such as hexagonal, oval, and/or other outer profile configured to be received within the receiving portion of the subsequent link.

In some embodiments, the outer profile defined by extensions 2008 comprises a diameter 2012 smaller than an inner diameter 2014 of a proximal portion of receiving portion 2034 of subsequent link 2002, so as to fit within the receiving portion. (Receiving portion 2034 is similar in structure to receiving portion 2004 of link 2000, but is separately referred to for clarity purposes).

In some embodiments, an extension comprises one or more protrusions such as 2010 (of extension 2008) and 2018 (of extension 2020), extending for example in a radially outwards direction from a distal end of the extension. In some embodiments, a protrusion such as 2010 is received within a recess 2016 defined within receiving portion 2034. In some embodiments, an extension is elastic to an extent which allows it to be pushed inwardly during attachment of the links to each other, until the protrusion can spring out outwardly when received within recess 2016. Optionally, the extension is pushed inwardly when passing through the lumen of proximal portion of receiving portion 2014, defined by diameter 2014.

Figure 12:
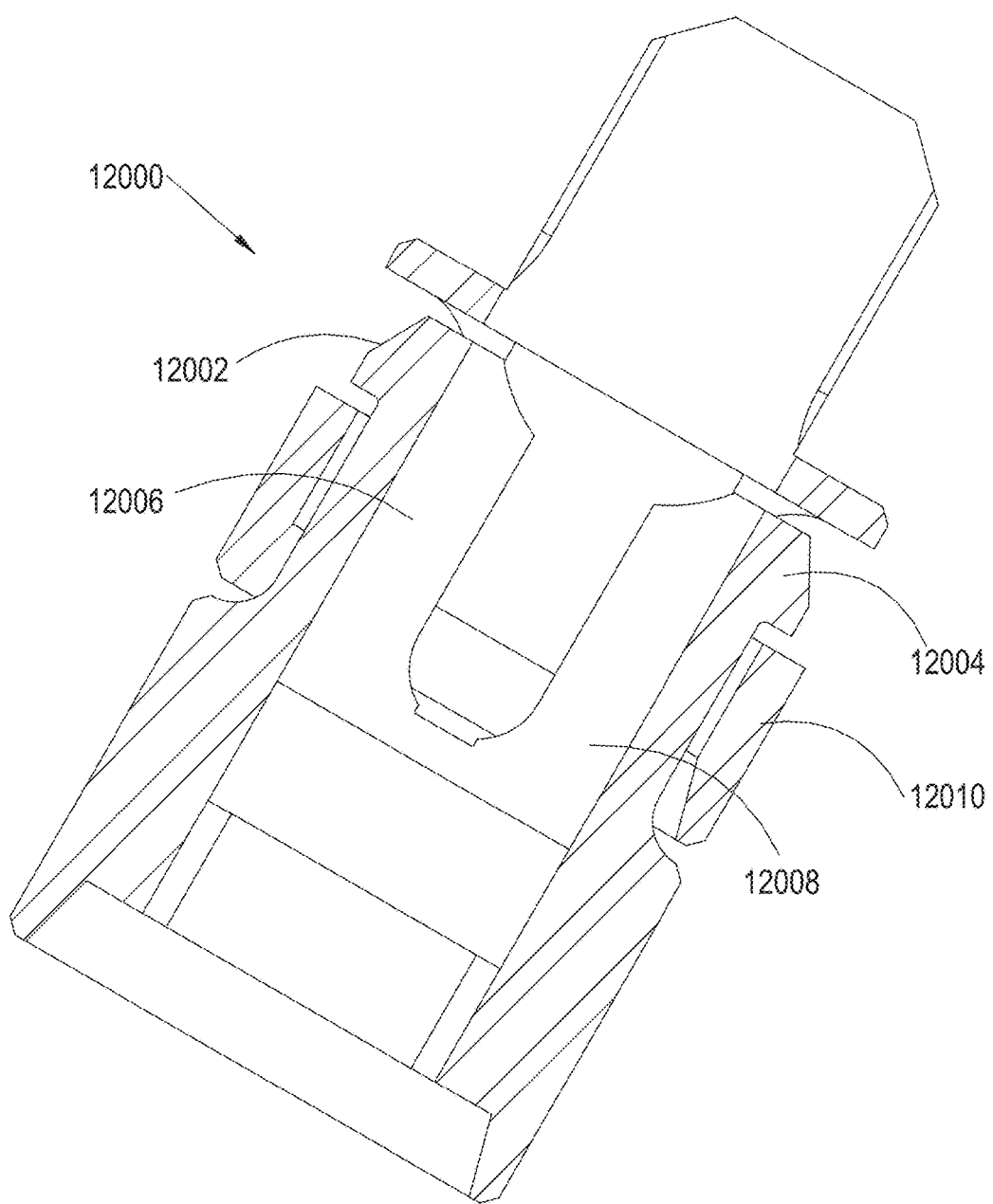
FIG. 12 is an exemplary link structure of the flexible bone tool, comprising radial protrusions for engaging one or more externally extending recesses of a subsequent link, according to some embodiments of the invention.

In some embodiments, for example as shown in FIG. 2A3, recess 2016 is formed internally within the shaft of receiving portion 2034. Alternatively, recess 2016 extends all the way through to the outer face 2036 of receiving portion 2034, so that protrusion 2010, when positioned within recess 2016, is aligned with or protrudes radially outwards relative to the outer face 2036, for example as shown in FIG. 12 below. In some embodiments, recess 2016 comprises a diameter 2028 larger than inner diameter 2014 of a more proximal portion of the inner lumen of 2038 that leads to recess 2016.

Some embodiments may include both an internal recess and an externally-extending recess, configured for example on diametrically opposing sides of receiving portion 2034. Optionally, a matching engaging portion 2006 of such configuration will comprise a first protrusion which extends radially outwards to a distance that is within the range of diameter 2014 of receiving portion 2034, to fit within the internal recess, and a second protrusion diametrically opposing the first protrusion that extends radially outwards to a larger distance so that it is aligned with or extends beyond an outer face of receiving portion 2034.

In some embodiments, a radial protrusion 2010 is shaped and/or sized relative to recess 2016 such that at least some volume of the recess remains unoccupied by the protrusion. Optionally, this allows for movement, at least to some extent, of the protrusion within the recess, for example movement in an axial and/or radial direction.

In the cross section shown in FIG. 2A3, in which link 2000 is bent relative to subsequent link 2002, it can be observed that the distances of protrusion 2010 and/or of a distal face 2040 of extension 2008 from the inner walls such as wall 2024 of recess 2016 are different than the equivalent distances of opposing extension 2020 and protrusion 2018 from the walls of the recess. Optionally, a distance between the protrusion and one or more walls of the recess varies during bending of the links relative to each other. In an example, a distance 2022 between a distal face 2040 of extension 2008 and a distal inner wall 2024 of recess 2016 is larger than the corresponding distance of a distal face of extension 2020 from distal inner wall 2024 of the recess. In this example, extension 2020 is shown in proximity to or even contacting distal inner wall 2024 of recess 2016. A distance such as 2022 may vary along the distal face 2040 of the extension 2010. Optionally, distance 2022 changes in response to flexing of the tool and/or in response to tension or compression forces acting on the tool, which may axially distance the links away from each other or axially approximate the links relative to each other, respectively. In some embodiments, distance 2022 may vary in different links of a single tubular body.

In a similar manner, a radial distance such as 2042 can be formed between a radially outward facing end face 2044 of the protrusion and a side wall 2046 of the recess (in this example, there is a larger space between protrusion 2018 and wall 2046 of the recess relative to the space between protrusion 2010 and the opposite side wall 2048 of the recess). A potential advantage of an extension that is moveable at least to some extent within the recess may include increasing the flexibility of the tool, providing for a larger range of bending radii of the tubular body. Another potential advantage may include increasing the ability of the tool to accommodate axial forces such as tension or compression acting on the tool.

In some embodiments, an interference fit in an "inner to outer" direction between the links is provided (e.g. in a radially outwards direction). Optionally, the interference fit is configured on a plane perpendicular or otherwise crossing a plane on which the longitudinal axis of at least the receiving link is configured. In some embodiments, link 2000 snap-fits into link 2002 as protrusions 2010 and 2018, which extend to a diameter 2026 larger than inner diameter 2014 of a proximal portion of the inner lumen 2038 of receiving portion 2034, are compressed radially inwards during insertion of the engaging portion into the receiving portion 2034, and upon reaching recess 2016, which comprises a diameter 2028 larger than diameter 2014, spring out in a radially outwards direction to snap fit within the recess. Optionally, a "click" sound is produced when the links lock to each other, indicating to the user that the links are attached, for example when assembling and/or adjusting a length of the flexible tool.

In some embodiments, each link comprises a plurality of extensions such as extensions 2008 and 2020, for example 2, 3, 4, 5, 6, 10 or intermediate, larger or smaller number of extensions. Optionally, links of a single tool comprise different numbers of extensions. Optionally, the number of extensions determines the extent of movement of the links relative to each other. For example, a single extension may provide for a higher degree of freedom of movement relative to a larger number of extensions, for example movement in the axial and/or radial directions.

In some embodiments, the snap fit connection is strong enough to resist axial pull-out forces acting on the links, for example during retraction of the tool out of the body. Optionally, the axial pull out force that needs to be applied when separating the links (e.g. during adjustment of the tool prior to insertion into the body) is determined by the number of extensions that couple the links together, for example, a stronger pulling force will need to be applied for separating links having a 4-extension configuration than links having a 2-extension configuration.

In some embodiments, the links are oriented at an angle relative to each other. Optionally, recess 2050 of receiving portion 2004 of link 2000 is at an angle to recess 2016 of the receiving portion 2034 of the subsequent link 2002. In some embodiments, the links are perpendicularly oriented relative to each other.

In some embodiments, a link is formed of metal, such as stainless steel. Additionally or alternatively, a link is formed of a biocompatible plastic, such as polycarbonate and/or isoplast.

In some embodiments, at least one link and/or at least the tubular body and/or cutting head are disposable.

Figure 2C:
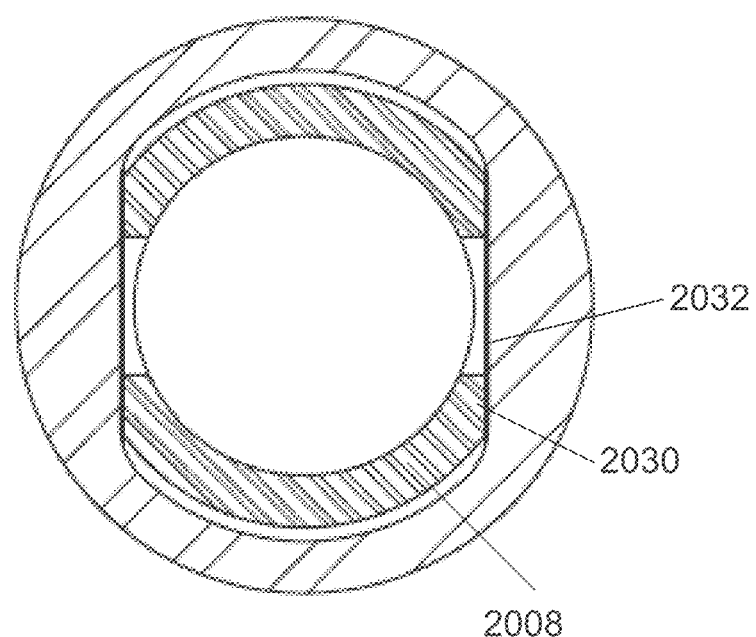

FIG. 2B shows a side view of the connected links 2000 and 2002. A potential advantage of the internal recesses such as recess 2016 may include a smooth outer profile of the tubular body, which may reduce accumulation of debris (e.g. cut bone chips) in the device. FIG. 2C shows a transverse cross section view (i.e. on a plane perpendicular to a long axis of the link) along lines A-A of FIG. 2B. In some embodiments, a tooth like extension such as 2008 comprises one or more flat faces 2030 that match a respective flat face 2032 of an inner lumen of the receiving portion which is proximal to recess 2016. In some embodiments, the flat faces are positioned to at least partially contact each other. In some embodiments, the matching flat faces 2030 and 2032 provide for the transfer of torque between the connected links 2000 and 2002. Optionally, the flat faces limit the extent of axial rotation of link 2000 relative to subsequent link 2002 such that torque can be transferred in the distal direction. In some embodiments, a surface area of the contacting flat faces comprises at least 20%, at least 40%, at least 50% or intermediate, larger or smaller percentages of a total contact area formed between the links. An exemplary surface area of flat face 2030 ranges between, for example, 0.5 mm^2 to 10 mm^2, such as 1 mm^2, 4 mm^2, 6 mm^2 or intermediate, larger or smaller surface areas.

In some embodiments, the magnitude of torque transferred by the links is sufficient for drilling into the bone tissue, for example ranging between 3N*cm-15 N*cm. Optionally, the tubular body is configured to transfer a magnitude of torque ranging between 1N*cm to 150 N*cm, such as 5-20 N*cm, 10-40 N*cm, 50-100 N*cm.

In some embodiments, the matching non-circular geometries of the engaging portion and the inner lumen of the receiving portion are selected to allow axial rotation of the links relative to each other only to an extent in which sufficient torque can still be transferred between the links.

Figure 3A:
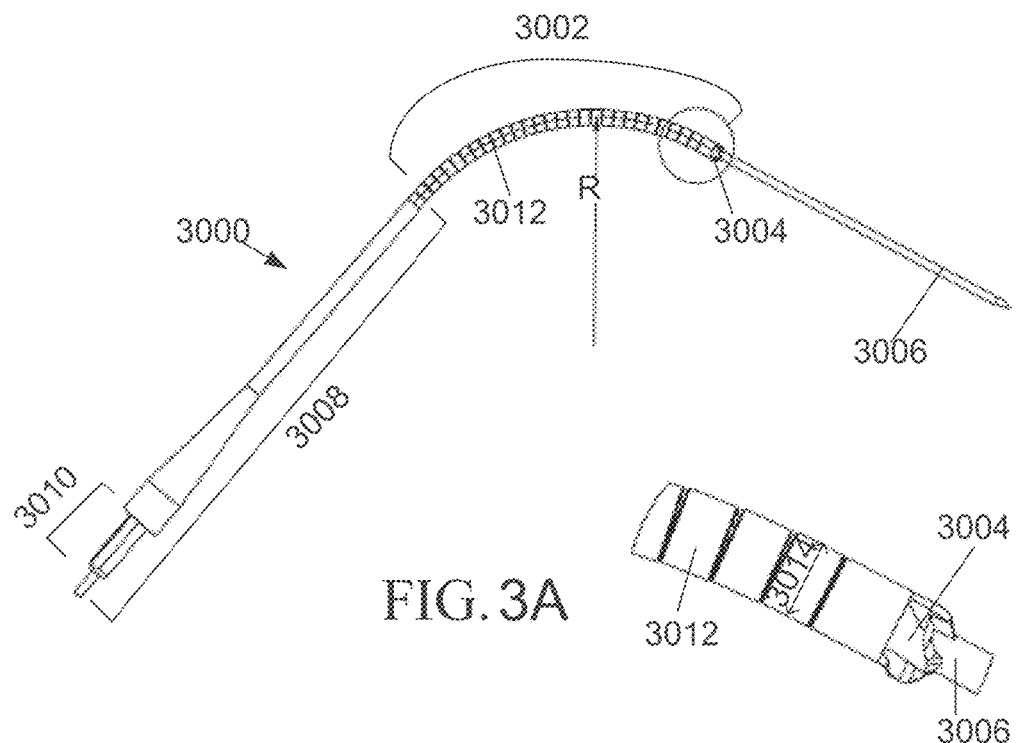
FIGS. 3A-B illustrate a flexible bone tool in accordance with FIGS. 2A1-C in a flexed configuration (3A) and straight configuration (3B), according to some embodiments of the invention.
Figure 3B:
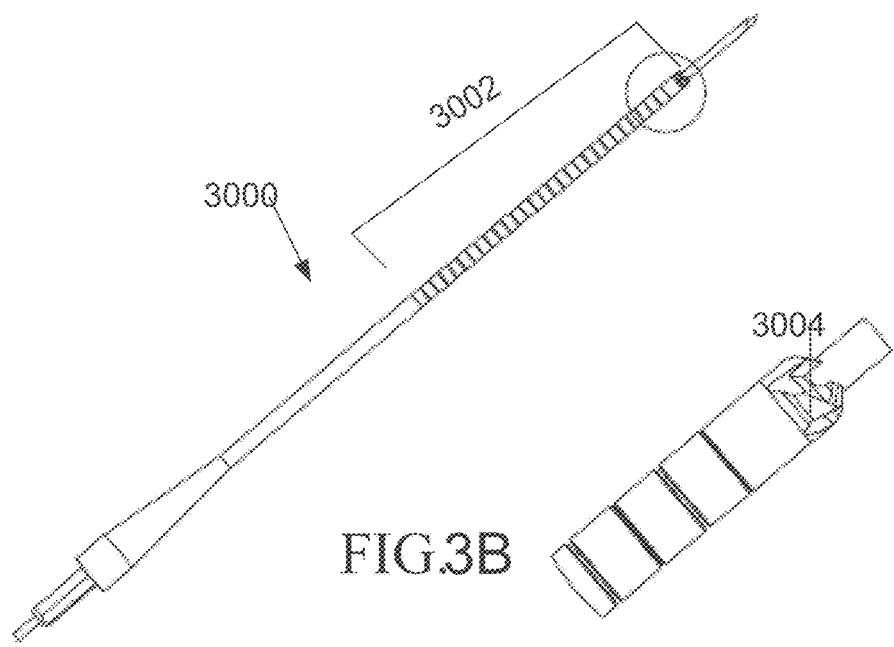

FIGS. 3A-B illustrate a flexible bone tool in accordance with FIGS. 2A1-C in a flexed configuration (3A) and straight configuration (3B), according to some embodiments of the invention.

FIG. 3A shows flexible bone tool 3000 in a flexed configuration, with an enlarged view of a distal portion of the tubular body 3002 comprising cutting head 3004. Tool 3000 is shown threaded over a guide wire 3006, protruding from the distal end of the tool. A holding portion 3008 is configured proximally to the tubular body, and includes a proximal head portion 3010 which is shaped and/or sized to be engaged by a drill and/or other tool.

In some embodiments, tool 3000 is structured to follow a path defined by guide wire 3006, for example being a curved and/or straight path. In some embodiments, tubular body 3002 is configured to bend into a bending radius R. Optionally, bending radius R can be as small as, for example, 50 mm, 30 mm, 20 mm or intermediate, larger or smaller radii.

In some embodiments, the ability of the tubular body to flex to comply with the guide wire curvature is contributed to by the angular orientation between the links 3012. Optionally, during application of rotary motion to the tool (e.g. during drilling), the links would "return" to be aligned with the guide wire path every fraction of the turn which is determined by the angular orientation between the links. In an example, in a 90 degree orientation between adjacent links, the links would "return" to the defined path every quarter of a turn. Optionally, the rotational orientation of the links reduces a discretization effect during rotation, which may be caused due the rigid links, resulting in a non-continuous rotation. Optionally, reducing the angle between the rotationally oriented adjacent links allows for smoother, substantially continuous rotation of the tubular body of the tool.

In some embodiments, an outer diameter 3014 of the tubular body ranges between, for example, 2-10 mm, 4-6.35 mm, 5-20 mm, or intermediate, larger or smaller diameters.

Optionally, the tool is configured to form a bore or to ream an existing bore in a bone to similar diameters.

FIG. 3B shows tool 3000 in a straight configuration, with an enlarged view of a distal portion of the tubular body 3002 comprising cutting head 3004.

Figure 4:
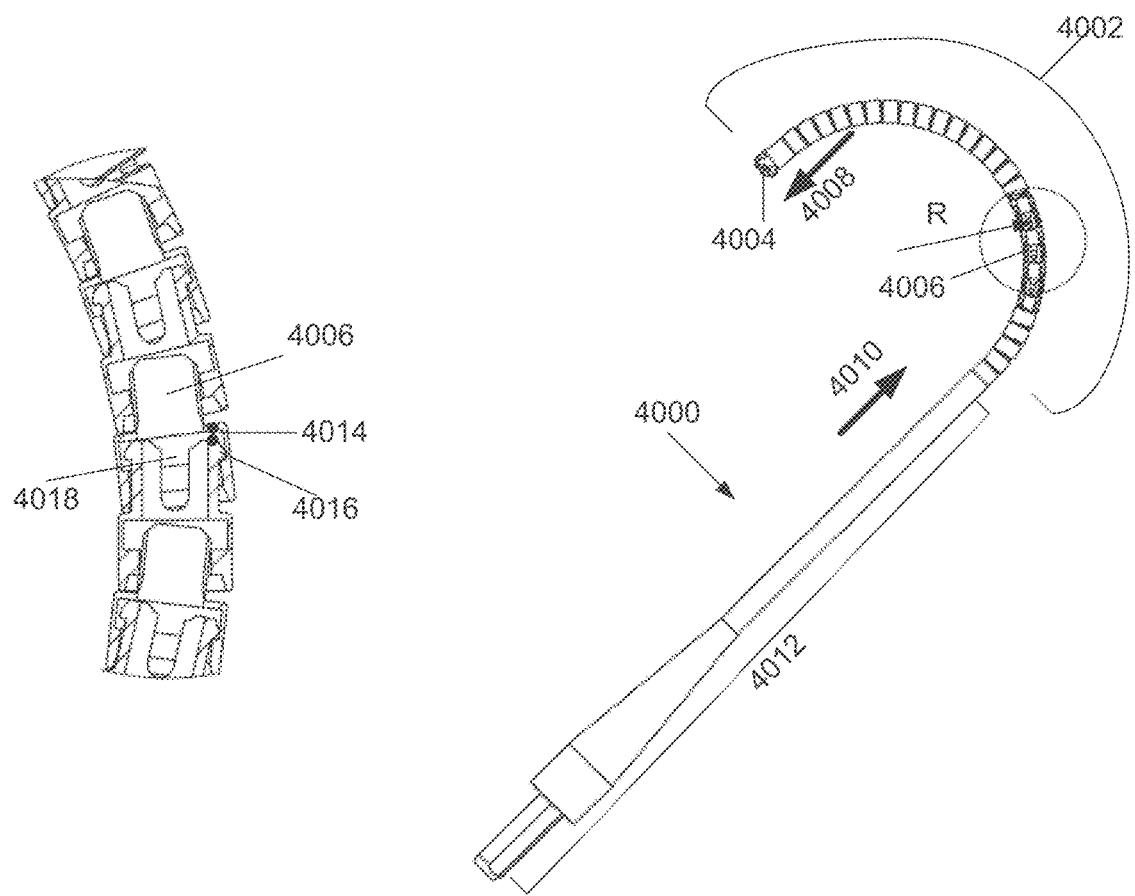
FIG. 4 illustrates a flexible bone tool in accordance with FIGS. 2A1-C bent into a U-curve, according to some embodiments of the invention.

FIG. 4 illustrates a flexible bone tool in accordance with FIGS. 2A1-C bent into a U-curve, according to some embodiments of the invention.

In some embodiments, the tubular body 4002 of the flexible bone tool 4000 is configured to bend in to a small bending radius R, such as 30 mm, 40 mm, 60 mm or intermediate, larger or smaller radii. Optionally, the tubular body is configured to bend into a U-shaped curve, for example such that distal cutting head 4004 faces a direction 4008 which is opposite (e.g. 180 degrees) relative to the axial direction 4010 of a proximal portion 4012 of the tool. A configuration in which the flexible bone is flexed into a U-shape curve may be advantageous in procedures that require accessing the bone through a curved path, for example by going around anatomical structures, for example during spine surgery. In some embodiments, rotating the tool around its axis when the tool is flexed into the U-shaped curve provides for drilling and/or widening a bore in the bone while torque is applied from a substantially opposite direction, from a proximal portion 4012 of the tool, and is transferred by the articulated links 4006 to the distal cutting head 4004.

Links 4006 of tubular body 4002 are shown at a cross section in the enlarged view. In this exemplary flexed configuration, various distances such as distance 4014 can be formed between a radial protrusion such as protrusion 4016 and a wall of the receiving recess 4018. The distances may be as described for example hereinabove in FIG. 2A3 (see distances 2042, 2022).

Figure 5A:
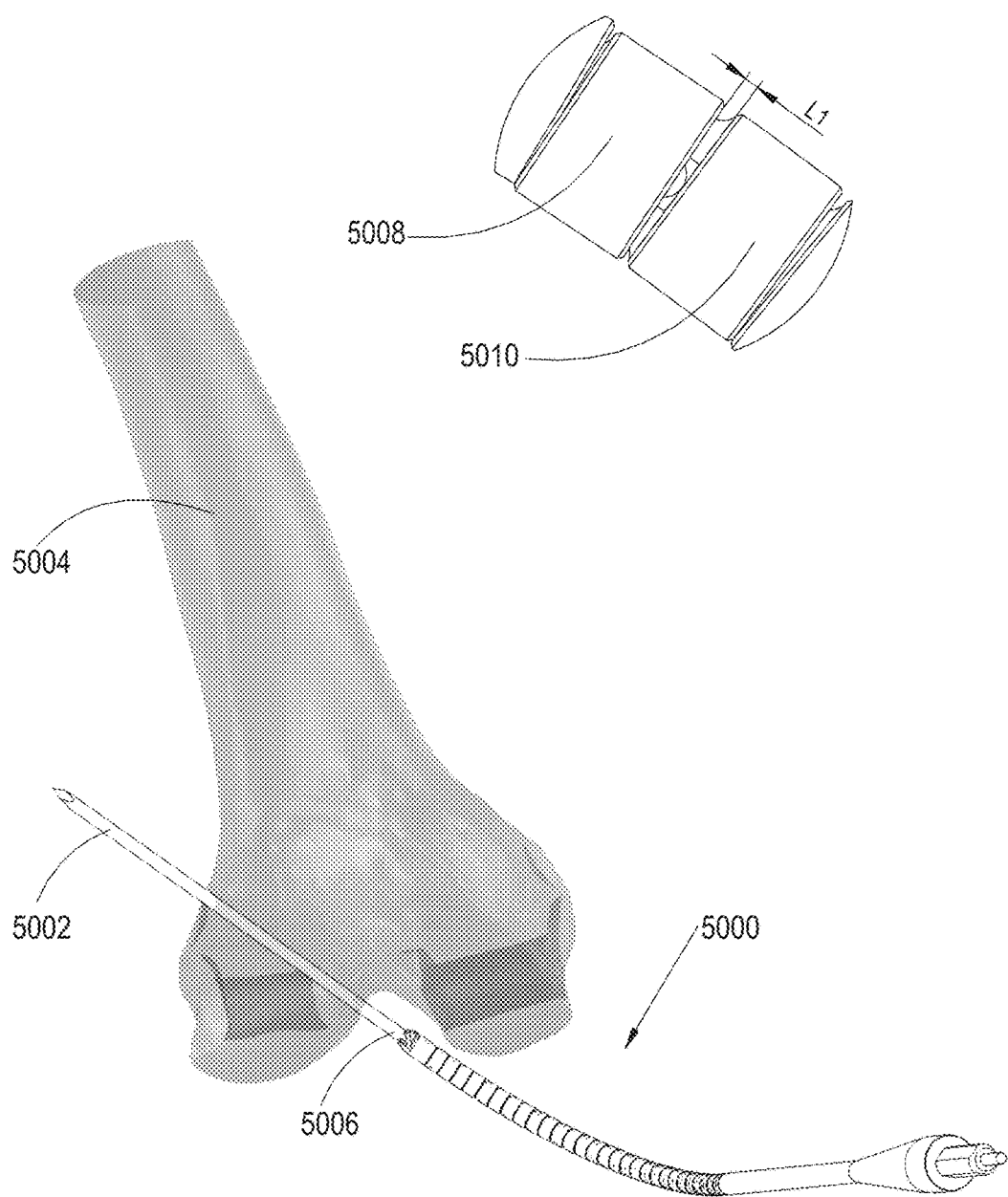
FIGS. 5A-C illustrate advancement of a flexible bone tool in accordance with FIGS. 2A1-C into a bone, according to some embodiments of the invention.
Figure 5B:
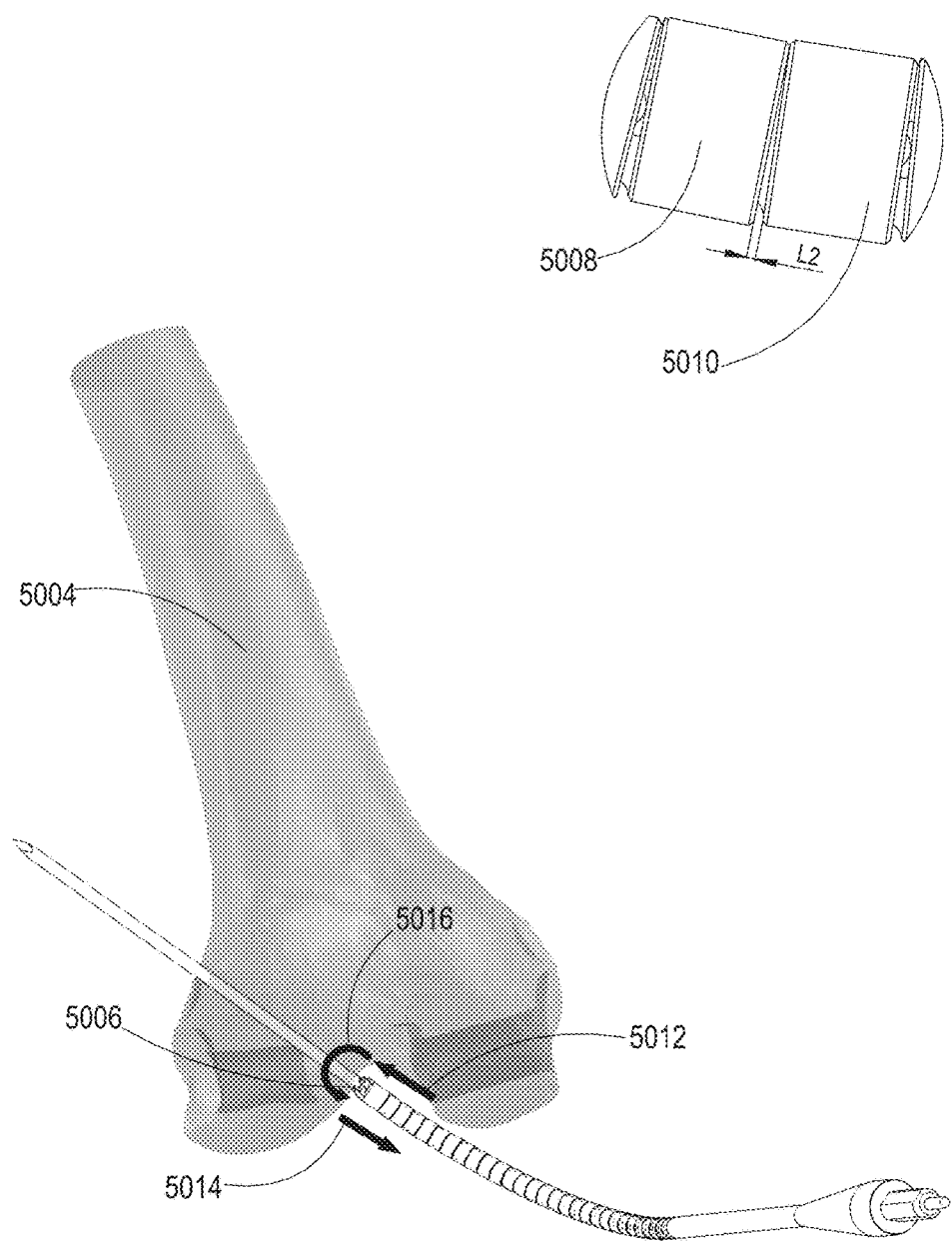
Figure 5C:
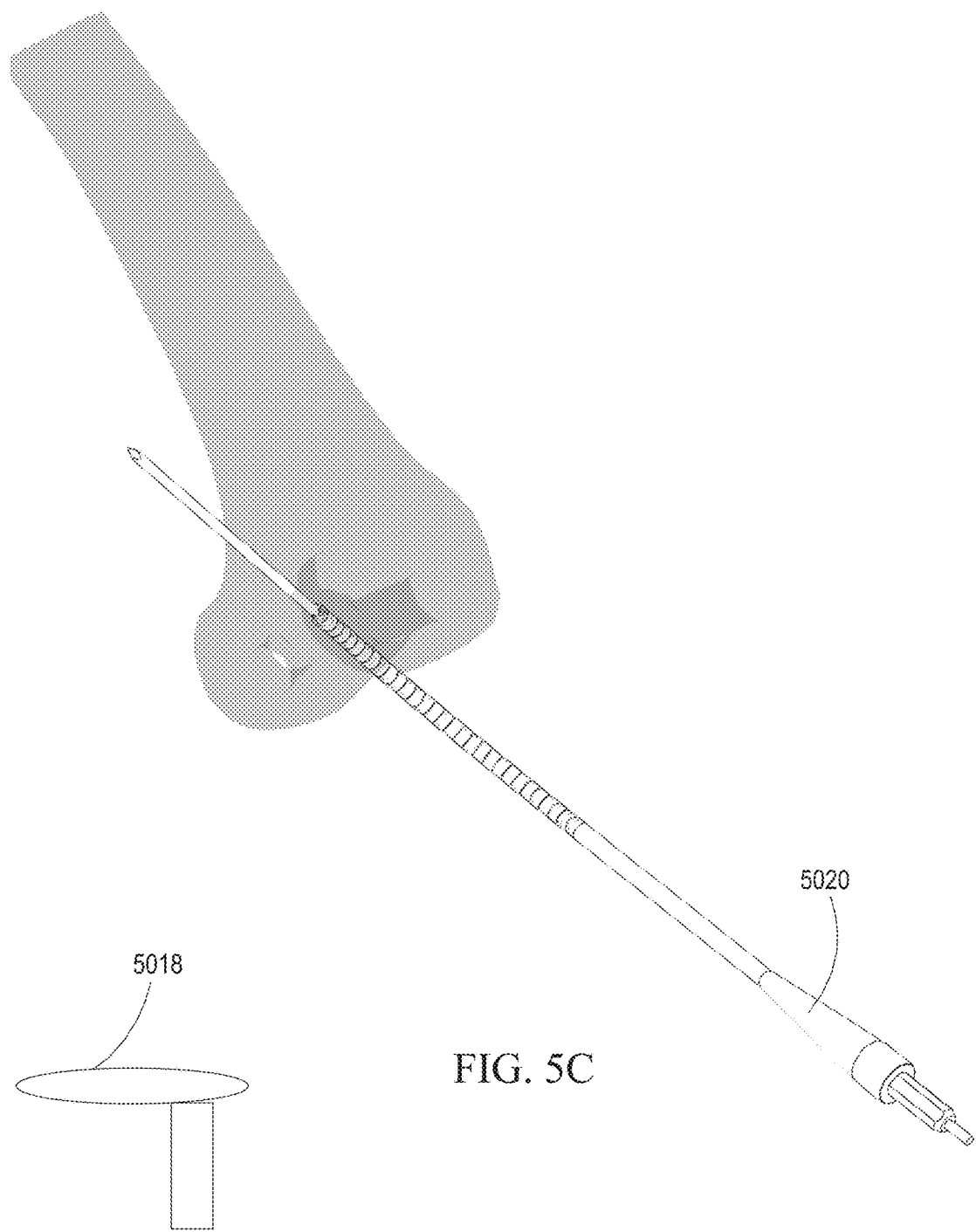

FIGS. 5A-C illustrate advancement of a flexible bone tool in accordance with FIGS. 2A1-C into a bone, according to some embodiments of the invention.

In some embodiments, tool 5000 is advanced over a guide wire 5002 into a bone, such as femoral bone 5004.

In FIG. 5A, the tool is shown in a position in which distal cutting head 5006 has not yet contacted the bone surface. Optionally, as shown in the enlarged view of two links 5008 and 5010, an axial gap extending over a distance L1 exists between at least a portion of the circumferences of the adjoined links. Optionally, the extent of L1 is affected by one or more of: the number of tooth like extensions coupling the links together; a volume within the receiving link that remains unoccupied by the extensions, enabling movement of the extensions inside the receiving recess; the bending radius of the tubular body or a segment thereof; tension force 5012 acting on the tubular body.

In FIG. 5B, the tool is advanced such that cutting head 5006 contacts a surface of bone 5004. Optionally, as force in the direction of advancement is applied from a proximal portion of the device, a resistive compression force 5014 of the bone surface acts in the opposite direction (distal to proximal direction). In response, the axial gap between the links may be reduced to a shorter distance L2. Optionally, a larger circumferential portion of link 5008 comes in contact with a corresponding circumferential portion of link 5010.

In some embodiments, contact with the bone and/or further advancement into the bone axially approximates the links to each other.

In some embodiments, the tool is advanced along a curved path inside the bone. Optionally, the tool follows a path defined by guide wire 5002 as long as the bending radius of the tubular body is compatible with the bending radius of the guide wire. Additionally or alternatively, the tool is advanced along a straight path, as shown for example in FIG. 5C. Optionally, axial gaps between the links decrease until the tubular body straightens out to a linear configuration.

In some embodiments, the tubular body is advanced a certain depth into the bone relative to the surface of the bone, for example a depth ranging between 1 mm to 5 cm. Optionally, the tubular body is advanced to cross through the bone, for example such that cutting head 5006 exits a face of the bone which opposes the face through which the tool was inserted.

In some embodiments, the tool is rotated around its axis to advance it into the bone. Optionally, rotary motion is applied by coupling a drill 5018 to the head of the proximal holding section 5020. In some embodiments, torque 5016 applied onto a proximal end of the tool is transferred by the connected links to a distal end of the tool. In some embodiments, the tool is configured to transfer torque within the range of, for example, 3N*cm to 5 N*cm, such as 3.2, 4.5, 4.8 N*cm or intermediate, higher or lower values.

In some embodiments, for example when the flexible bone tool is used for drilling a bore in the bone, the tubular body may comprise a flexible core, for example made of Nitinol, stainless steel. Optionally, the core is selected to be flexible enough to allow bending of the tubular body, yet rigid enough to support the links during drilling when the tubular body needs to withstand relatively strong forces from the bone tissue in order to penetrate the bone.

FIGS. 6A-H are views of a link in accordance with FIGS. 2A1-C from various directions and cross sections (A-E), and a schematic illustration of an angular orientation between receiving recesses of adjacent links (F-H), according to some embodiments of the invention.

FIG. 6A shows a distal isometric view of a link, according to some embodiments. This exemplary configuration includes two tooth-like extensions 6000 and 6002 in the engaging portion 6010 of the link, each comprising a radially outward protrusion 6004 and 6006 respectively.

Figure 37A:
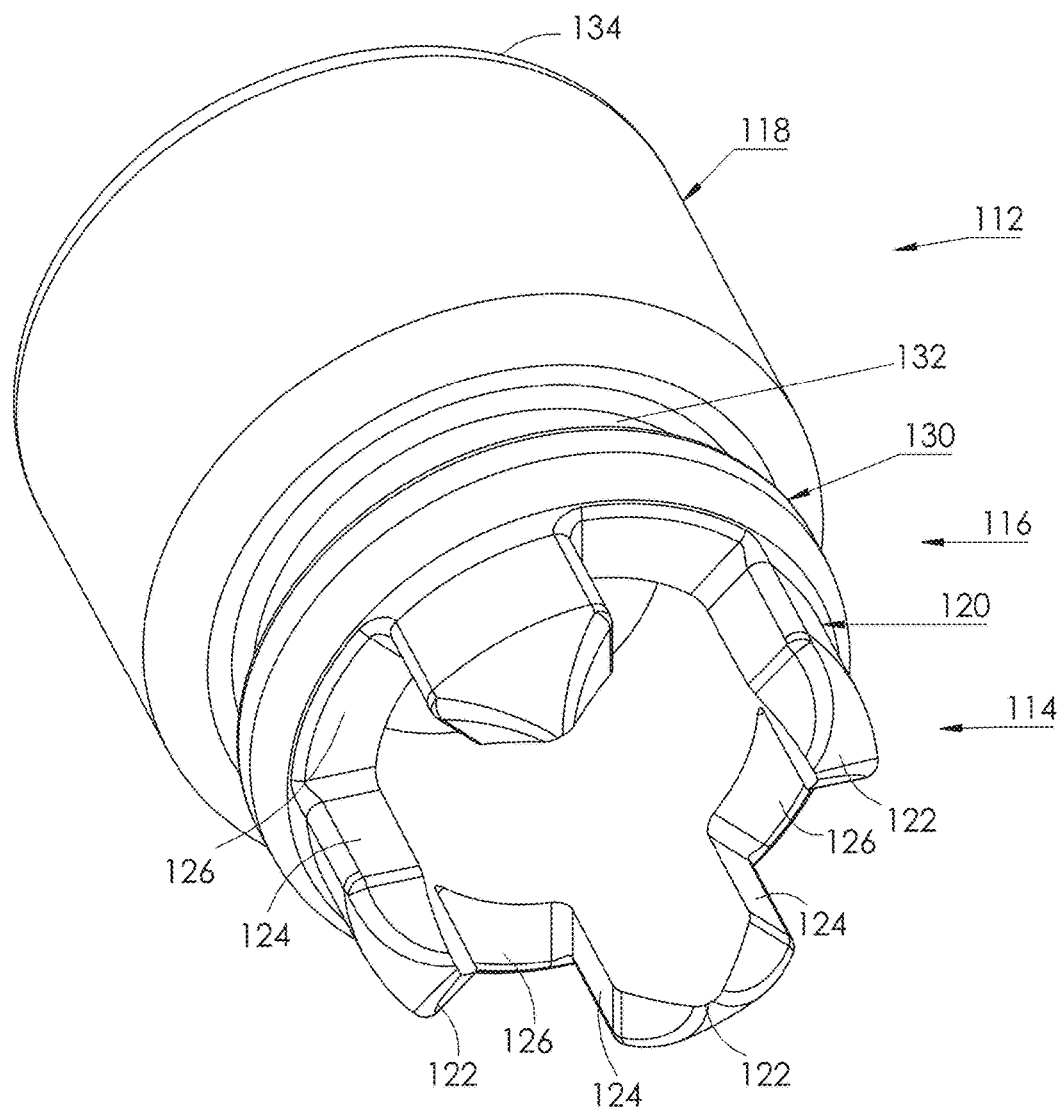
FIGS. 37A-B are simplified pictorial illustrations of a single link of the flexible reamer of FIG. 1, shown from the distal end and from the proximal end respectively.

It is noted that in some embodiments, the radial protrusion may be configured at a more proximal portion of the tooth like extension, and not necessarily at a distal end of the extension as shown herein. Some embodiments may comprise a single, circumferential radial protrusion, for example as shown in FIG. 37A.

In some embodiments, the extensions encompass at least 60%, at least 70%, at least 90% of a notional tubular circumference of the engaging portion. It is noted that some embodiments may include a circumference of a different profile, for example hexagonal, pentagonal or others.

FIG. 6B shows a proximal isomeric view of a link, showing a recess 6008 configured in the receiving portion 6012 of the link in which the engaging portion of a preceding link is received. In some embodiments, recess 6008 defines a cross sectional area smaller than a cross sectional area defined by a distal end portion of the engaging portion of the preceding link which includes the radial protrusions, so that the distal end portion of the engaging portion is compressed radially inwards upon insertion into the receiving portion, until the radial protrusions snap-fit into a larger recess configured at a more distal location of the receiving portion. Recess 6008 may be of various shapes and/or sizes, for example oval, circular, rectangular, and/or other profiles suitable for receiving the engaging portion.

In some embodiments, a contact area formed between a distal circumferential face 6014 (shown in FIG. 6A) of the receiving portion 6012 of a link and a proximal circumferential face 6016 (shown in FIG. 6B) of the subsequent, receiving link is sufficient for accommodating loads acting on the tool during advancement into the bone. Optionally, the engaging faces disperse compression force acting on the tool during contact with the bone and/or opposite tension force acting on the tool. In an example, at least 50%, 75%, 95% or intermediate, larger or smaller percentages of the matching circumferential faces of the links contact each other.

In some cases, the circumferential contact area between the links increases when the distal cutting head of the tool contacts the bone, and the links are axially approximated towards each other. An increased circumferential contact area may provide an advantage during drilling, for example, since the increased contact would contribute to dispersing the load and thereby reduce the load acting on the tooth-like extensions that hold the links together.

In some embodiments, one or more flat faces 6018 of the tooth like extension 6000 are configured to engage one or more flat faces 6020 of recess 6008. Optionally, the matching flat faces limit axial rotation of the links relative to each other to an extent that provides for transmitting torque between the links, for example during drilling.

FIG. 6C shows engaging portion 6010 at a cross section; FIG. 6D shows a side view of the link; FIG. 6E shows receiving portion 6012 at a cross section.

FIGS. 6F-H schematically illustrate relative angular orientations between receiving recesses 6008 and 6018 of adjoined links. In some embodiments, a receiving recess 6008 of a link is configured at a rotated position relative to a receiving recess 6018 of the preceding and/or subsequent link. The recesses may be positioned such that various angles can be formed between them, for example between the long axes of the recesses. In the exemplary configurations shown herein, FIG. 6F shows a perpendicular orientation between the recesses, FIG. 6G shows a 30 degree orientation, FIG. 6H shows a 60 degree orientation between the recesses.

Figure 7B:
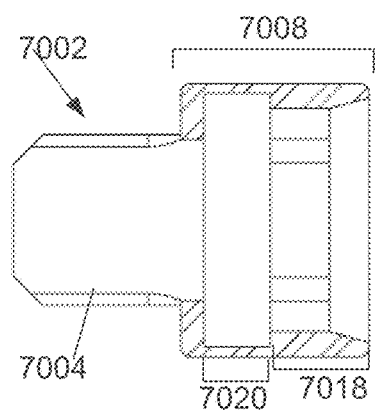
FIGS. 7A-C are cross section views of a link (7A), a receiving subsequent link (7B), rotationally oriented relative to the link of 7A, and the links coupled to each other (7C), according to some embodiments of the invention.
Figure 7A:
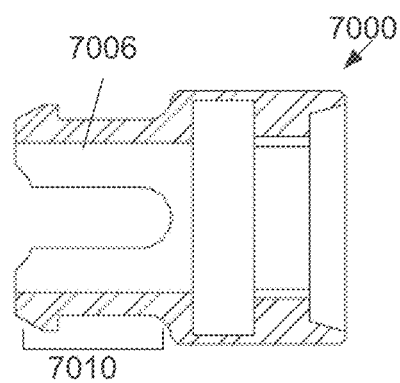
Figure 7C:
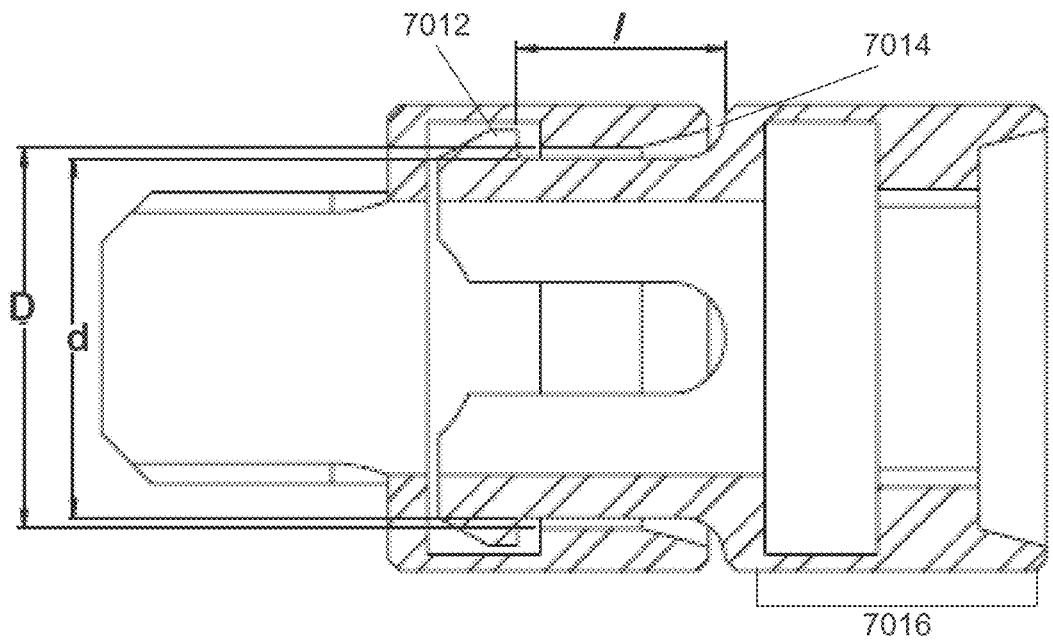

FIGS. 7A-C are cross section views of a link (7A), a receiving subsequent link (7B), rotationally oriented relative to the link of 7A, and the links coupled to each other (7C), according to some embodiments of the invention.

In the exemplary cross sections of FIGS. 7A-B, it can be observed that the link 7000 and a subsequent, receiving link 7002 are perpendicularly oriented relative to each other. The tooth like-extensions 7004 of link 7002, at a cross section, are shown to extend on a plane which is perpendicular to the plane of the cross section of tooth like extensions 7006 of link 7000.

In some embodiments, as shown for example in FIG. 7B, a receiving portion 7008 of the link comprises one or more internal recesses in which an engaging portion 7010 of link 7000 is received. In some embodiments, the recess comprises a proximal portion 7018 defining one or more cross sectional areas that are smaller than a cross sectional area of a more distal portion 7020 of the recess, so that when tooth like extensions 7006 are advanced into the recess, they extend outwardly within the wider portion of the recess and are restrained from moving back in a proximal direction by the narrower proximal portion of the recess.

FIG. 7C shows the assembled links at a cross section.

In some embodiments, one or more dimensions of a link are selected to provide for a certain bending radii range of a tubular body comprising a plurality of links. Optionally, the extent of the bending radius is determined by link dimensions such as: "l", a length measured along a tooth like extension 7006, between radial protrusion 7012 and a distal face 7014 of a receiving portion 7016 of link 7000; "d", a diameter defined by tooth-like extensions 7006 without their radial protrusions; and "D" a diameter of proximal portion 7018 of the recess of receiving link 7002. In some embodiments, a more flexible tubular body which is configured to bend into smaller bending radii can be provided by one or more of: increasing the "l" dimension; decreasing the "d" dimension; increasing the "D" dimension. Optionally, selecting the link dimensions for example as described would result in a larger space of proximal portion 7018 of the recess remaining unoccupied by extensions 7006, so that during bending the extensions will be more free to move around in the recess and allow a higher degree of flexion of the tubular body.

Figure 8A:
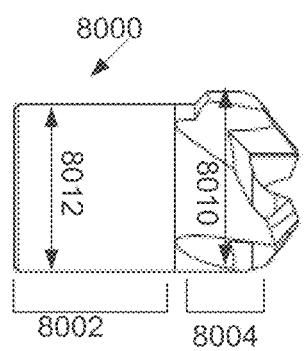
FIGS. 8A-G illustrate a distal cutting head configured to engage a flexible bone tool in accordance FIGS. 2A1-C, according to some embodiments of the invention.
Figure 8B:
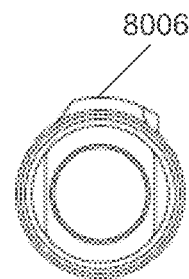
Figure 8C:
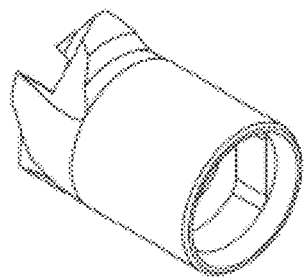
Figure 8D:
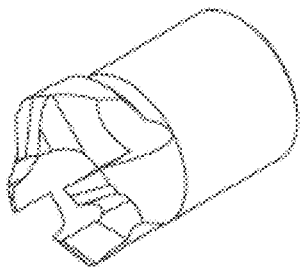
Figure 8E:
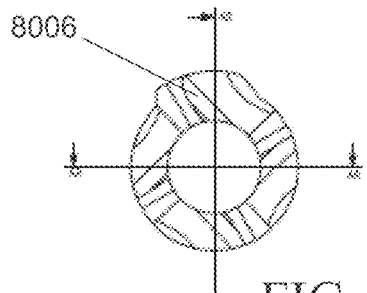
Figure 8F:
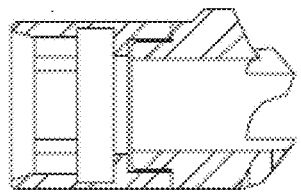
Figure 8G:
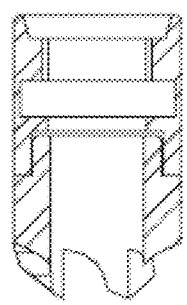
Figure 9A:
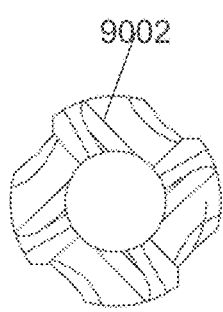
FIGS. 9A-E illustrate another configuration of a distal cutting head configured to engage a flexible bone tool in accordance with FIGS. 2A1-C, according to some embodiments of the invention.
Figure 9B:
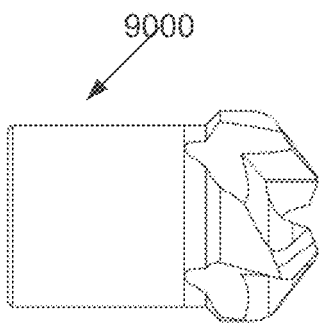
Figure 9C:
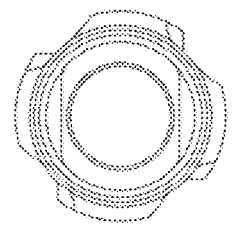
Figure 9D:
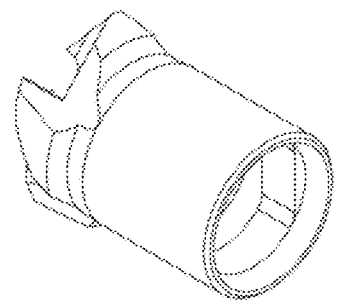
Figure 9E:
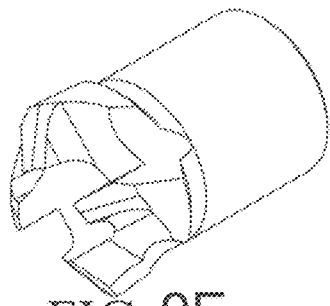

FIGS. 8A-G illustrate a distal cutting head configured to engage a flexible bone tool in accordance with FIGS. 2A1-C, according to some embodiments of the invention. FIG. 8A shows a side view of the cutting head. FIGS. 8B and 8E are transverse cross sections of the cutting head. FIGS. 8C and 8D are a proximal isometric view and a distal isometric view respectively. FIG. 8F is a longitudinal cross section of the cutting head.

In some embodiments, cutting head 8000 comprises a proximal receiving portion 8002 structured to receive an engaging portion of a preceding link, for example having a structure similar to receiving portion 7008 described hereinabove. Optionally, receiving portion 8002 comprises an internal recess for example as described hereinabove. In some embodiments, cutting head 8000 comprises a distal cutting portion 8004, comprising one or more cutting edges 8006 for penetrating the bone and/or for enlarging an existing bore in the bone.

In some embodiments, a cross sectional area of cutting portion 8004 is larger than a cross sectional area of receiving portion 8002 (and optionally of the rest of the tubular body of the tool). In an example, a maximal diameter 8010 of cutting portion 8004 is at least 5%, 10%, 20%, 40% or intermediate, larger or smaller percentages larger than a diameter 8012 of receiving portion 8002.

FIGS. 9A-E illustrate another configuration of a distal cutting head configured to engage a flexible bone tool in accordance with FIGS.2A1-C, according to some embodiments of the invention. In this example, cutting head 9000 comprises 4 cutting edges 9002. Other embodiments may include a different number of cutting edges, such as 2, 3, 4, 7, 10 or intermediate, larger or smaller amount. Optionally, the number of cutting edges of the cutting head is selected according to one or more parameters such as a shape and/or size of the bone, the amount of force that needs to be applied during drilling, bone density.

Figure 10:
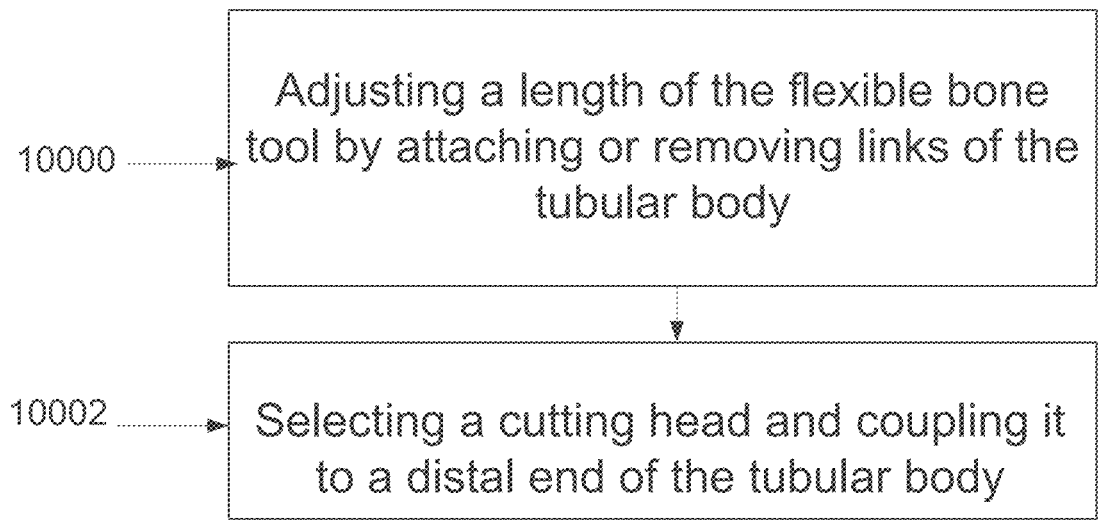
FIG. 10 is a flowchart of a method for adjusting a flexible bone tool, according to some embodiments of the invention.

FIG. 10 is a flowchart of a method for adjusting a flexible bone tool, according to some embodiments of the invention.

In some embodiments, the flexible bone tool is adjustable. In some embodiments, the tubular body of the tool is adjustable in length, for example by attaching or removing one or more links (10000). In some embodiments, a cutting head is selected out of a plurality of cutting heads having different structures, and is attached to the distal end of the tubular body (10002).

In some embodiments, a user such as a physician selects a length and/or cutting head suitable for a certain procedure. In an example, the user increases the length of the tubular body to enable to tool to reach more distant bone targets and/or to enable the tool to go around anatomical structures (e.g. other bones, muscles, tendons, blood vessels, etc). In another example, the user selects a cutting head suitable for drilling a bore in the bone, or a cutting head suitable for the purpose of widening an existing bore in a bone.

In some embodiments, adjustment of the flexible bone tool is performed prior to the procedure. Additionally or alternatively, adjustment is performed during the procedure, for example if a need for a longer or shorter tool rises. In such a case, the tool can be retracted from the body, adjusted, and reinserted into the body. Optionally, adjustment is performed in the surgery room.

In some embodiments, a proximal portion of the tool is adjustable. Optionally, a structure of the proximal head is selected to engage a surgical tool, such as a drill, reamer, screw driver, and/or other tools. Optionally, the proximal head is adapted to connect to a tool suitable for applying rotary motion to the flexible bone tool. For example, the proximal head may have a hexagonal profile, a squared profile, a round profile, and/or any other profile shaped and sized to be engaged by the tool. In some embodiments, dimensions of the proximal portion (such as an axial length and/or diameter) are selected according to the need.

In some embodiments, a kit is provided. Optionally, the kit comprises a plurality of separate links; a plurality of cutting heads having different structures and/or sizes; a flexible bone tool comprising a proximal holding section and a tubular body of an initial base length (for example a length ranging between 30-120 mm, such as 40 mm, 60 mm, 100 mm or intermediate, longer or shorter tubular body).

In some embodiments, the kit comprises a device configured for separating and/or attaching the links. Optionally, the device is configured to apply a pull out force on the links which is strong enough to separate the snap-fit connection. In some embodiments, the adjustment device is configured to apply pressure for example in a radially inwards direction on the tooth-like extensions in order separate links or to attach links together.

Additionally or alternatively, attachment and/or detachment of links is performed manually, for example by a user.

Figure 11:
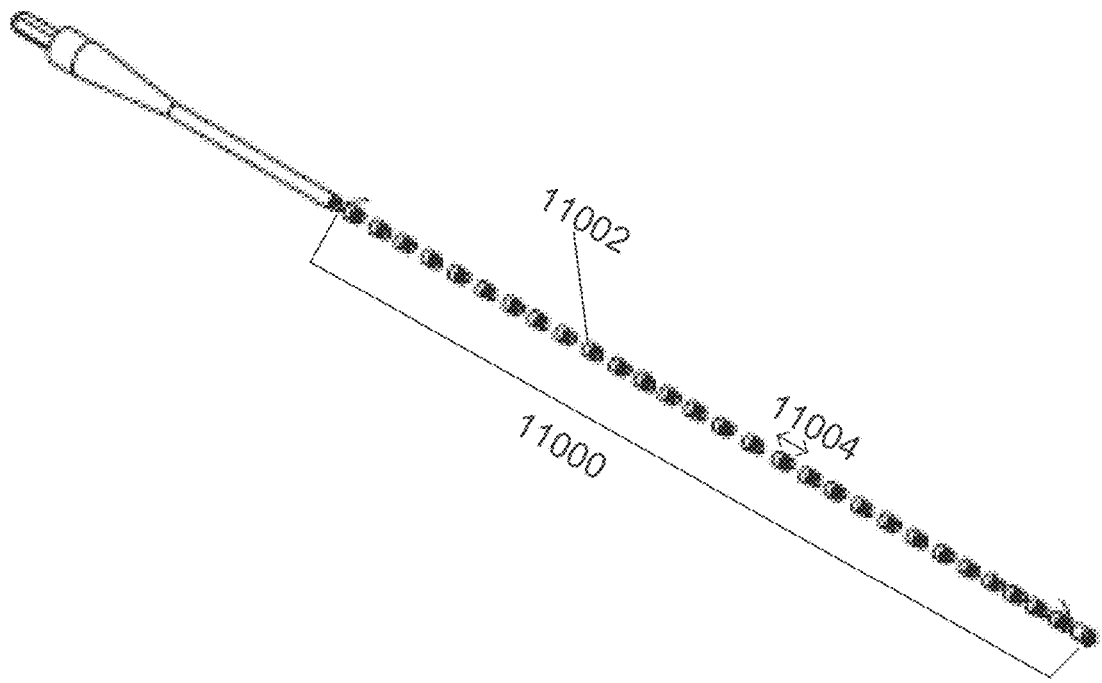
FIG. 11 schematically illustrates a flexible bone tool adjustable in length, according to some embodiments of the invention.

FIG. 11 schematically illustrates a flexible bone tool adjustable in length, according to some embodiments of the invention. In some embodiments, the number of links 11002 of tubular body 11000 can be selected according to the need. In an example, an axial length 11004 of a link ranges between, for example, 0.5 mm to 6 mm, such as 2 mm, 3 mm, 5 mm or intermediate, longer or shorter lengths. Optionally, the tubular body 11000 comprises between 5-70 links, 20-40 links, 3-15 links, or intermediate, larger or smaller number of links.

In some embodiments, one or more links can be added to or removed from a distal end 11006 of the tubular body. Additionally or alternatively, the links of the tubular body can be separated at an intermediate portion or a more proximal portion of the tubular body, and one or more links can be added to either of the separated segments or removed from them before reattaching the separated segments.

FIG. 12 is an exemplary link structure of the flexible bone tool, comprising radial protrusions for engaging one or more externally extending recesses of a subsequent link, according to some embodiments of the invention.

In some embodiments, one or more recesses 12000 of a receiving portion of a link which are engaged by the radial protrusions 12002 and 12004 of the tooth-like extensions 12006 and 12008 extend beyond an outer wall 12010 of the link, such that the radial protrusions are not contained internally within the link but rather extend in the radial direction to or beyond outer wall 12010.

In some embodiments, the one or more recesses 12000 extend at least along a circumferential portion of outer wall 12010, such that the radial protrusions 12002 and 12004 that are received within the recesses can be viewed from outside the tubular body of the flexible bone tool.

In some embodiments, the one or more recesses of a receiving, subsequent link are angularly rotated relative to the one or more recesses of the preceding link, for example oriented at an angle ranging between 5-180 degrees such as 30 degrees, 60 degrees, 90 degrees, 120 degrees, 180 degrees or intermediate, larger or smaller angles.

In some embodiments, the externally-extending recesses provide visual feedback for a user such as a physician that the links are properly connected to each other. This may be especially advantageous when increasing a length of the tool, outside the body, by coupling one or more additional links to the tubular body.

Figure 13A:
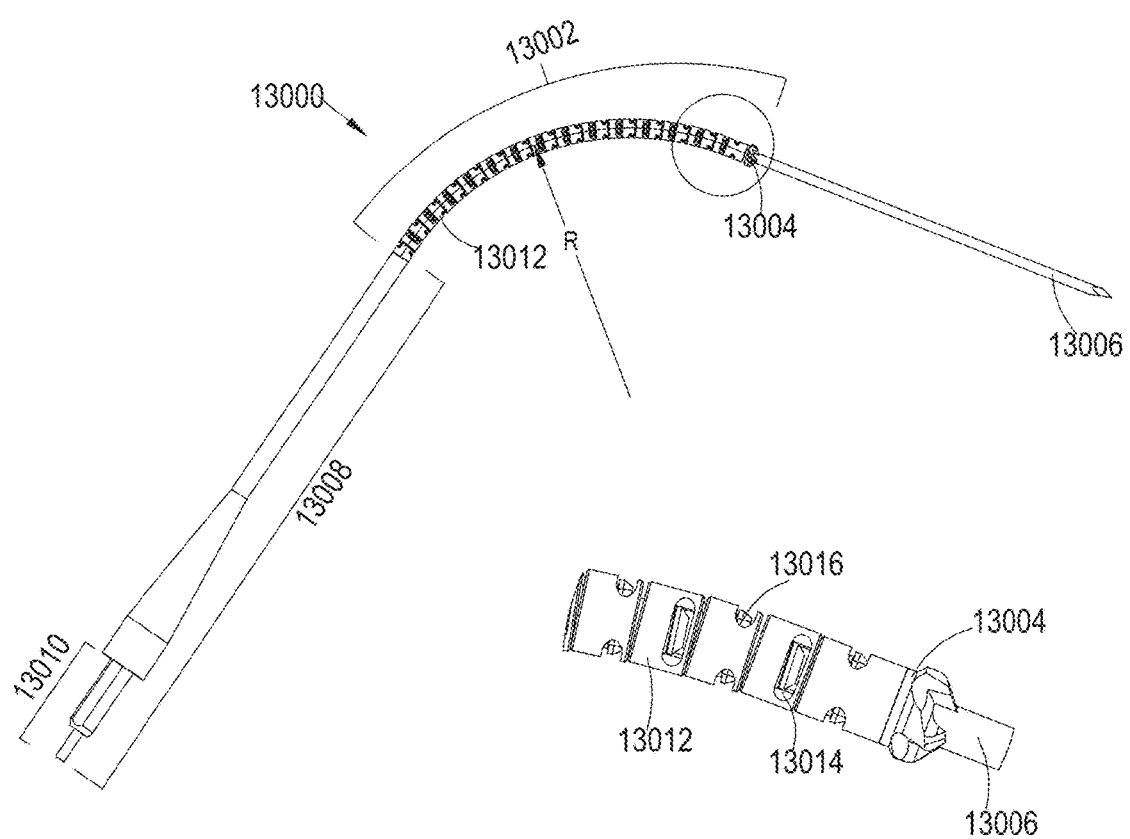
FIGS. 13A-B illustrate a flexible bone tool in accordance with FIG. 12 in a flexed configuration (13A) and straight configuration (13B), according to some embodiments of the invention.
Figure 13B:
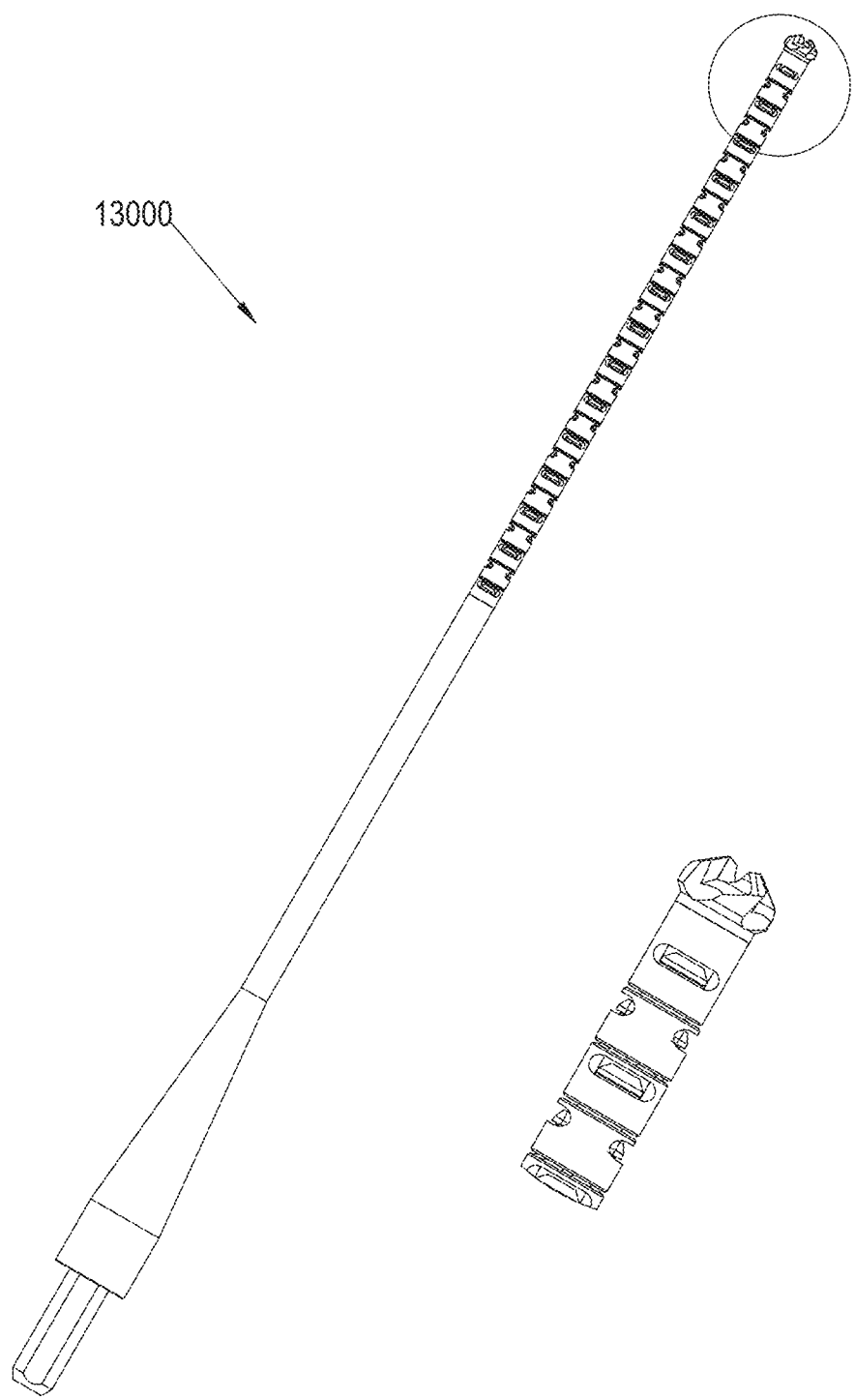

FIGS. 13A-B illustrate a flexible bone tool in accordance with FIG. 12 in a flexed configuration (13A) and straight configuration (13B), according to some embodiments of the invention. FIGS. 13A-B generally correspond to the described above in FIGS. 3A-B and the description of corresponding parts will not be repeated. It is noted that in a tubular body comprising the exemplary link structure of FIG. 12, the externally extending recess 13014 and the radial protrusion 13016 can be observed from outside the tubular body. In the exemplary configuration shown herein, recesses of adjacent links are rotationally oriented at a 90 degree angle relative to each other.

Figure 14:
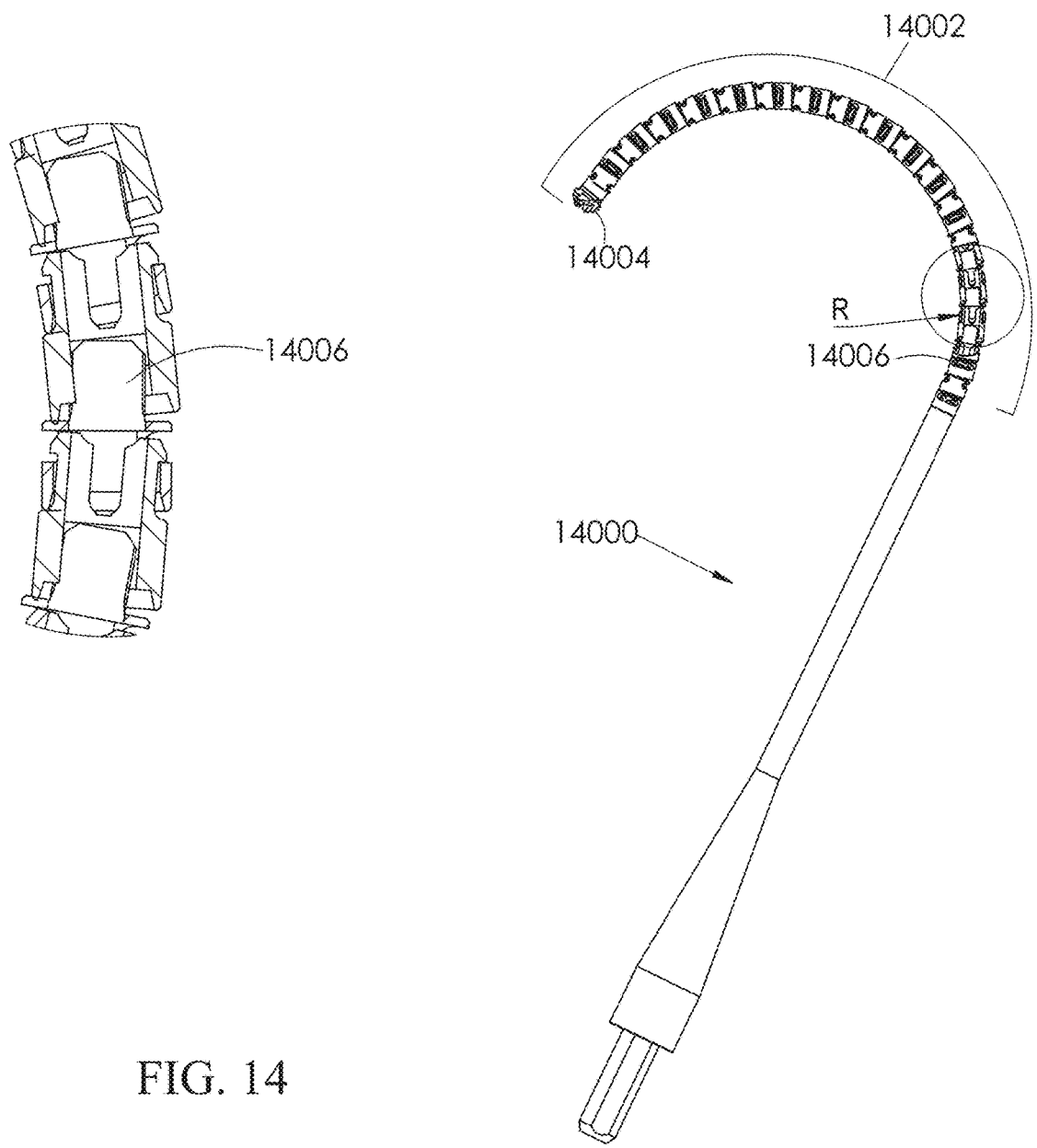
FIG. 14 illustrates a flexible bone tool in accordance with FIG. 12 bent into a U-curve, according to some embodiments of the invention.

FIG. 14 illustrates a flexible bone tool in accordance with FIG. 12 bent into a U-curve, according to some embodiments of the invention. FIG. 14 generally corresponds to the described above in FIG. 4 and the description of corresponding parts will not be repeated. In this figure, the externally extending recesses and the radial protrusions that are aligned with or project radially outwardly from the tubular body are shown.

Figure 15A:
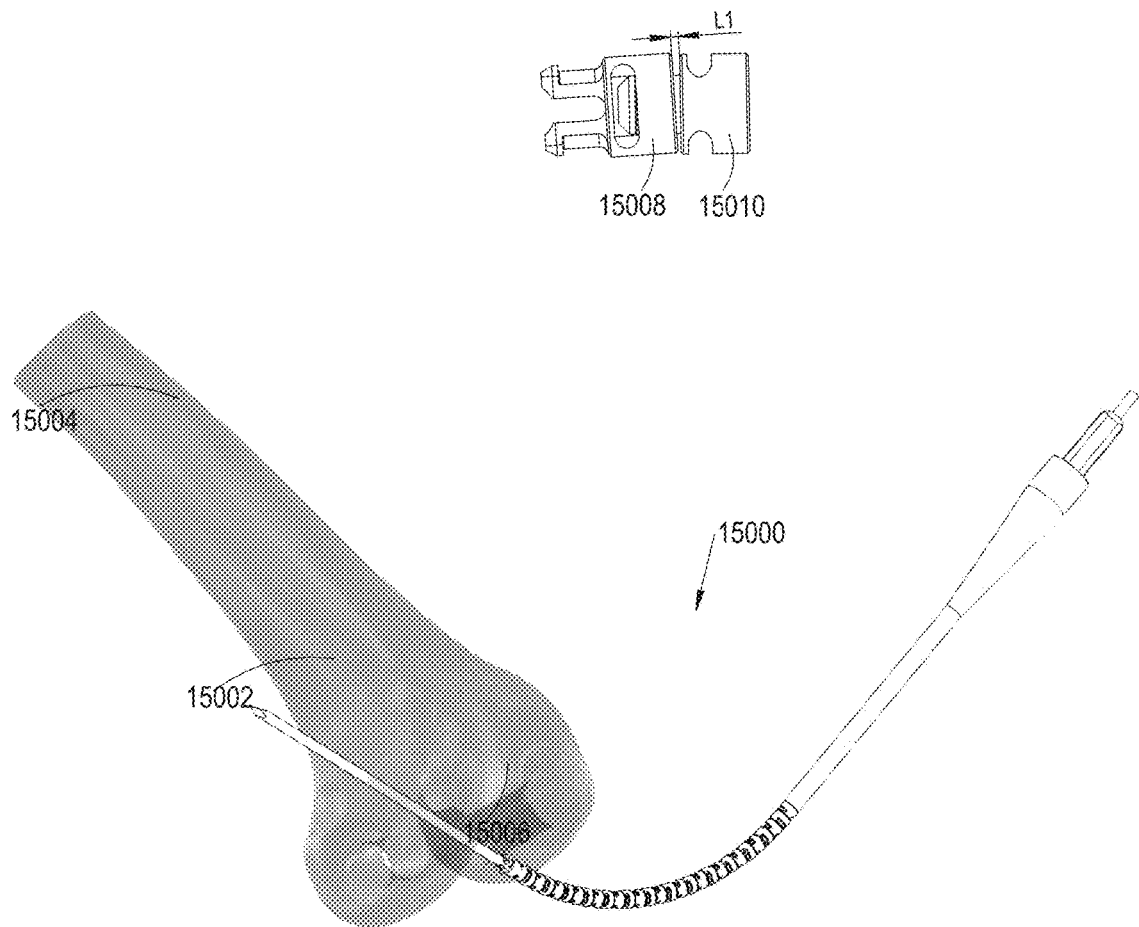
FIGS. 15A-B illustrate advancement of a flexible bone tool in accordance with FIG. 12 into a bone, according to some embodiments of the invention.
Figure 15B:
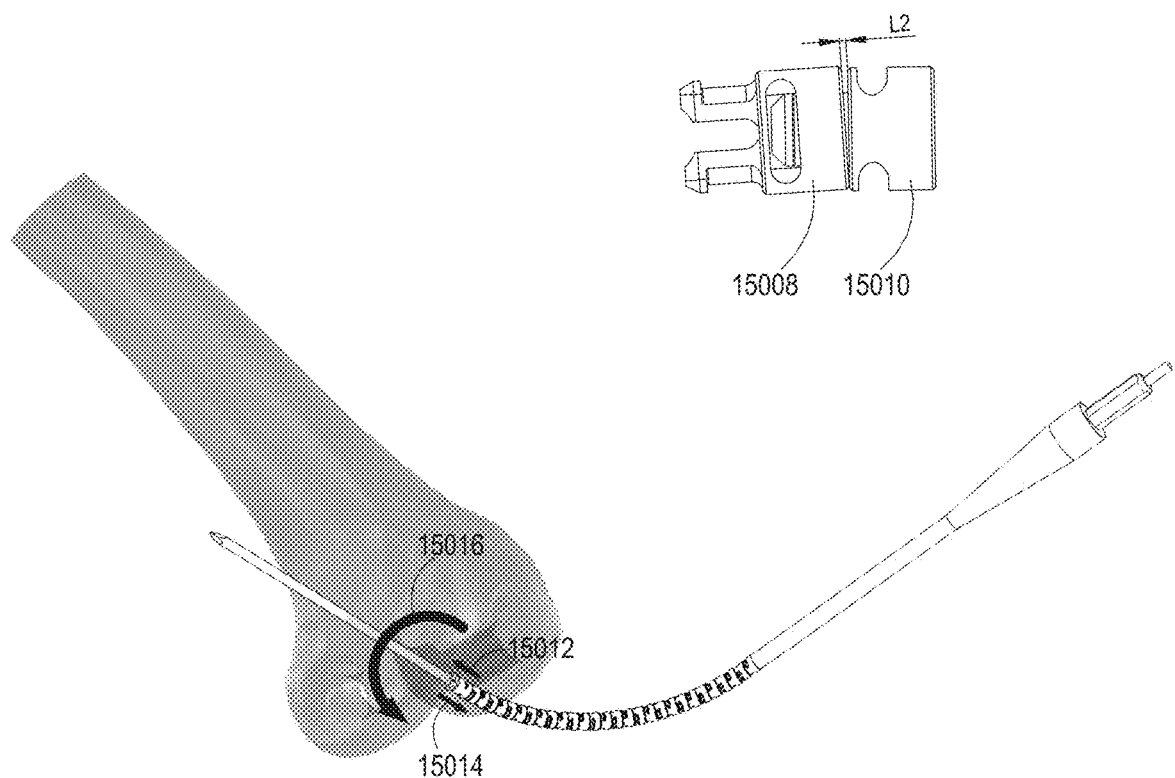
Figure 16A:
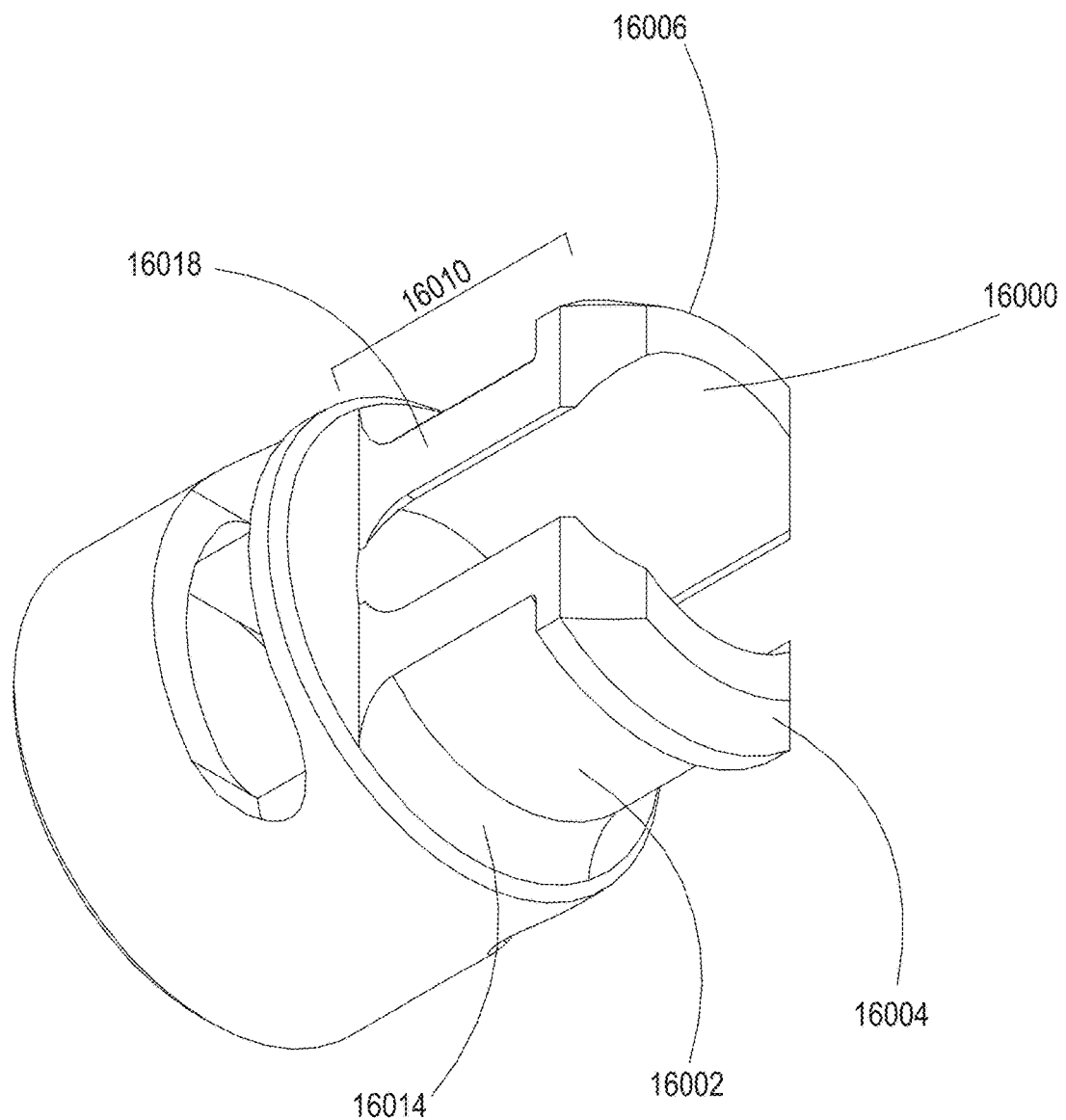
FIGS. 16A-E are views of a link in accordance with FIG. 12 from various directions and cross sections, according to some embodiments of the invention.
Figure 16B:
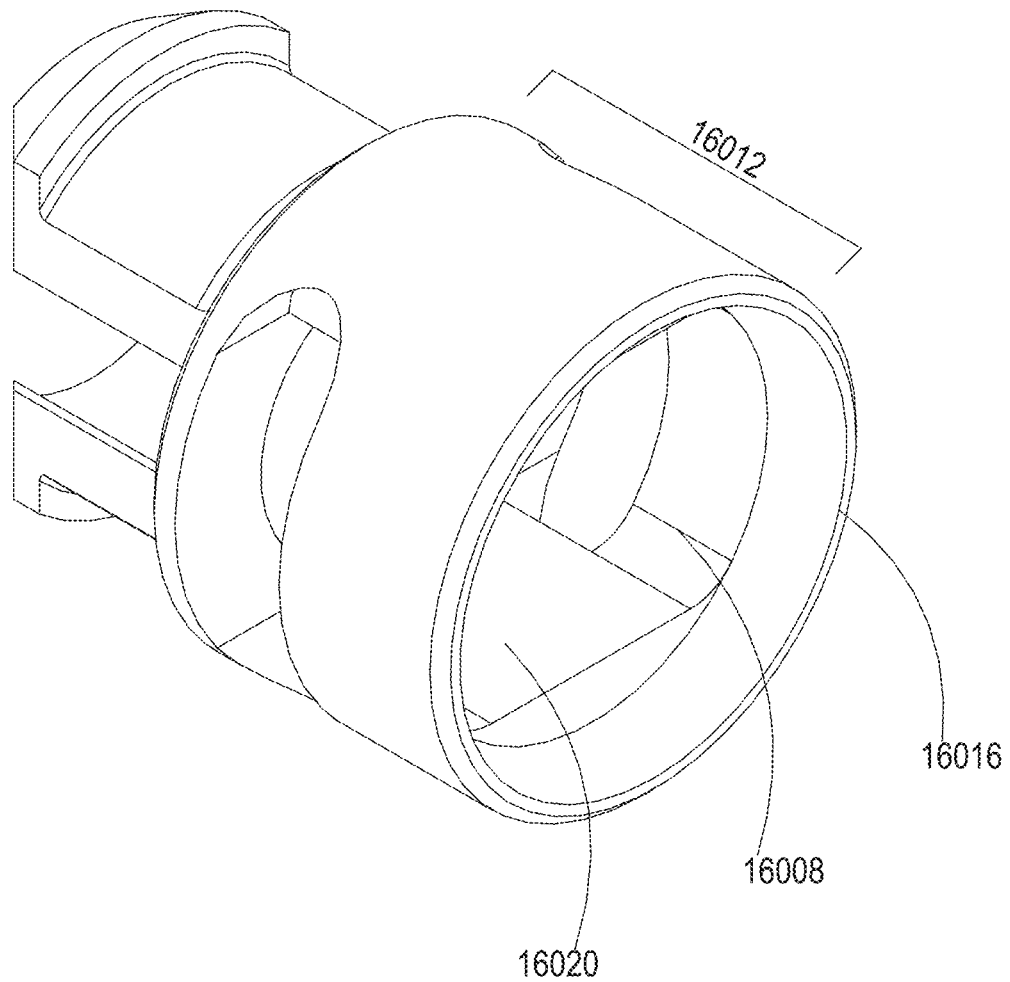
Figure 16C:
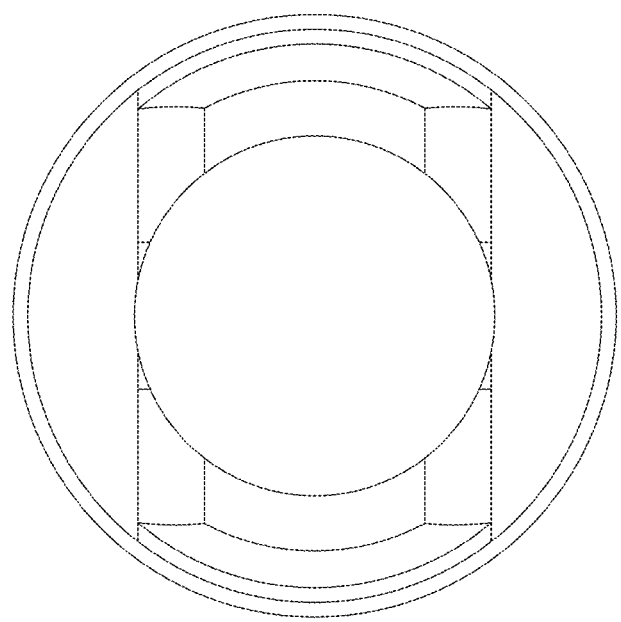
Figure 16D:
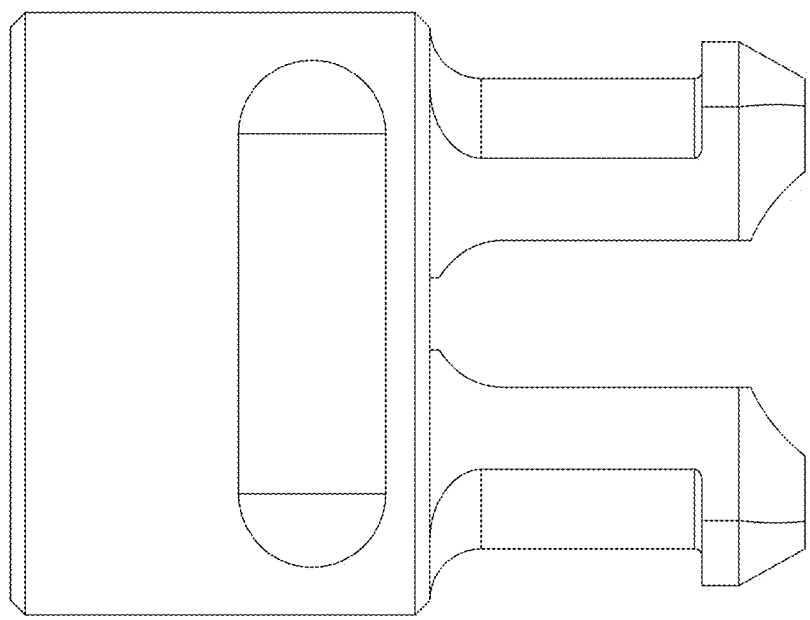
Figure 16E:
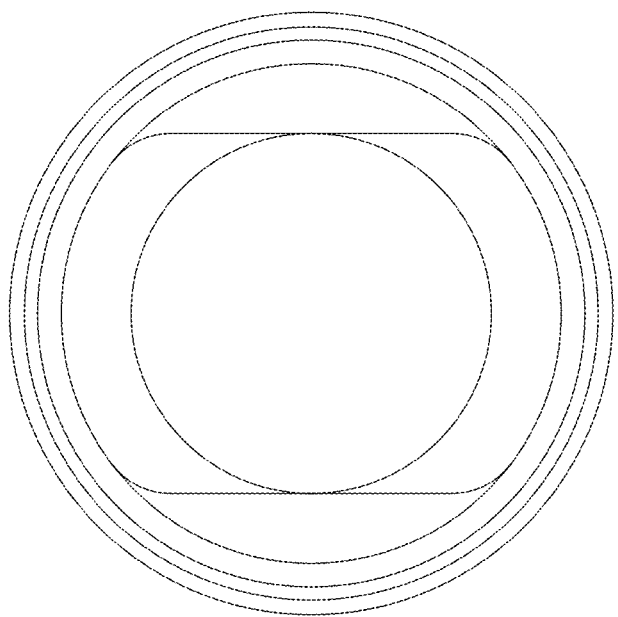

FIGS. 15A-B illustrate advancement of a flexible bone tool in accordance with FIG. 12 into a bone, according to some embodiments of the invention. FIGS. 15A-B generally corresponds to the described above in FIGS. 5A-B and the description of corresponding parts will not be repeated.

FIGS. 16A-E are views of a link in accordance with FIG. 12 from various directions and cross sections, according to some embodiments of the invention. FIGS. 16A-E generally corresponds to the described above in FIGS. 6A-E and the description of corresponding parts will not be repeated.

Figure 17A:
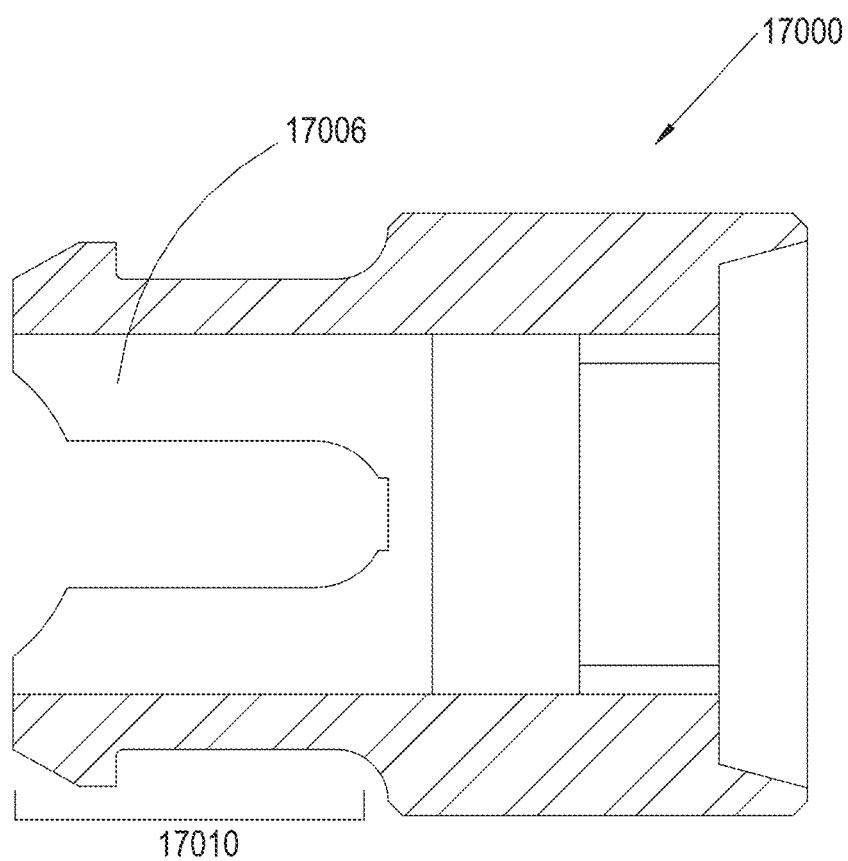
FIGS. 17A-C are cross section views of a link (17A), a receiving subsequent link (17B), rotationally oriented relative to the link of 17A, and the links coupled to each other (17C), according to some embodiments of the invention.
Figure 17B:
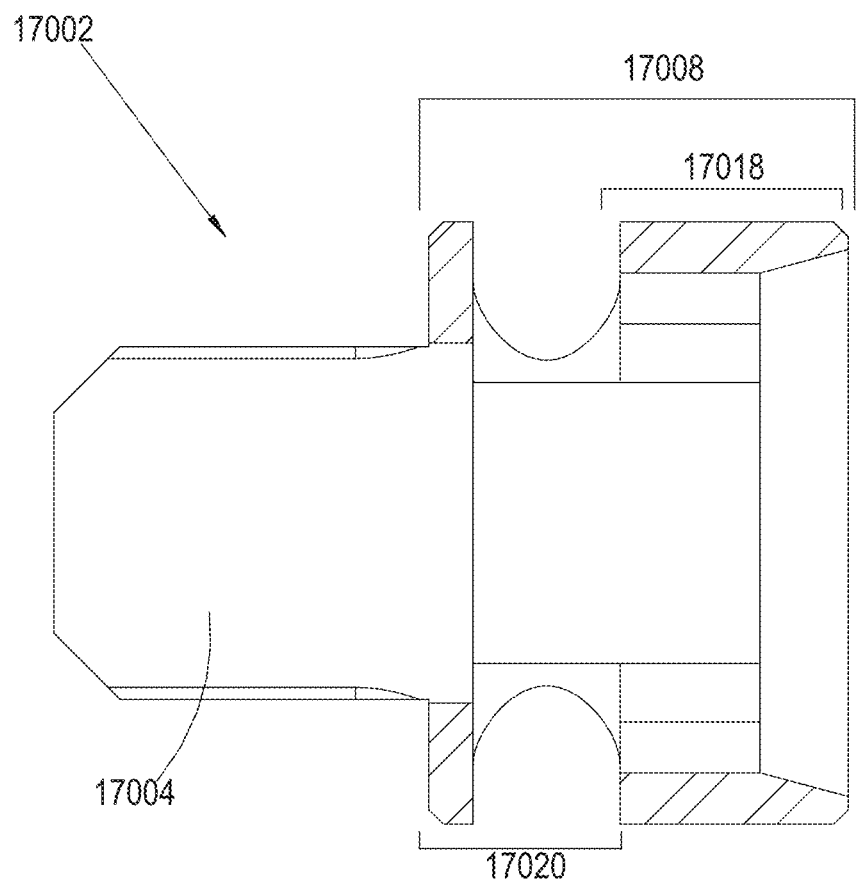
Figure 17C:
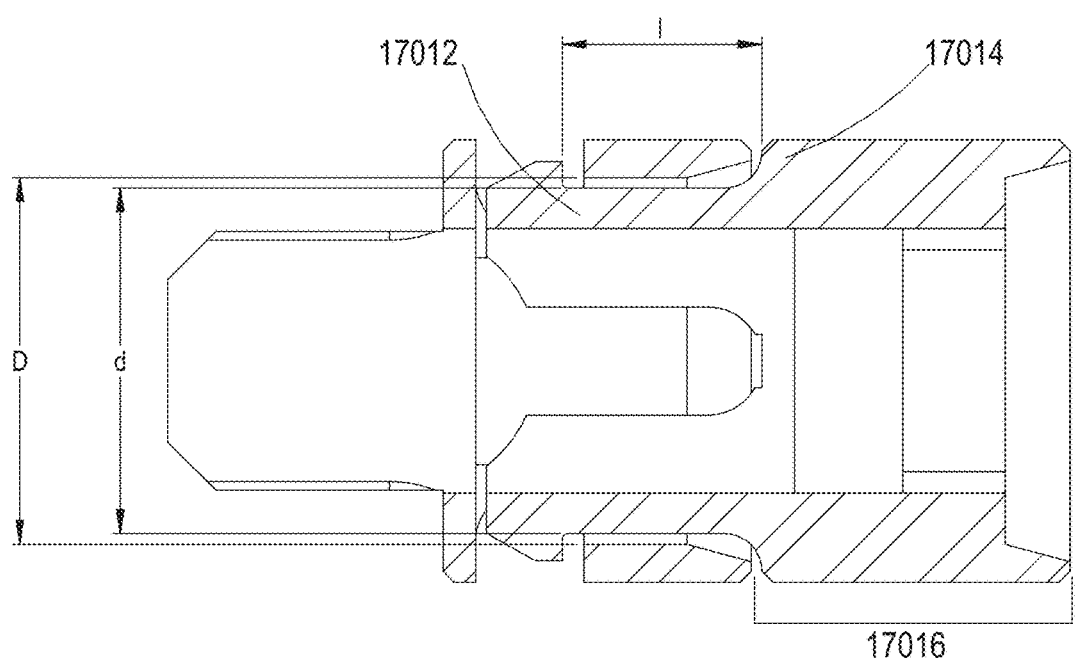
Figure 18A:
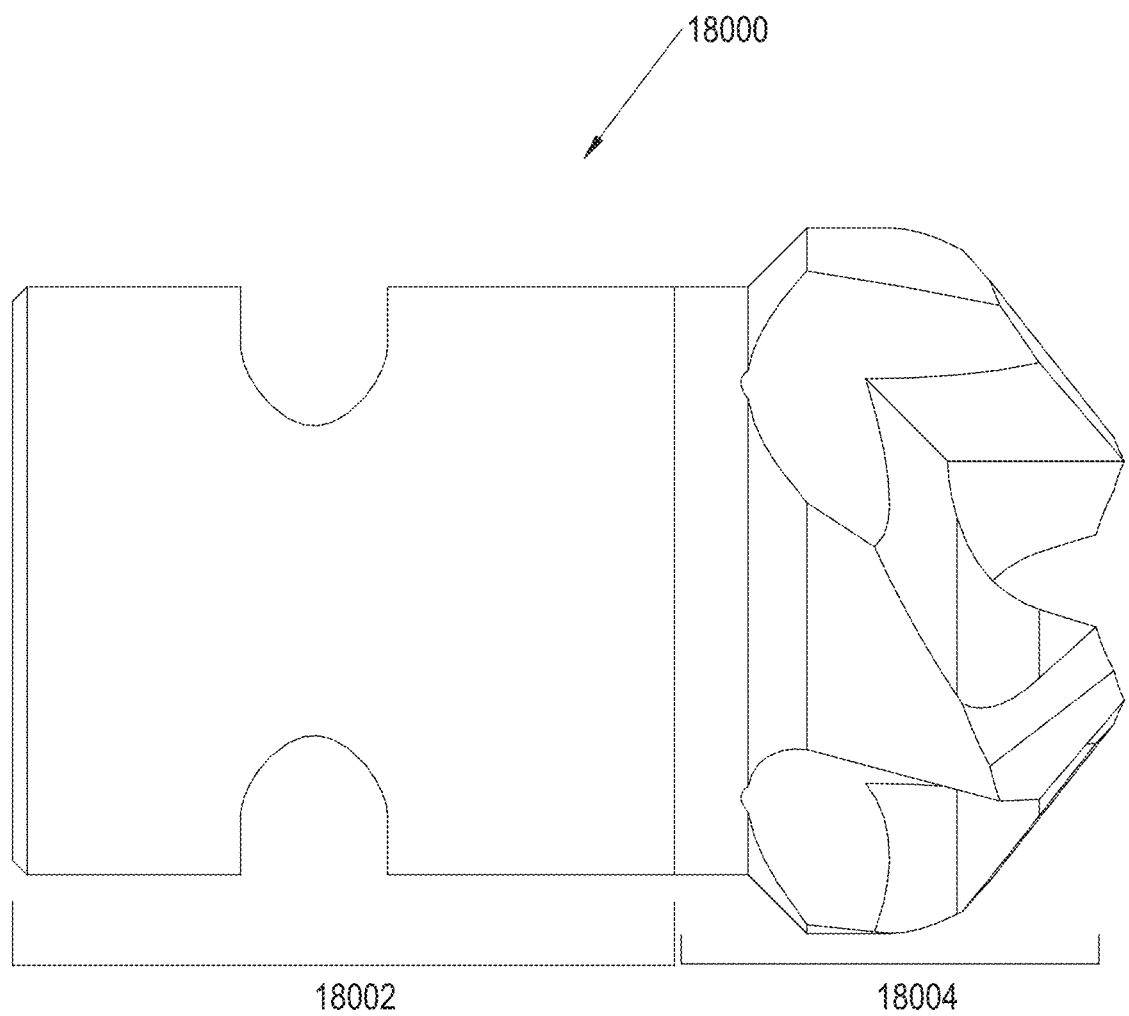
FIGS. 18A-G illustrate a distal cutting head configured to engage a flexible bone tool in accordance with FIG. 12, according to some embodiments of the invention.
Figure 18B:
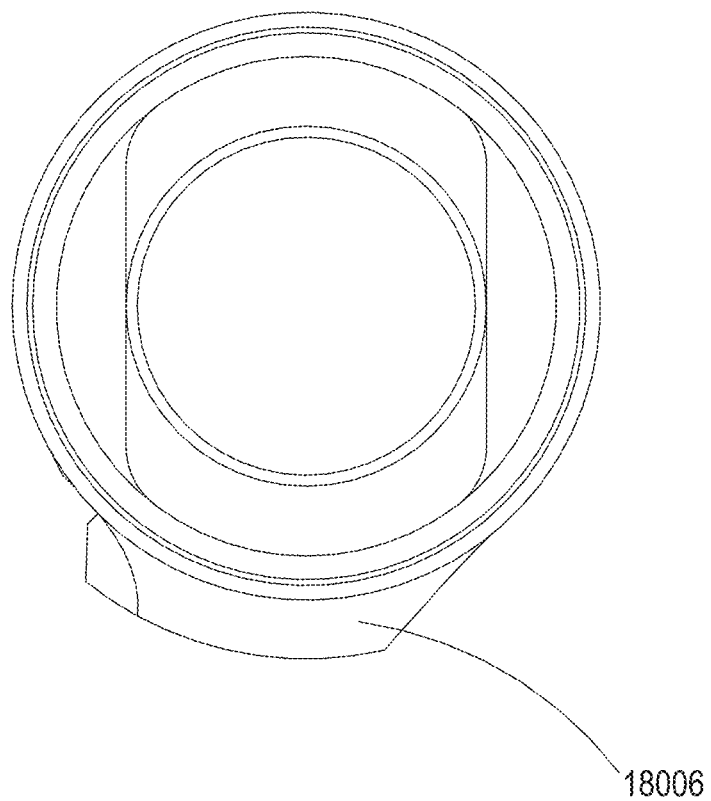
Figure 18C:
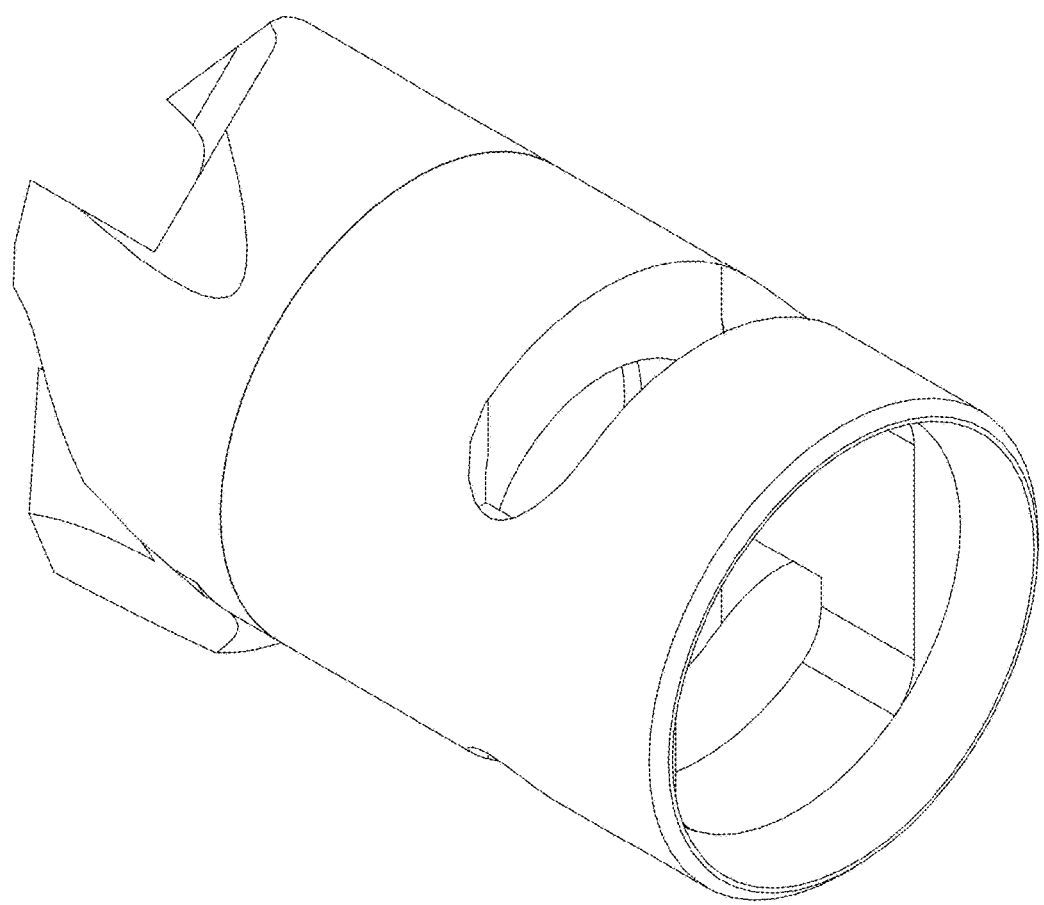
Figure 18D:
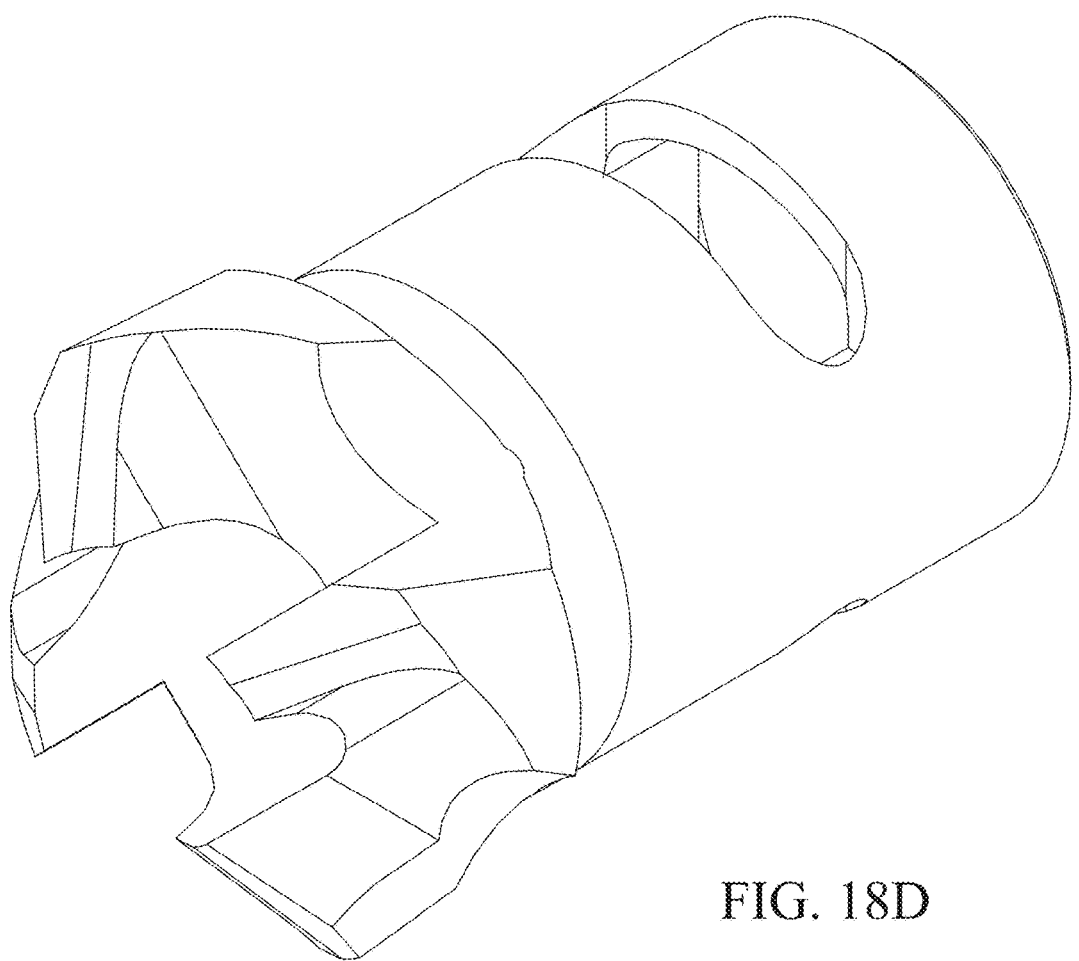
Figure 18E:
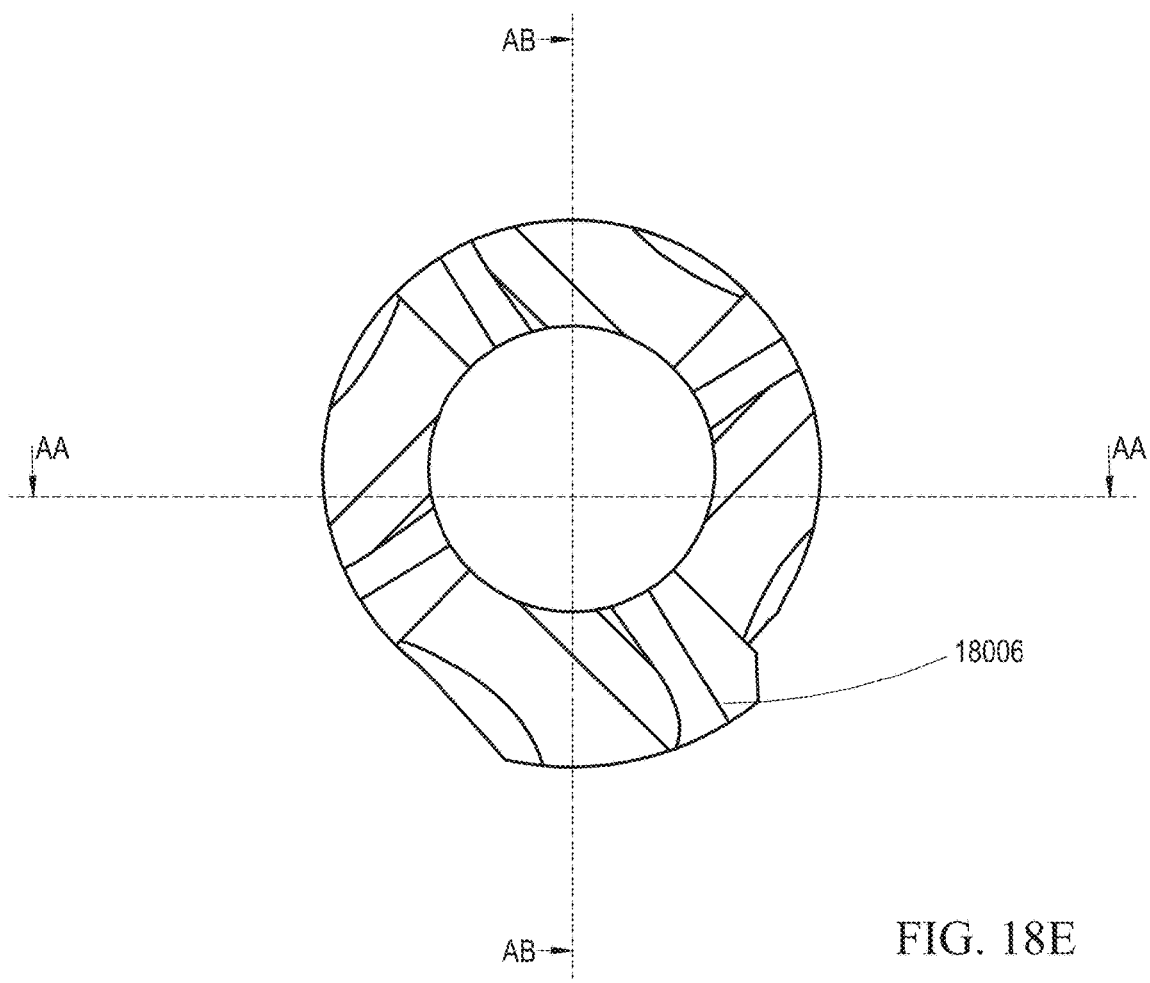
Figure 18F:
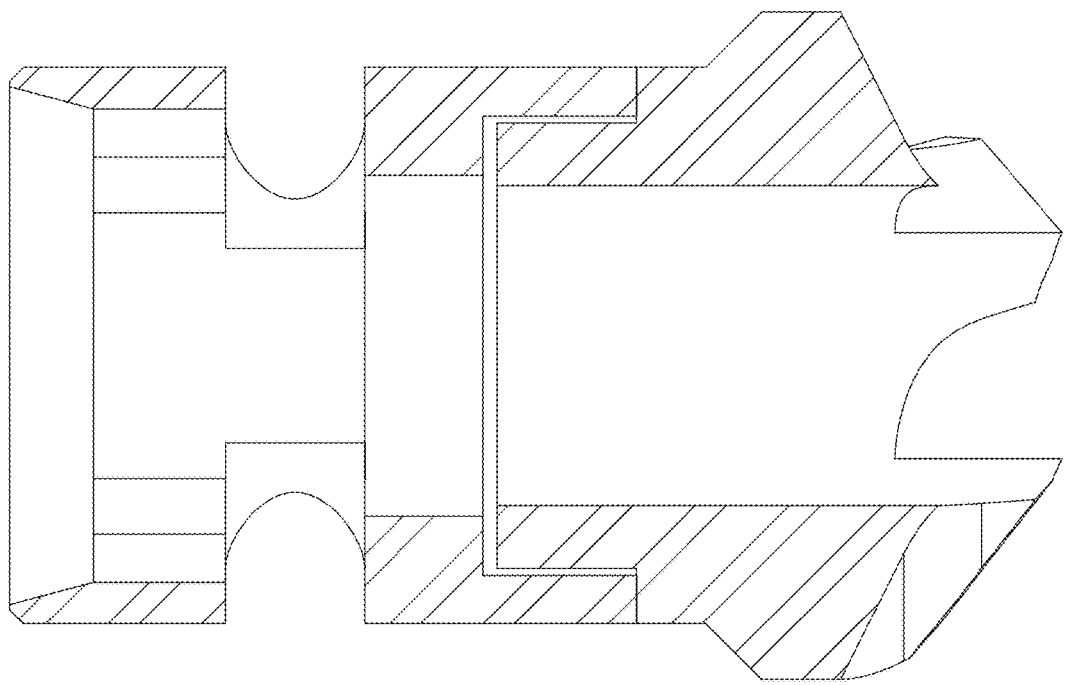
Figure 18G:
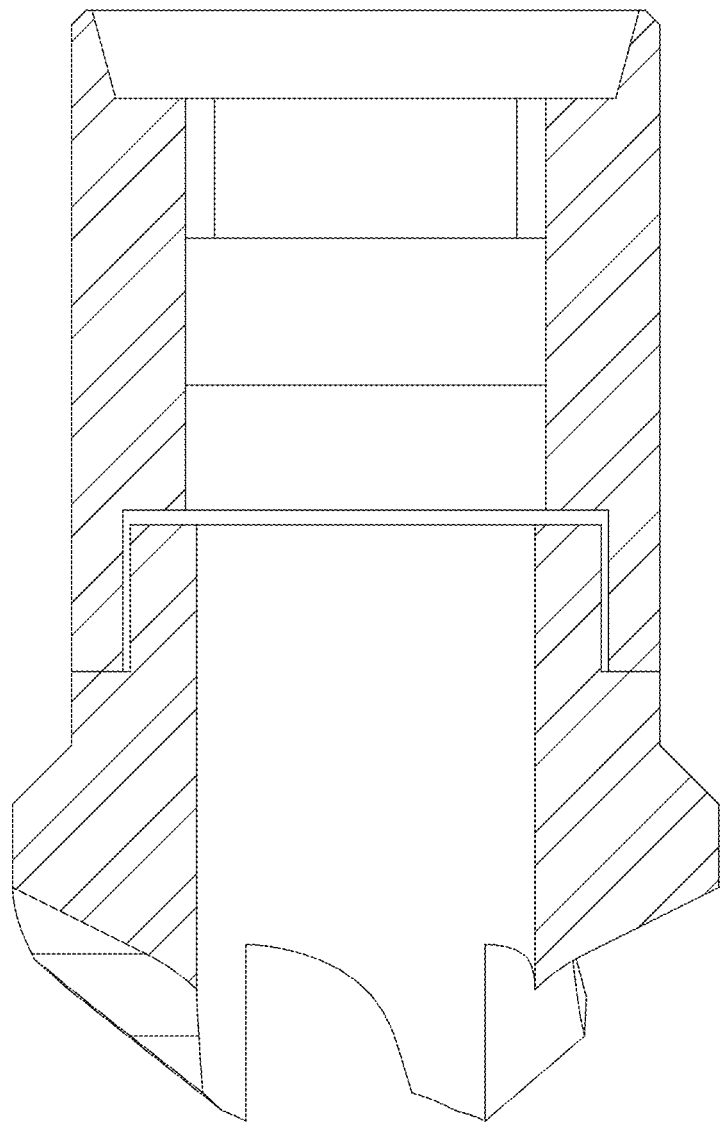
Figure 19A:
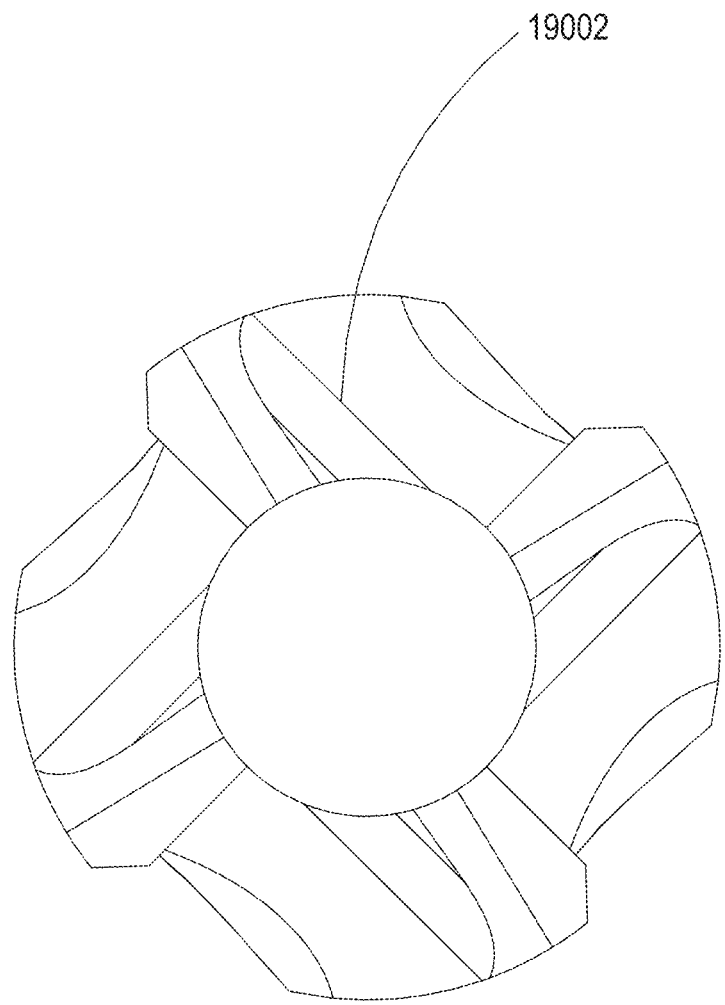
FIGS. 19A-E illustrate another configuration of a distal cutting head configured to engage a flexible bone tool in accordance with FIG. 12, according to some embodiments of the invention.
Figure 19B:
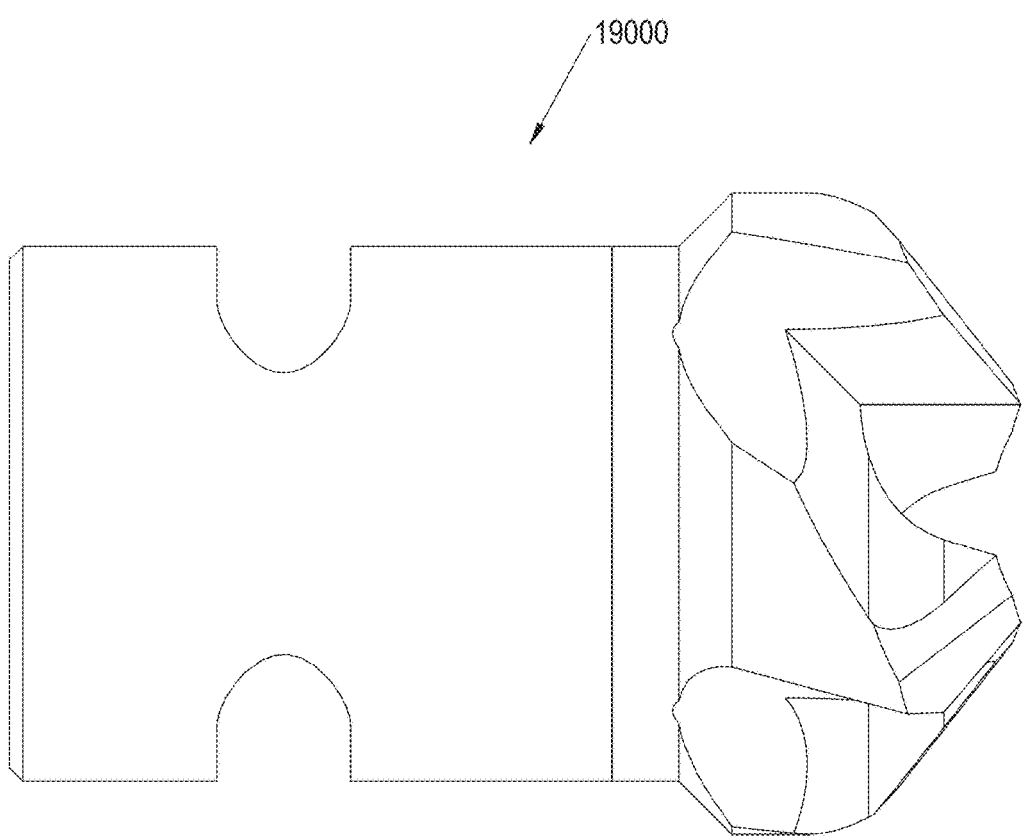
Figure 19C:
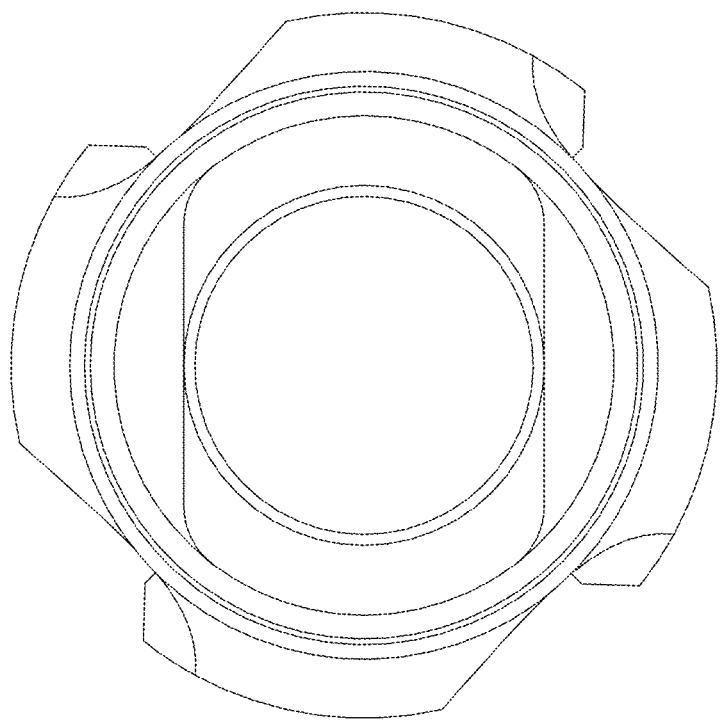
Figure 19D:
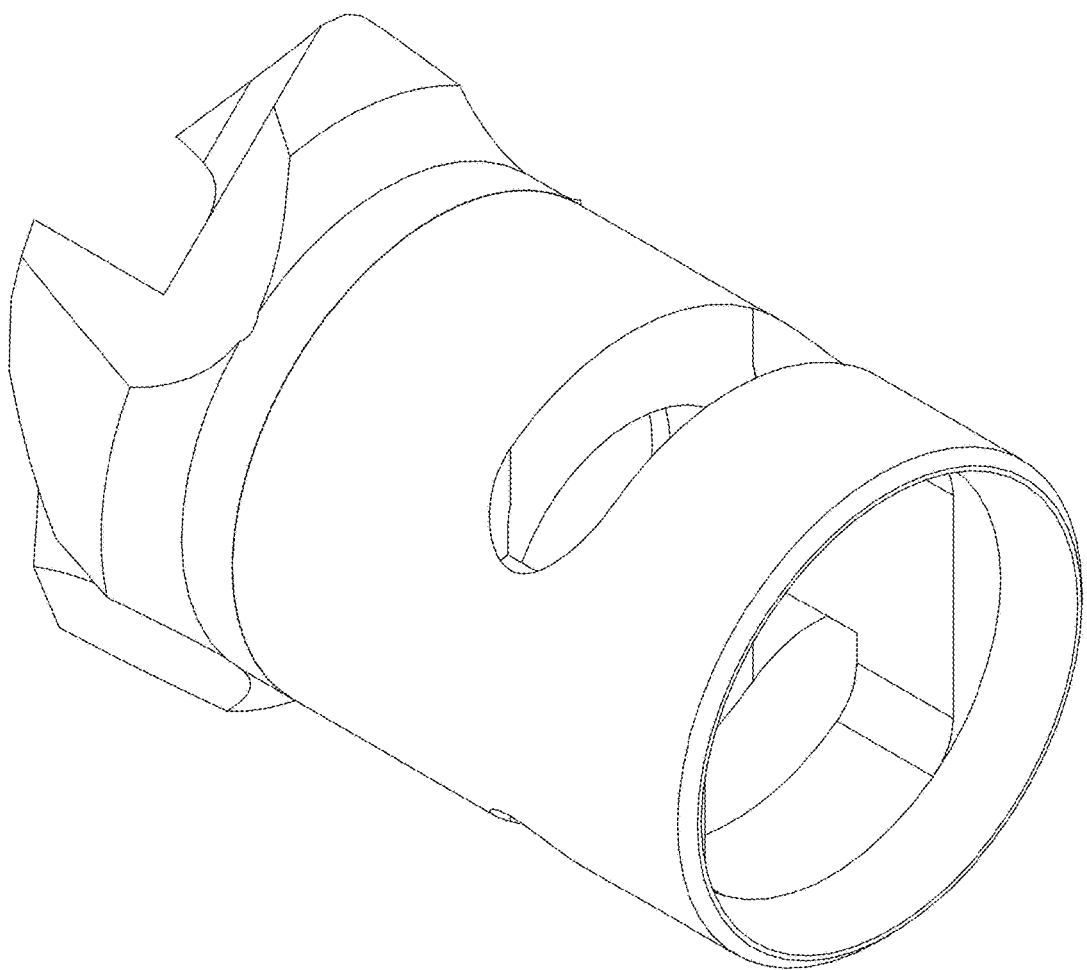
Figure 19E:
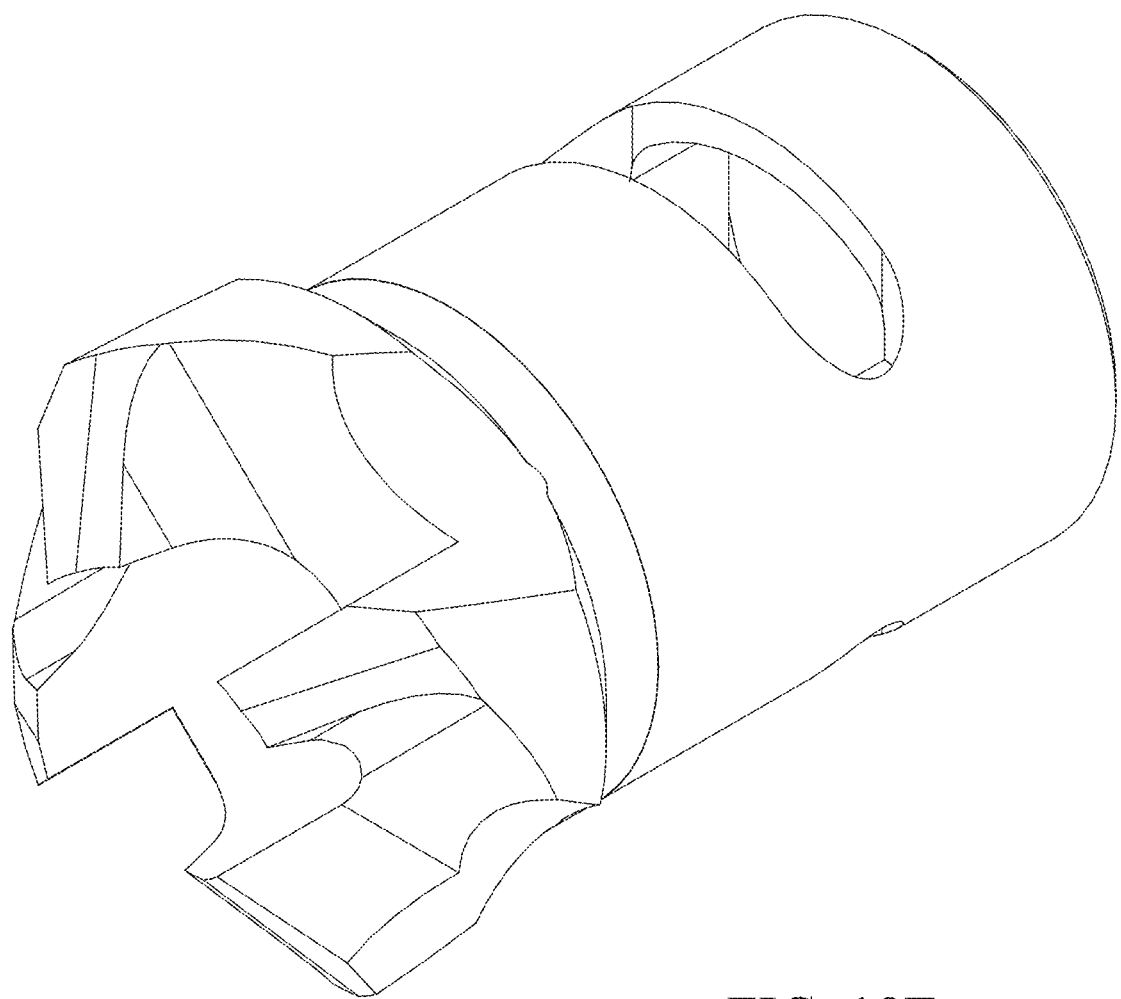

FIGS. 17A-C are cross section views of a link in accordance with FIG. 12 (17A), a receiving subsequent link (17B), rotationally oriented relative to the link of 17A, and the links coupled to each other (17C), according to some embodiments of the invention. FIGS. 17A-C generally correspond to the described above in FIGS. 7A-C and the description of corresponding parts will not be repeated.

FIGS. 18A-G illustrate a distal cutting head configured to engage a flexible bone tool in accordance with FIG. 12, according to some embodiments of the invention. FIGS. 18A-G generally correspond to the described above in FIGS. 8A-G and the description of corresponding parts will not be repeated.

FIGS. 19A-E illustrate another configuration of a distal cutting head configured to engage a flexible bone tool in accordance with FIG. 12, according to some embodiments of the invention. FIGS. 19A-E generally correspond to the described above in FIGS. 9A-E and the description of corresponding parts will not be repeated.

Figure 20:
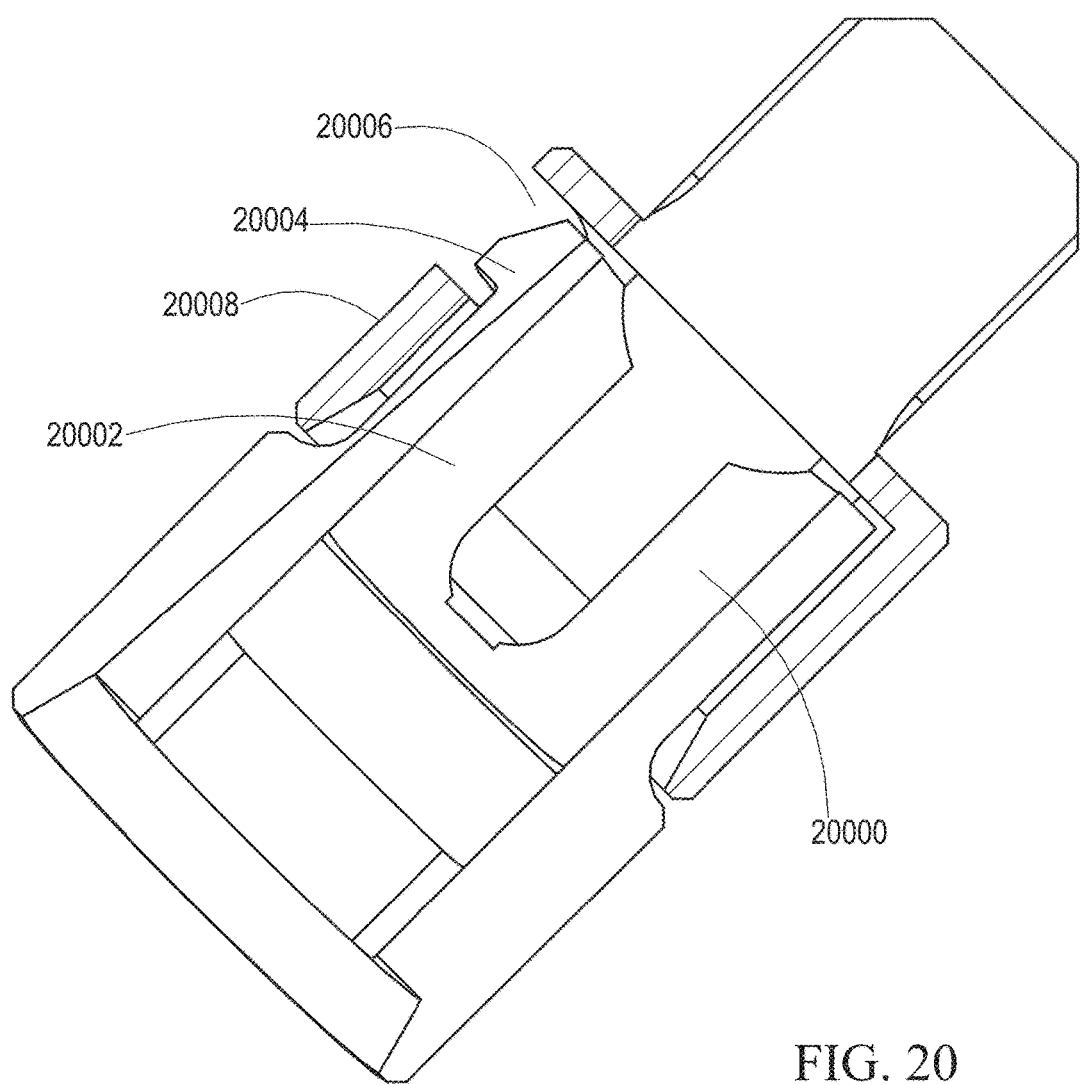
FIG. 20 is an exemplary link structure of the flexible bone tool, comprising a single radial protrusion for engaging an externally extending recess of a subsequent link, according to some embodiments of the invention.

FIG. 20 is an exemplary link structure of the flexible bone tool, comprising a single radial protrusion for engaging an externally extending recess of a subsequent link, according to some embodiments of the invention.

In some embodiments, only some of the tooth like extensions out of a plurality of tooth like extensions such as 1 extension, 2 extensions, 4 extensions or intermediate, larger or smaller number comprises a radial protrusion. In the exemplary configuration shown herein, a link comprises two teeth like extensions 20000 and 20002, only one of which (for example 20002) comprises a radial protrusion 20004. In the exemplary configuration shown herein, the receiving subsequent link comprises an externally extending recess 20006 in which protrusion 20004 is received.

In some embodiments, recess 20006 extends at least along a circumferential portion of outer wall 20008, such that the radial protrusion 20004 that is received within the recess can be viewed from outside the tubular body of the flexible bone tool. In some embodiments, the one or more recesses of a receiving, subsequent link are angularly rotated relative to the one or more recesses of the preceding link, for example oriented at an angle ranging between 5-180 degrees such as 30 degrees, 60 degrees, 90 degrees, 120 degrees, 180 degrees or intermediate, larger or smaller angles.

In some embodiments, the number of protrusions is selected for obtaining a certain pull-out separation force between the links. In an example, axial pull-out force required for separating between links (for example when adjusting the tool) in a single protrusion configuration would be lower than the axial force required for separating links having a 2-protrusion configuration.

Figure 21A:
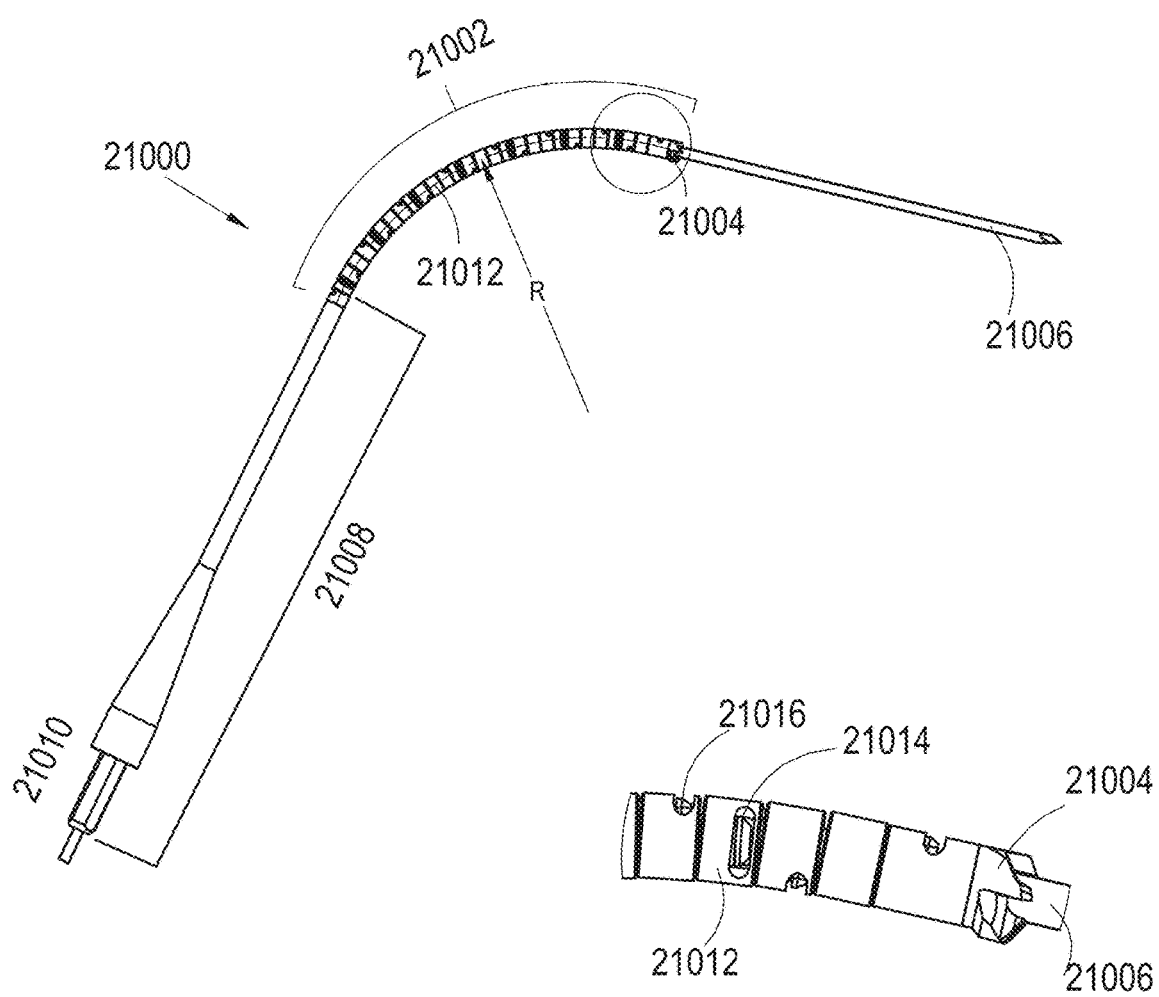
FIGS. 21A-B illustrate a flexible bone tool in accordance with FIG. 20 in a flexed configuration (21A) and straight configuration (21B), according to some embodiments of the invention.
Figure 21B:
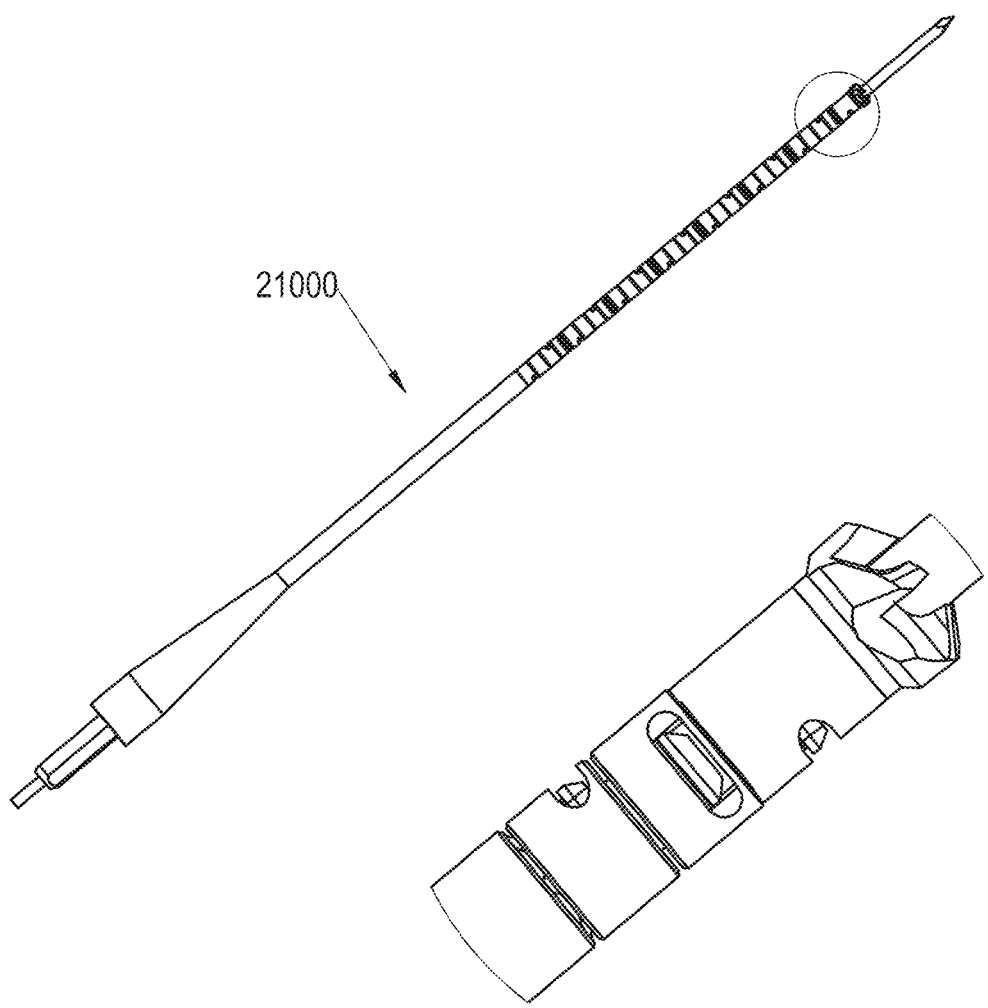

FIGS. 21A-B illustrate a flexible bone tool in accordance with FIG. 20 in a flexed configuration (21A) and straight configuration (21B), according to some embodiments of the invention. FIGS. 21A-B generally correspond to the described above in FIGS. 3A-B and the description of corresponding parts will not be repeated. It is noted that in a tubular body comprising the exemplary link structure of FIG. 20, the externally extending recess 21014 and the radial protrusion 21016 can be observed from outside the tubular body. In the exemplary configuration shown herein, recesses of adjacent links are rotationally oriented at a 90 degree angle relative to each other.

Figure 22:
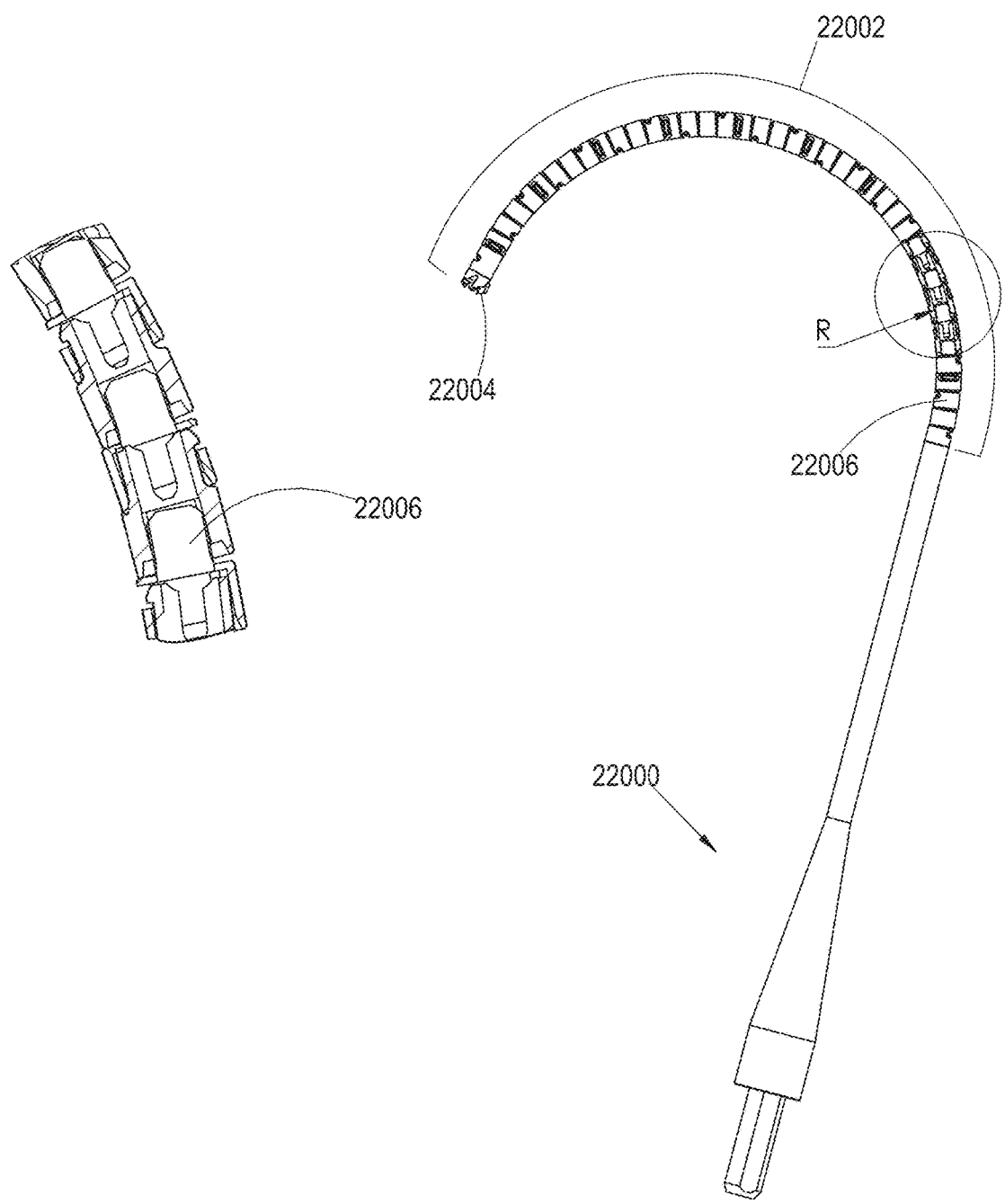
FIG. 22 illustrates a flexible bone tool in accordance with FIG. 20 bent into a U-curve, according to some embodiments of the invention.

FIG. 22 illustrates a flexible bone tool in accordance with FIG. 20 bent into a U-curve, according to some embodiments of the invention. FIG. 22 generally corresponds to the described above in FIG. 4 and the description of corresponding parts will not be repeated. In this figure, the externally extending recess and the radial protrusion that is aligned with or projects radially outwardly from the tubular body are shown.

Figure 23A:
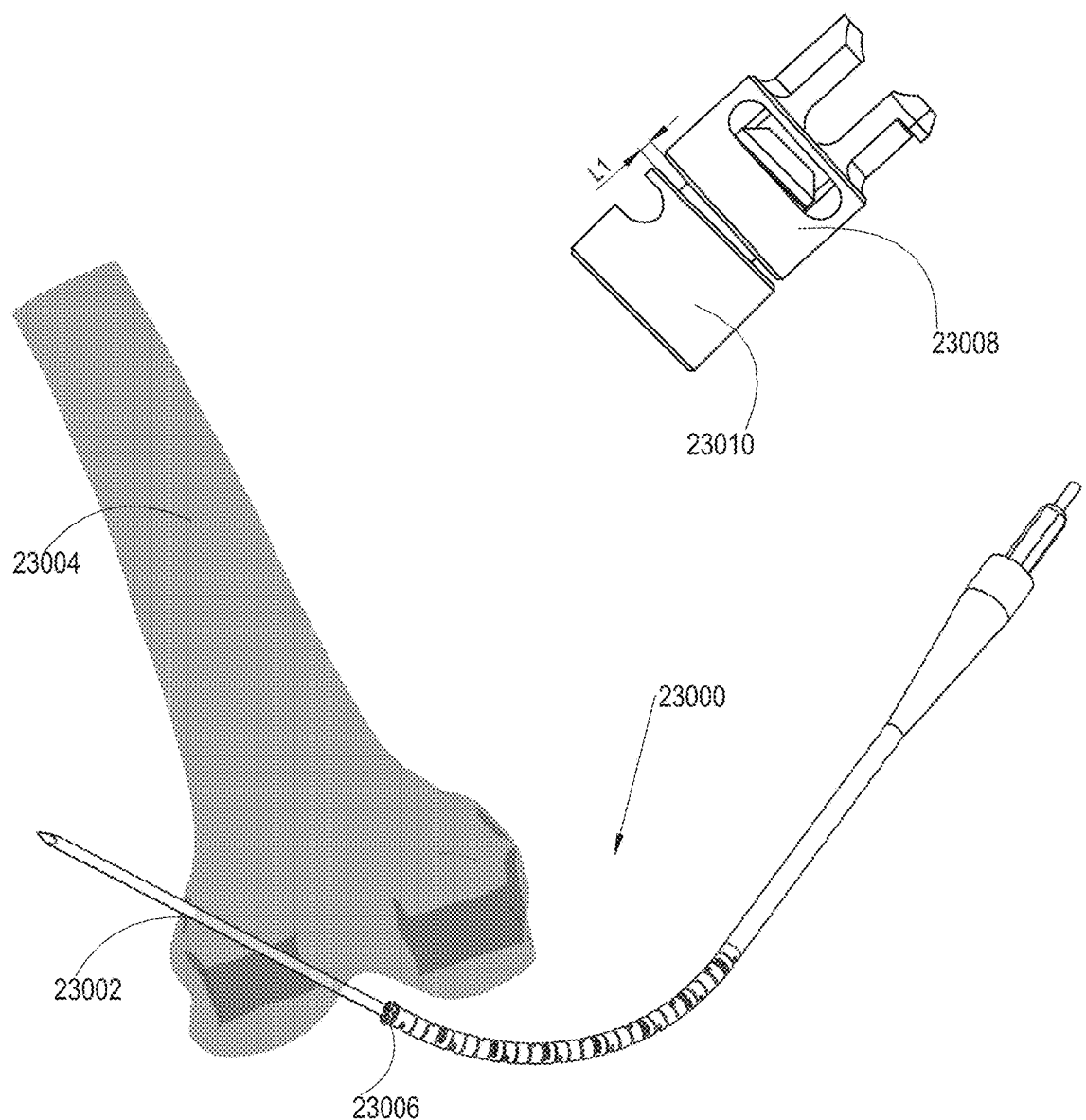
FIGS. 23A-B illustrate advancement of a flexible bone tool in accordance with FIG. 20 into a bone, according to some embodiments of the invention.
Figure 23B:
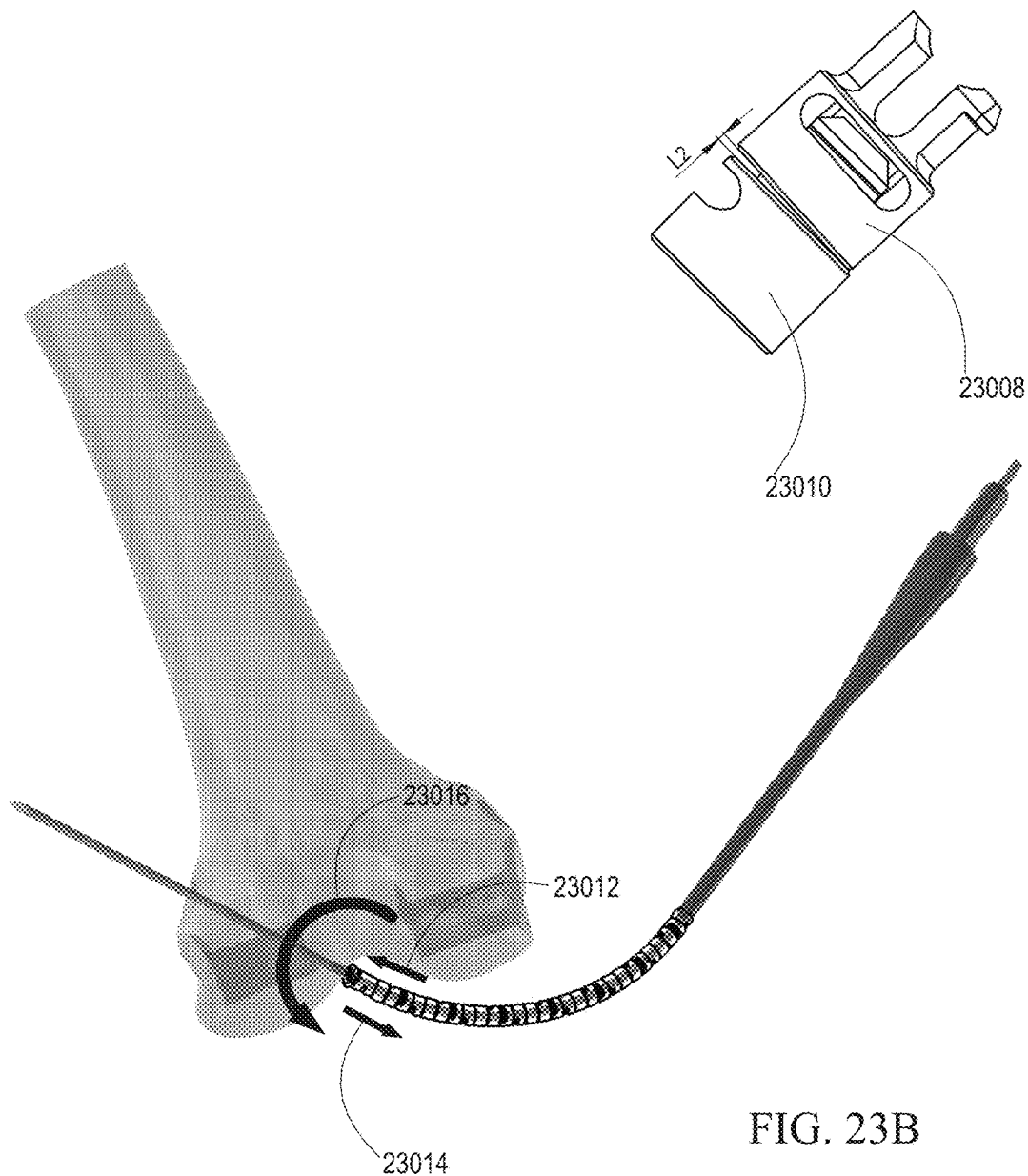
Figure 24A:
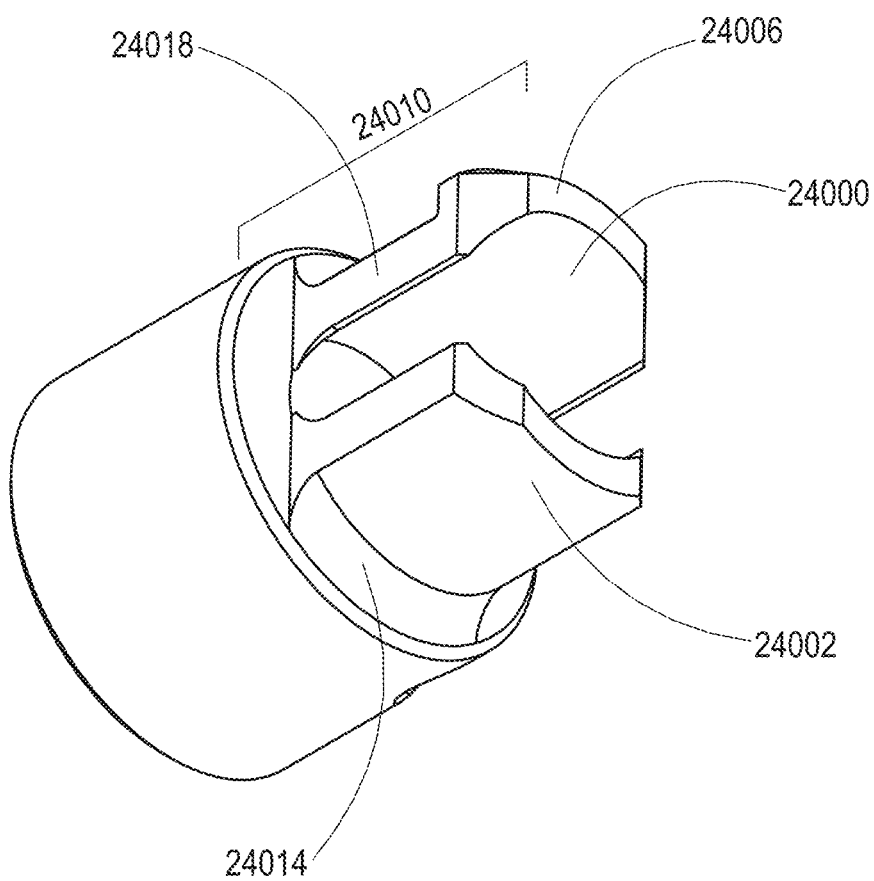
FIGS. 24A-E are views of a link in accordance with FIG. 20 from various directions and cross sections, according to some embodiments of the invention.
Figure 24B:
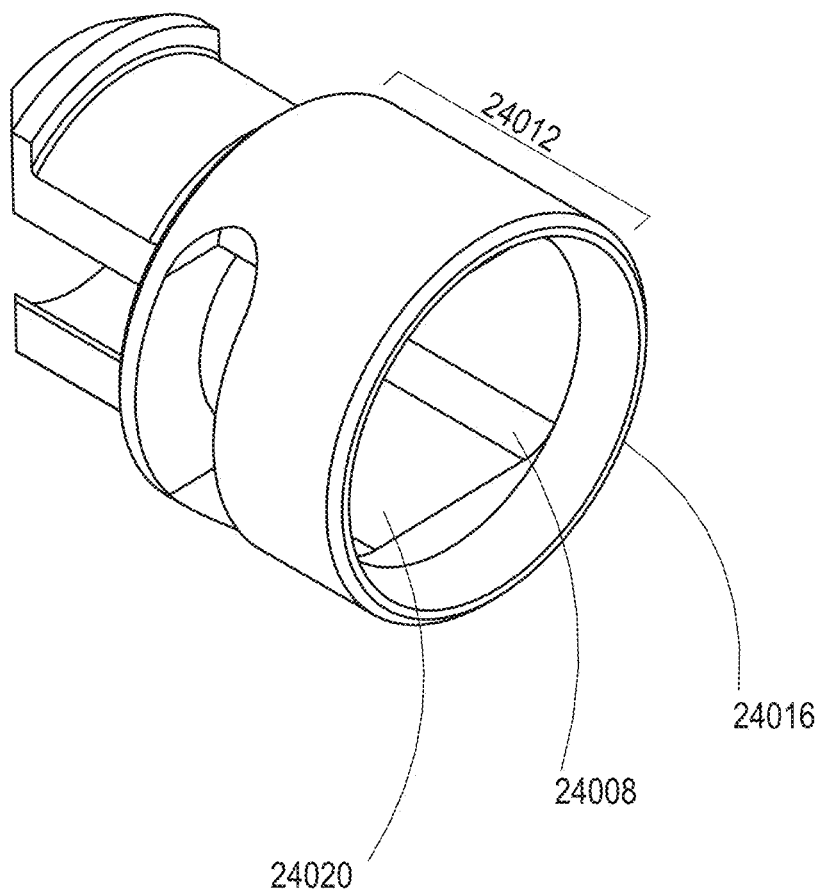
Figure 24C:
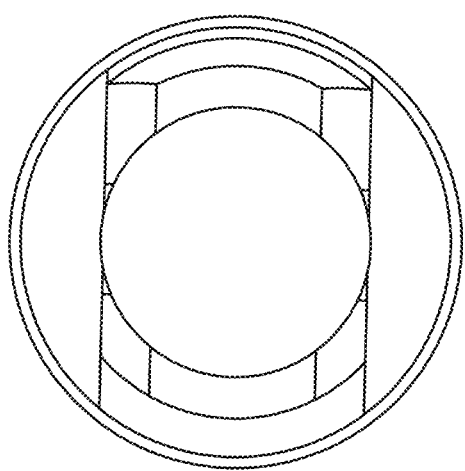
Figure 24D:
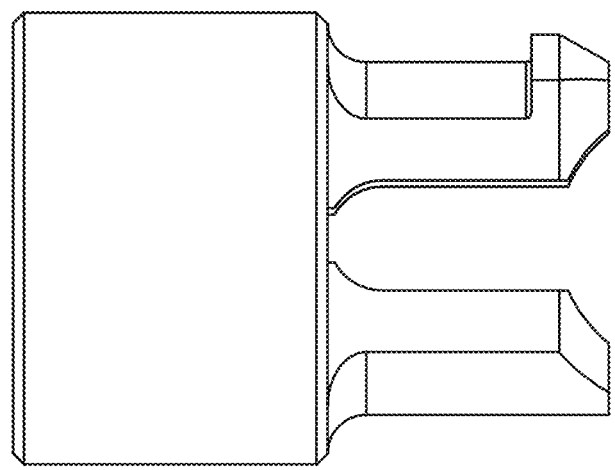
Figure 24E:
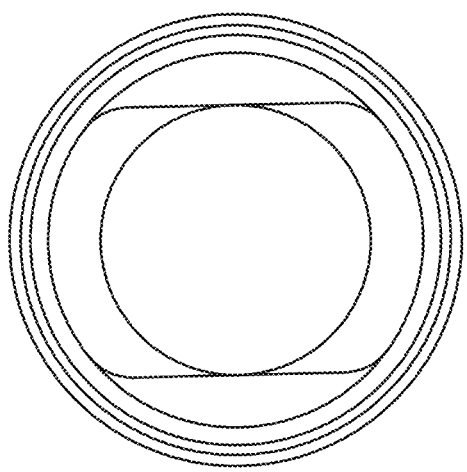

FIGS. 23A-B illustrate advancement of a flexible bone tool in accordance with FIG. 20 into a bone, according to some embodiments of the invention. FIGS. 23A-B generally correspond to the described above in FIGS. 5A-B and the description of corresponding parts will not be repeated.

FIGS. 24A-E are views of a link in accordance with FIG. 20 from various directions and cross sections, according to some embodiments of the invention. FIGS. 24A-E generally correspond to the described above in FIGS. 6A-E and the description of corresponding parts will not be repeated. It is noted that in this exemplary configuration, only one of the tooth like extensions comprises a radial protrusion 24006.

Figure 25A:
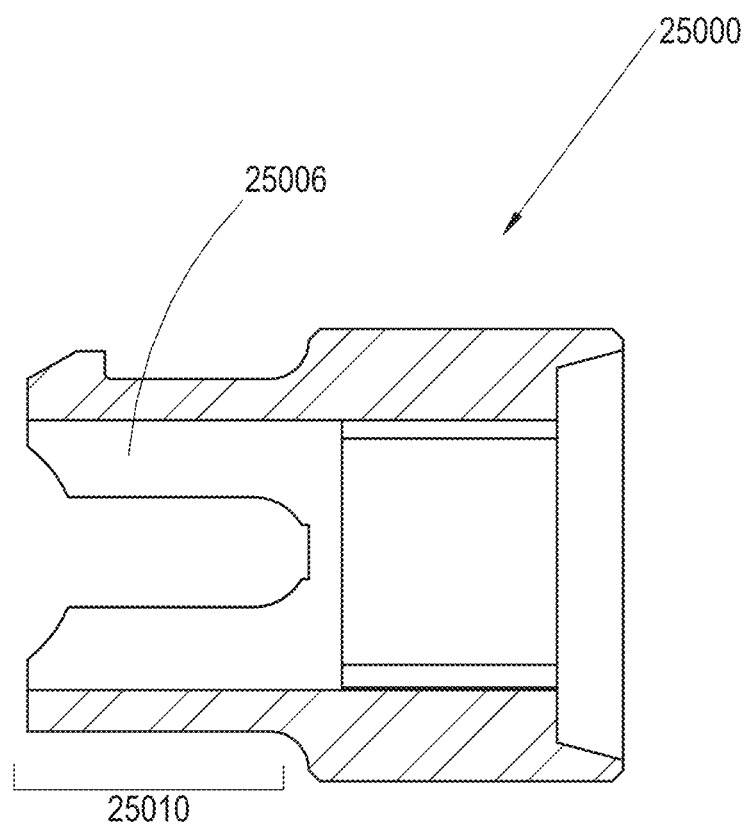
FIGS. 25A-C are cross section views of a link (25A), a receiving subsequent link (25B), rotationally oriented relative to the link of 25A, and the links coupled to each other (25C), according to some embodiments of the invention.
Figure 25B:
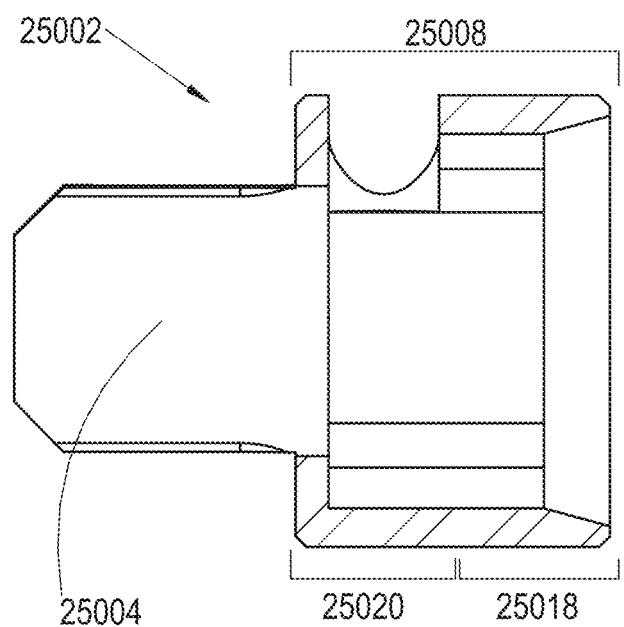
Figure 25C:
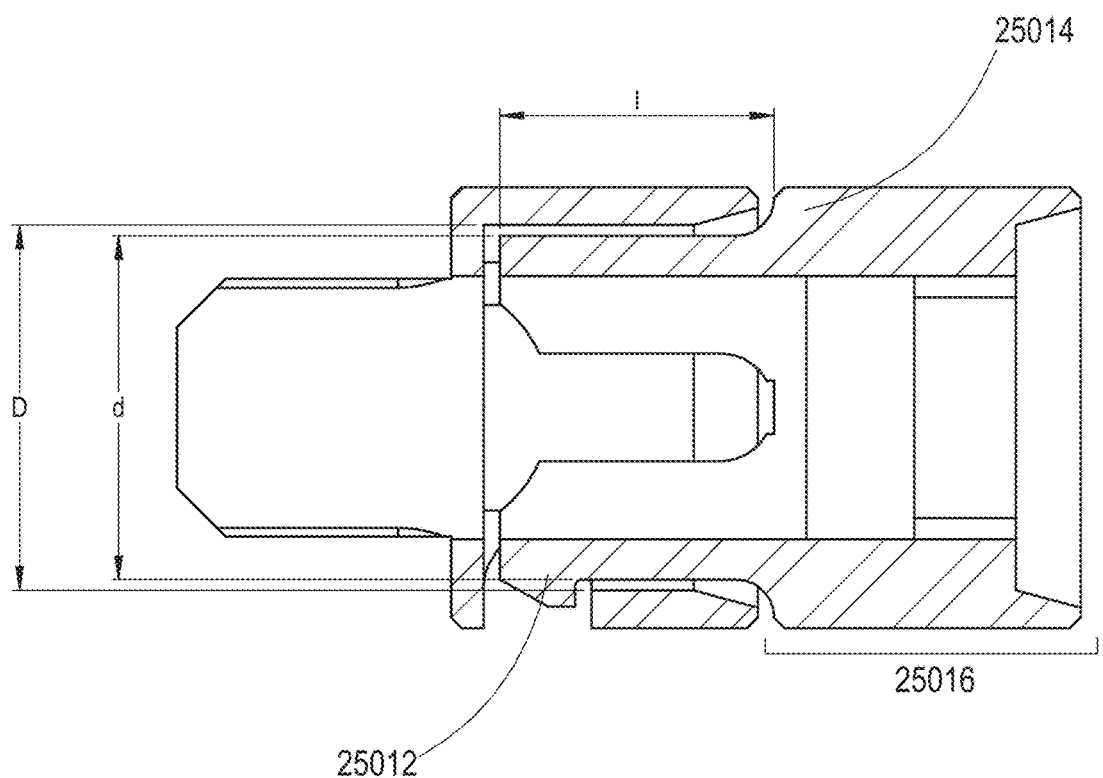
Figure 26A:
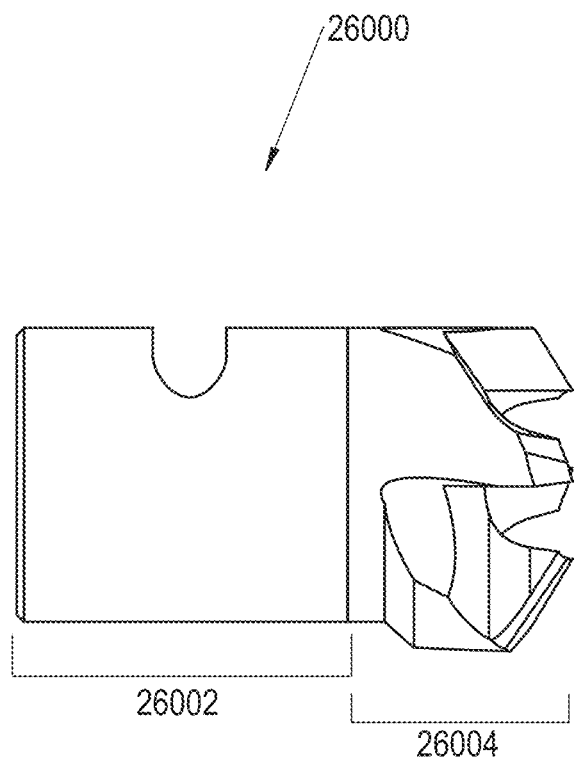
FIGS. 26A-G illustrate a distal cutting head configured to engage a flexible bone tool in accordance with FIG. 20, according to some embodiments of the invention.
Figure 26B:
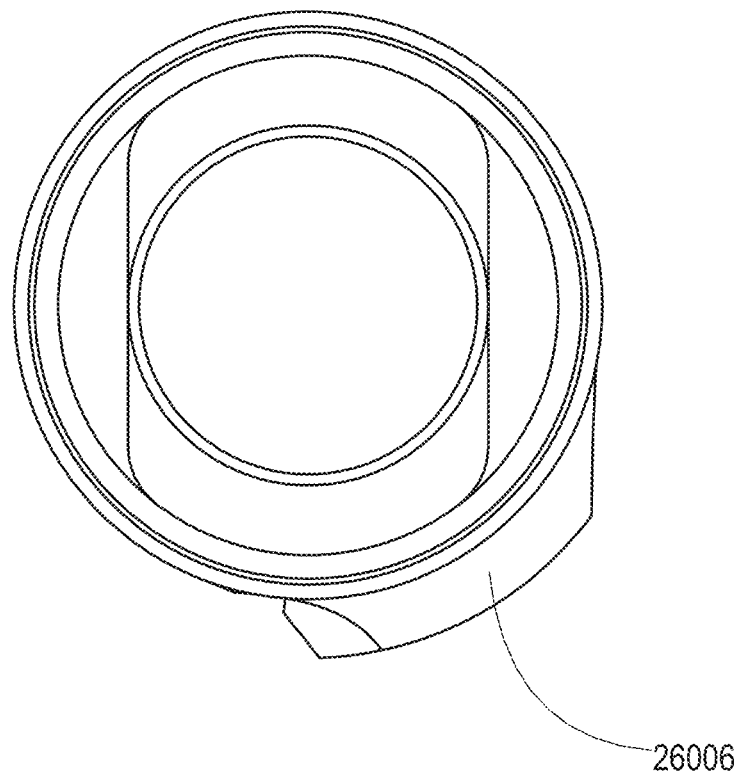
Figure 26C:
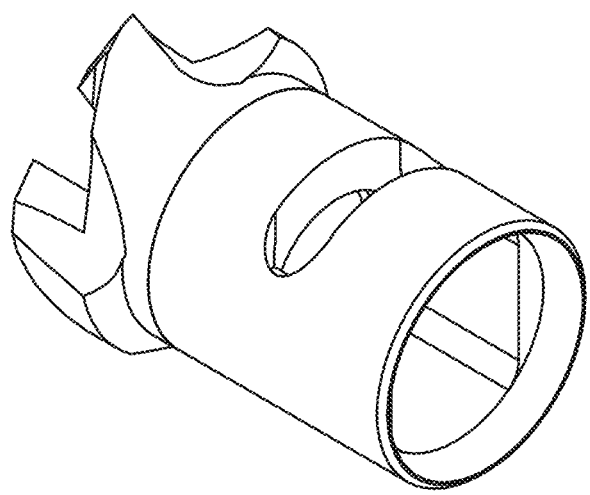
Figure 26D:
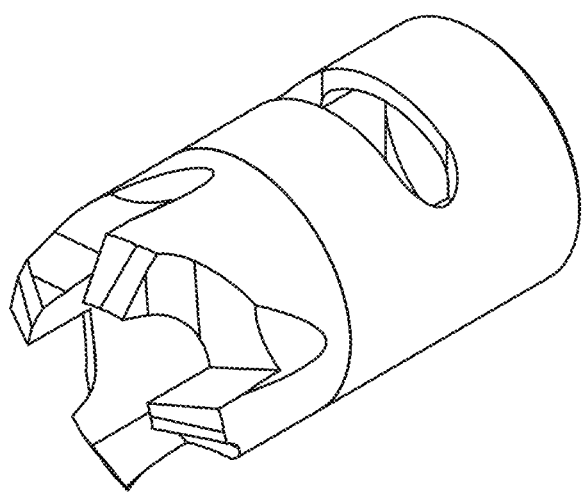
Figure 26E:
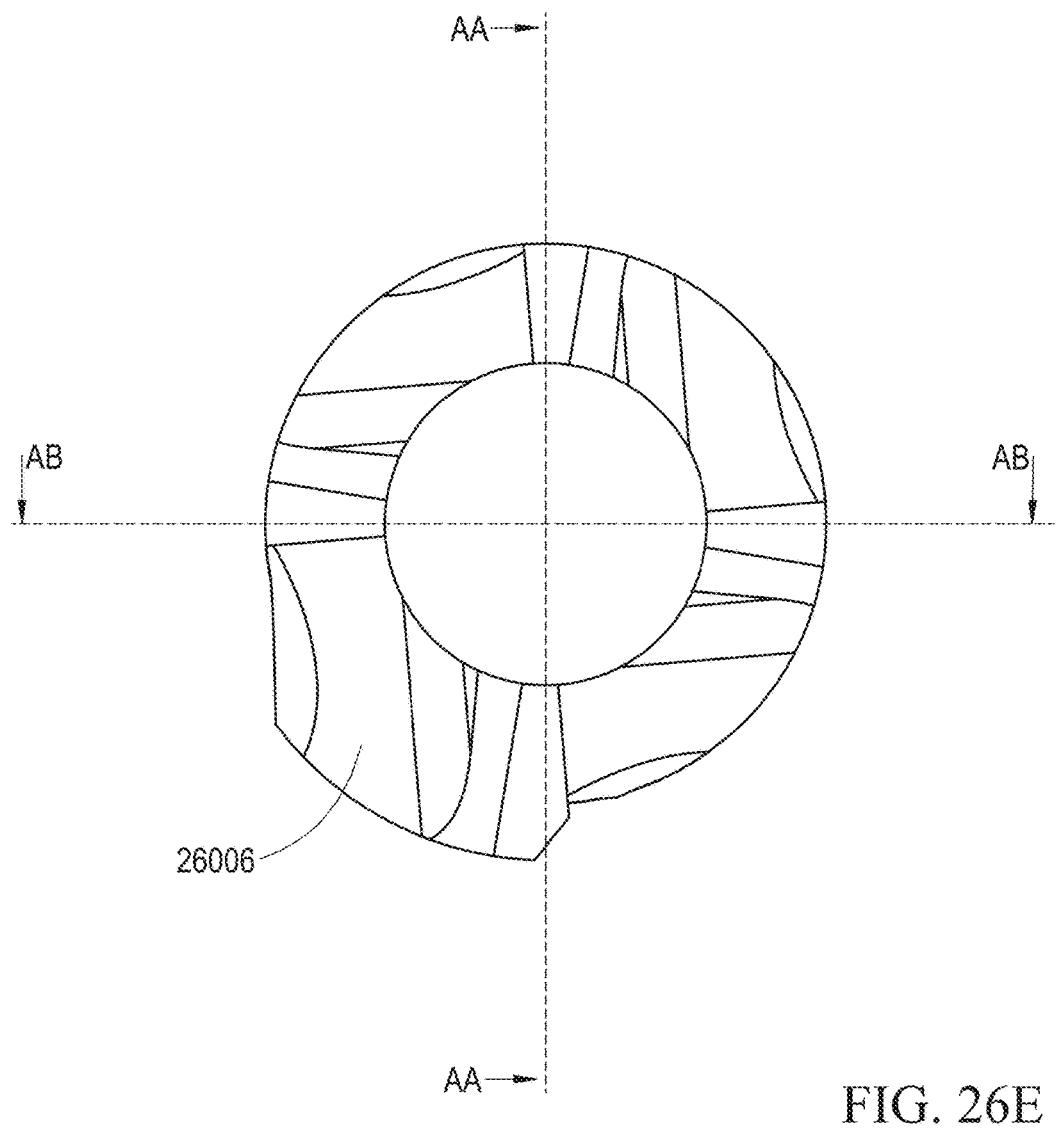
Figure 26F:
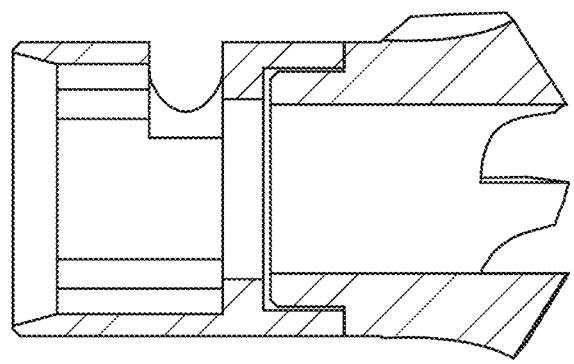
Figure 26G:
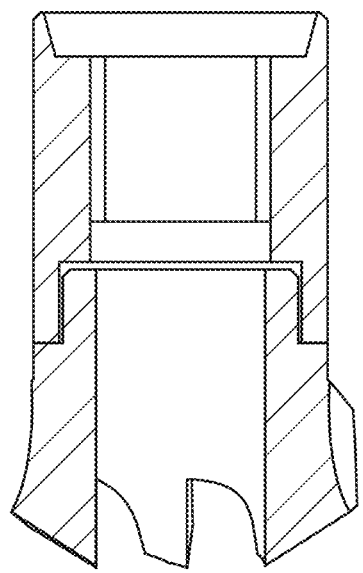
Figure 27A:
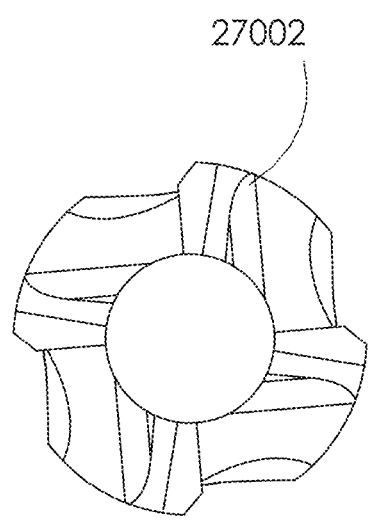
FIGS. 27A-E illustrate another configuration of a distal cutting head configured to engage a flexible bone tool in accordance with FIG. 20, according to some embodiments of the invention.
Figure 27B:
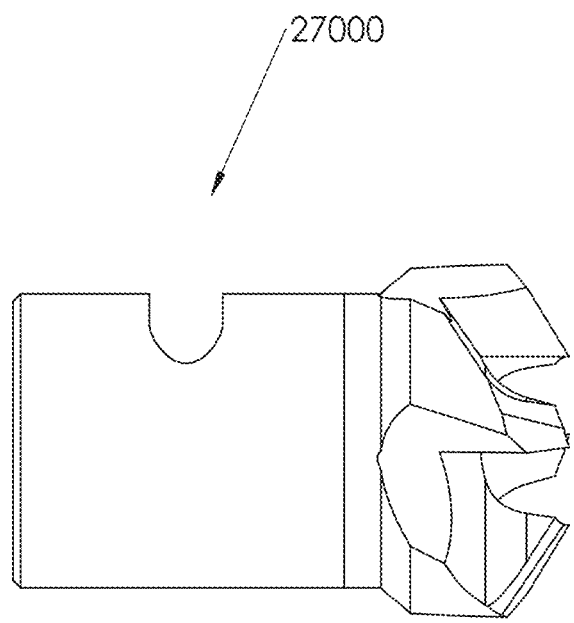
Figure 27C:
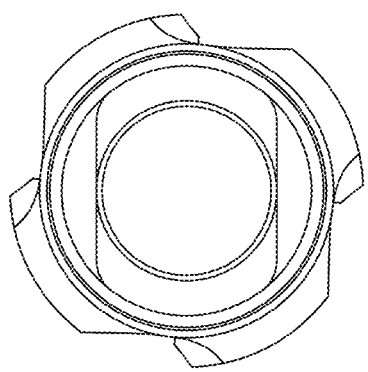
Figure 27D:
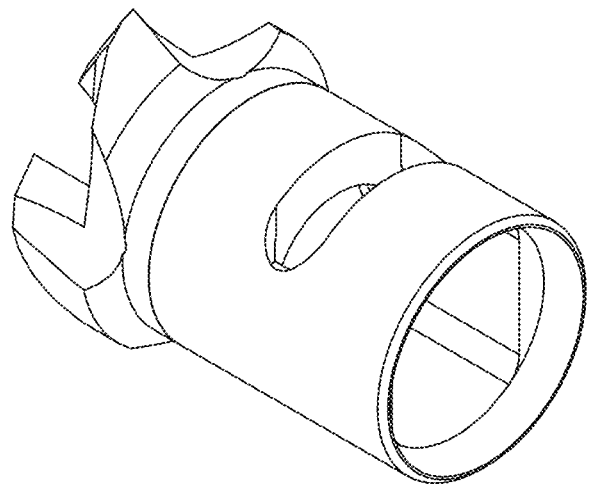
Figure 27E:
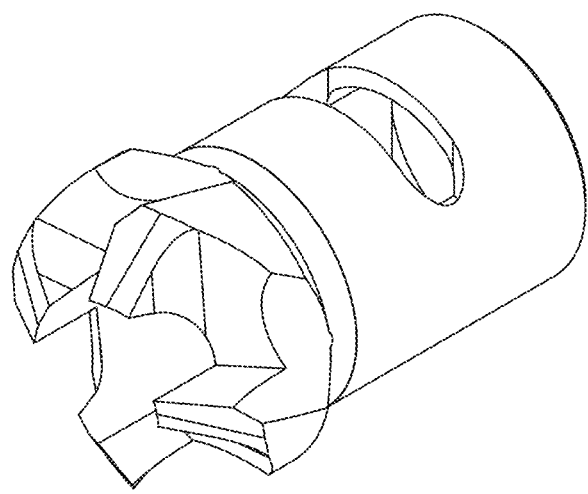

FIGS. 25A-C are cross section views of a link (25A), a receiving subsequent link (25B), rotationally oriented relative to the link of 25A, and the links coupled to each other (25C), according to some embodiments of the invention. FIGS. 25A-C generally correspond to the described above in FIGS. 7A-C and the description of corresponding parts will not be repeated.

FIGS. 26A-G illustrate a distal cutting head configured to engage a flexible bone tool in accordance with FIG. 20, according to some embodiments of the invention. FIGS. 26A-G generally correspond to the described above in FIGS. 8A-G and the description of corresponding parts will not be repeated.

FIGS. 27A-E illustrate another configuration of a distal cutting head configured to engage a flexible bone tool in accordance with FIG. 20, according to some embodiments of the invention. FIGS. 27A-E generally correspond to the described above in FIGS. 9A-E and the description of corresponding parts will not be repeated.

Figure 28:
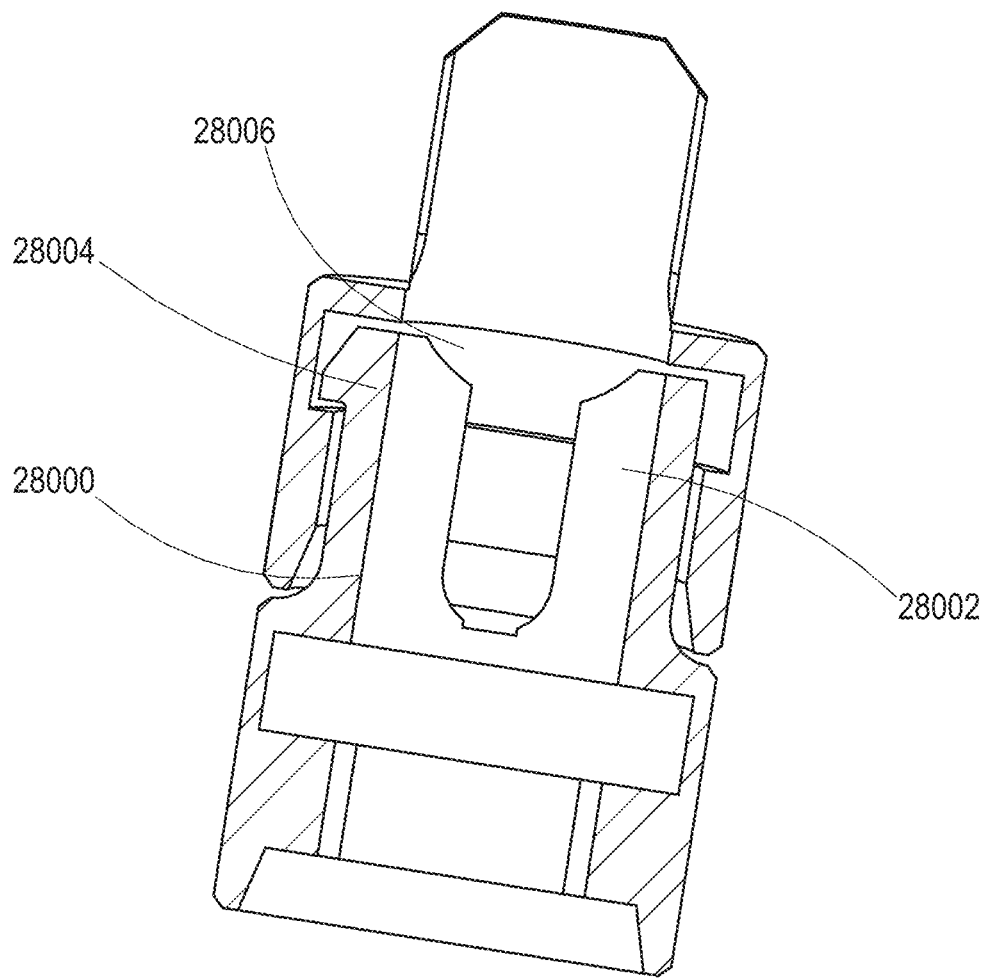
FIG. 28 is an exemplary link structure of the flexible bone tool, comprising a single radial protrusion for internally engaging a subsequent link, according to some embodiments of the invention.

FIG. 28 is an exemplary link structure of the flexible bone tool, comprising a single radial protrusion for internally engaging a subsequent link, according to some embodiments of the invention.

In this exemplary configuration, a link comprises two tooth like extensions 28000 and 28002, only one of which comprising a radial protrusion 28004 that is received within an internal recess 28006 of the subsequent link.

Figure 29A:
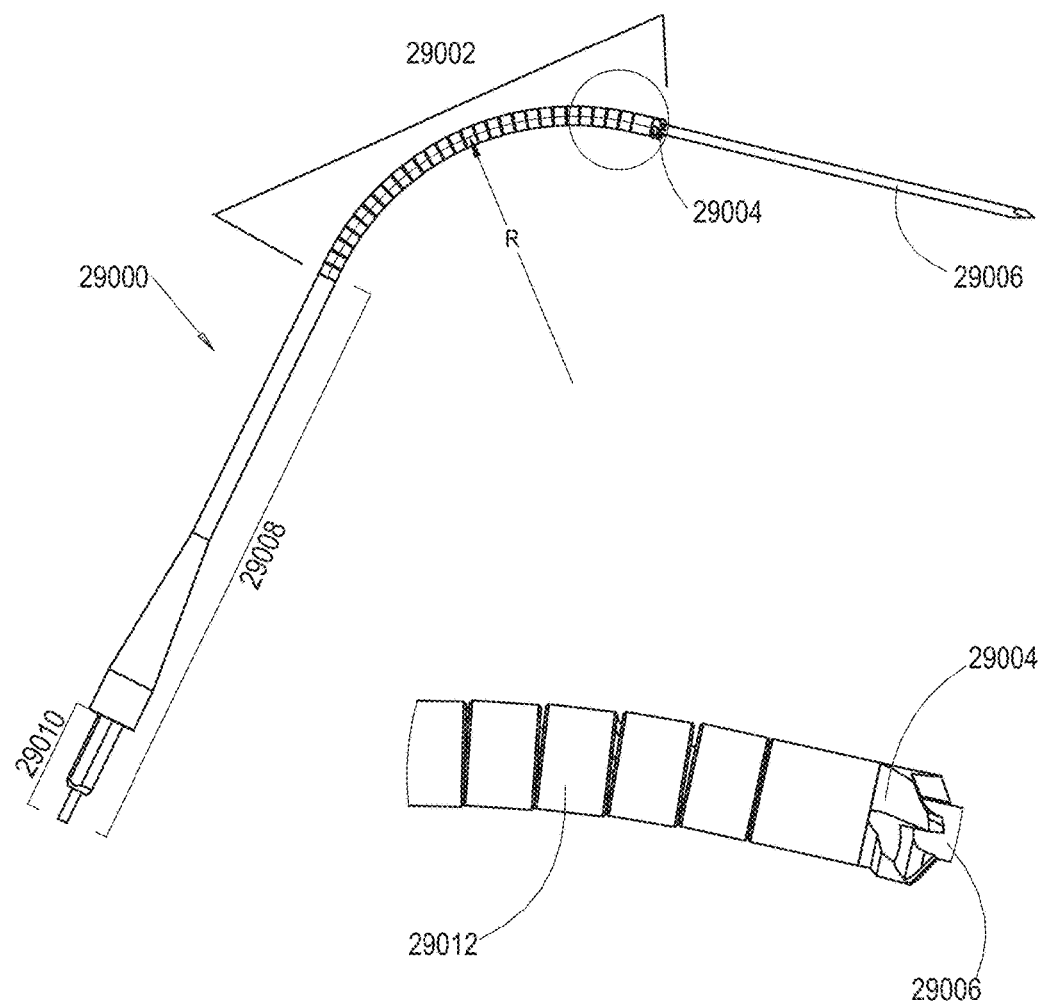
FIGS. 29A-B illustrate a flexible bone tool in accordance with FIG. 28 in a flexed configuration (29A) and straight configuration (29B), according to some embodiments of the invention.
Figure 29B:
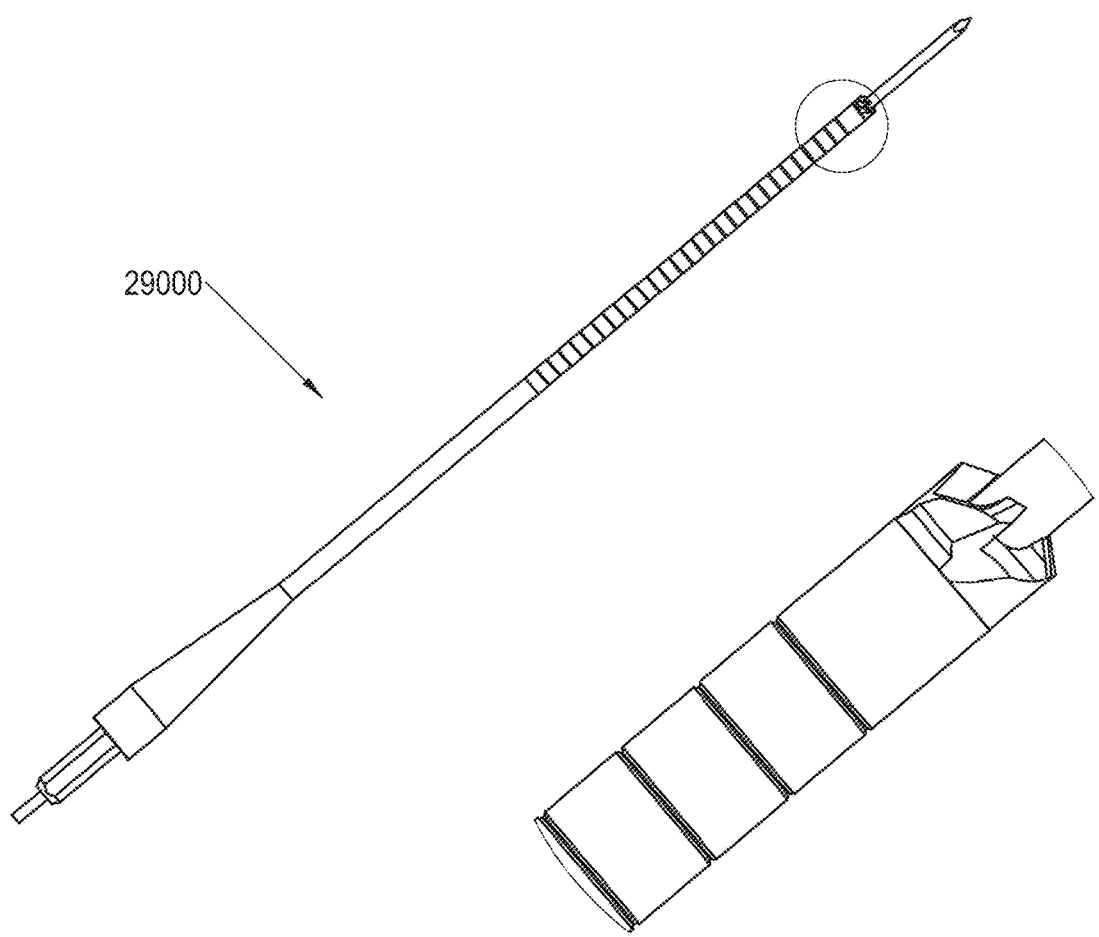

FIGS. 29A-B illustrate a flexible bone tool in accordance with FIG. 28 in a flexed configuration (29A) and straight configuration (29B), according to some embodiments of the invention. FIGS. 29A-B generally correspond to the described above in FIGS. 3A-B and the description of corresponding parts will not be repeated.

Figure 30:
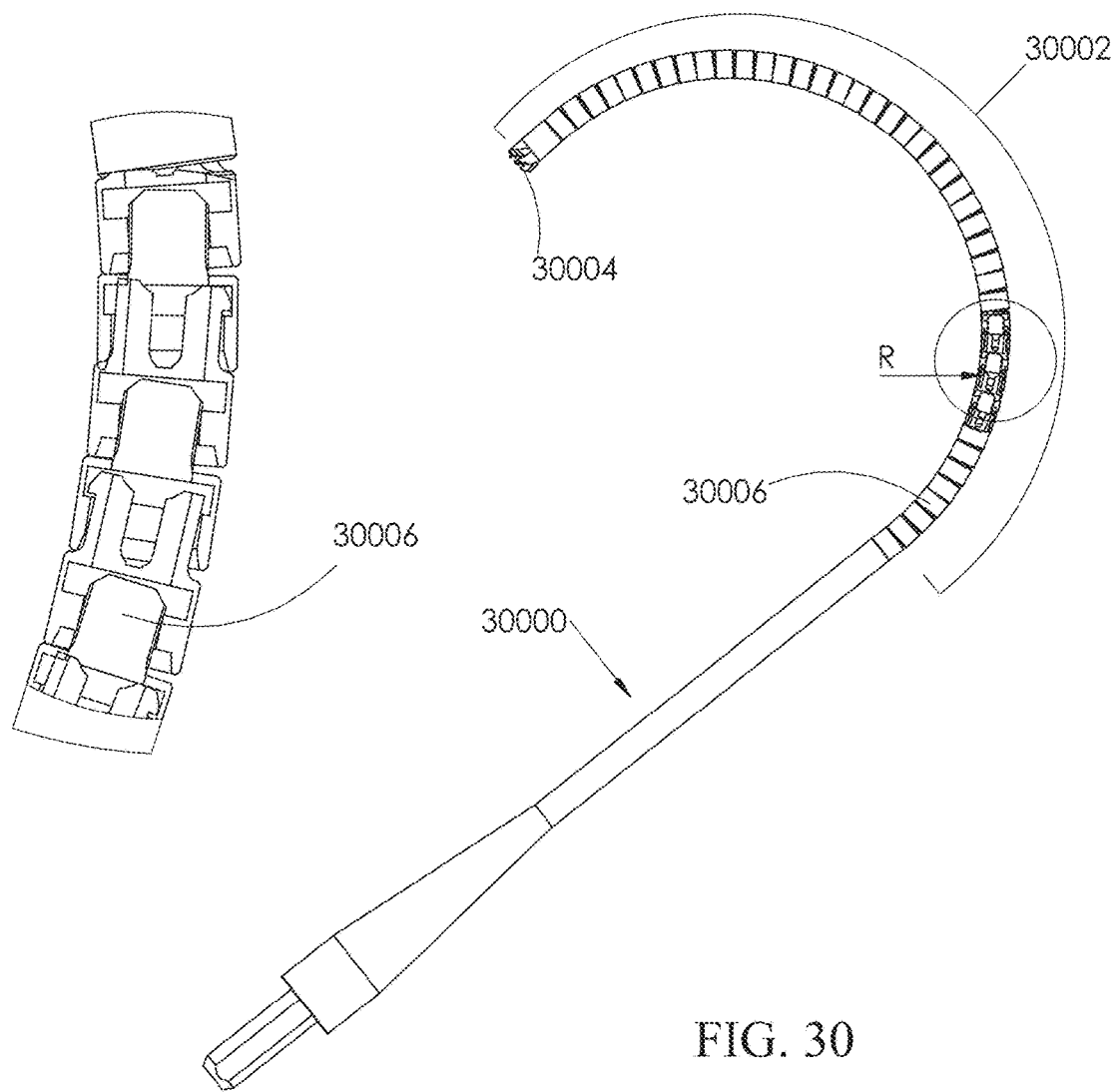
FIG. 30 illustrates a flexible bone tool in accordance with FIG. 28 bent into a U-curve, according to some embodiments of the invention.

FIG. 30 illustrates a flexible bone tool in accordance with FIG. 28 bent into a U-curve, according to some embodiments of the invention. FIG. 30 generally corresponds to the described above in FIG. 4 and the description of corresponding parts will not be repeated.

Figure 31A:
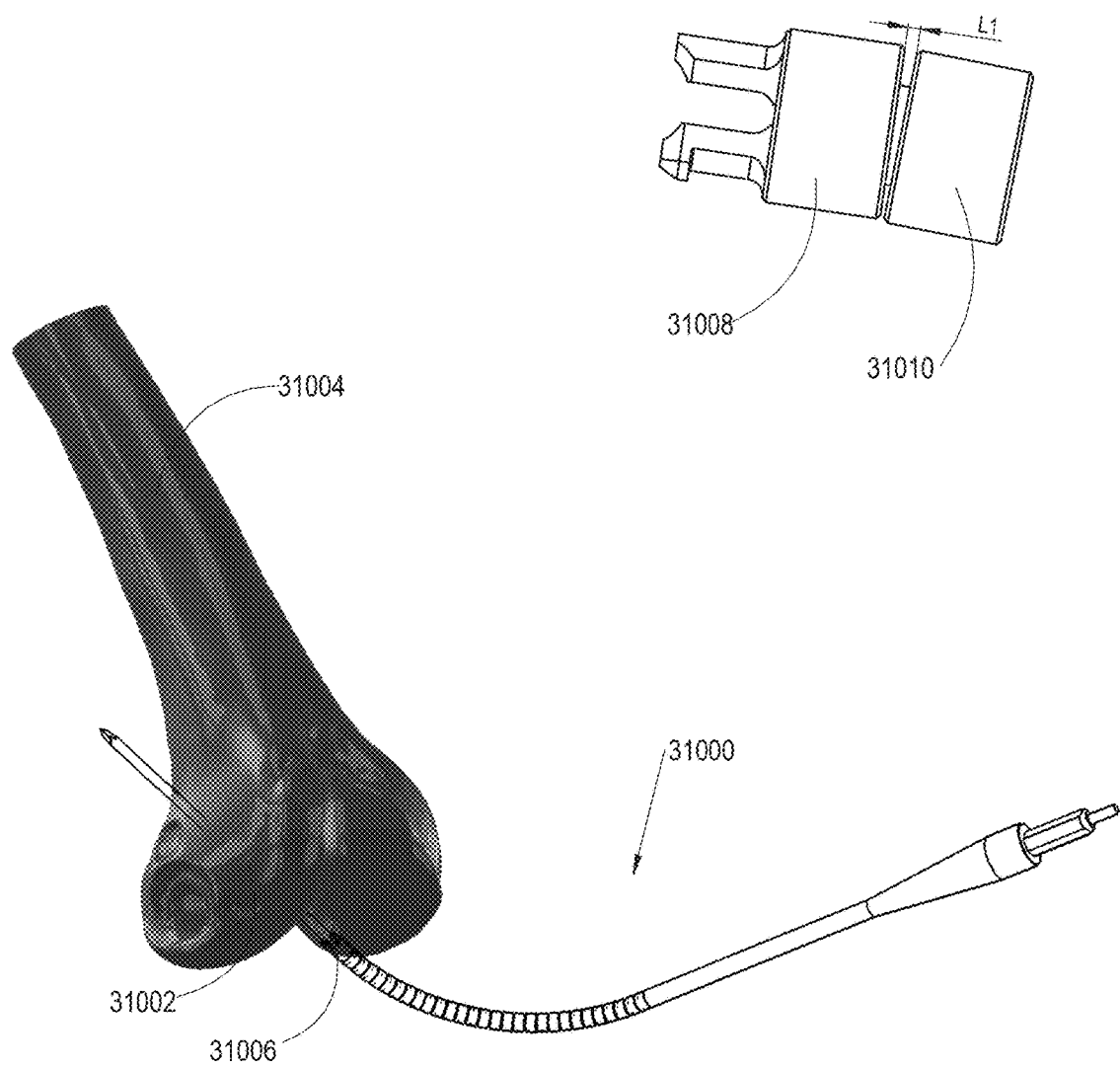
FIGS. 31A-B illustrate advancement of a flexible bone tool in accordance with FIGS. 2A1-C into a bone, according to some embodiments of the invention.
Figure 31B:
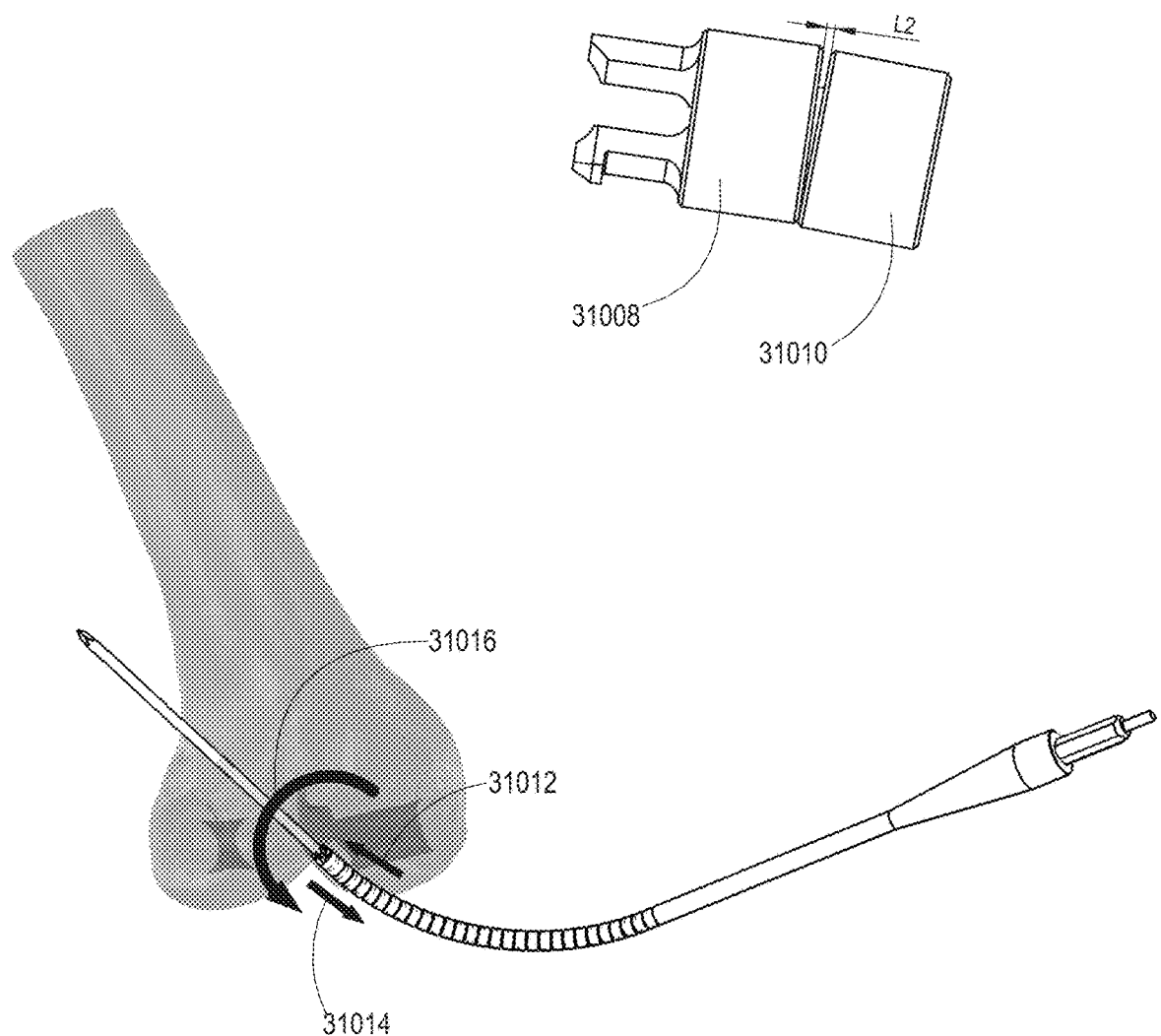
Figure 32A:
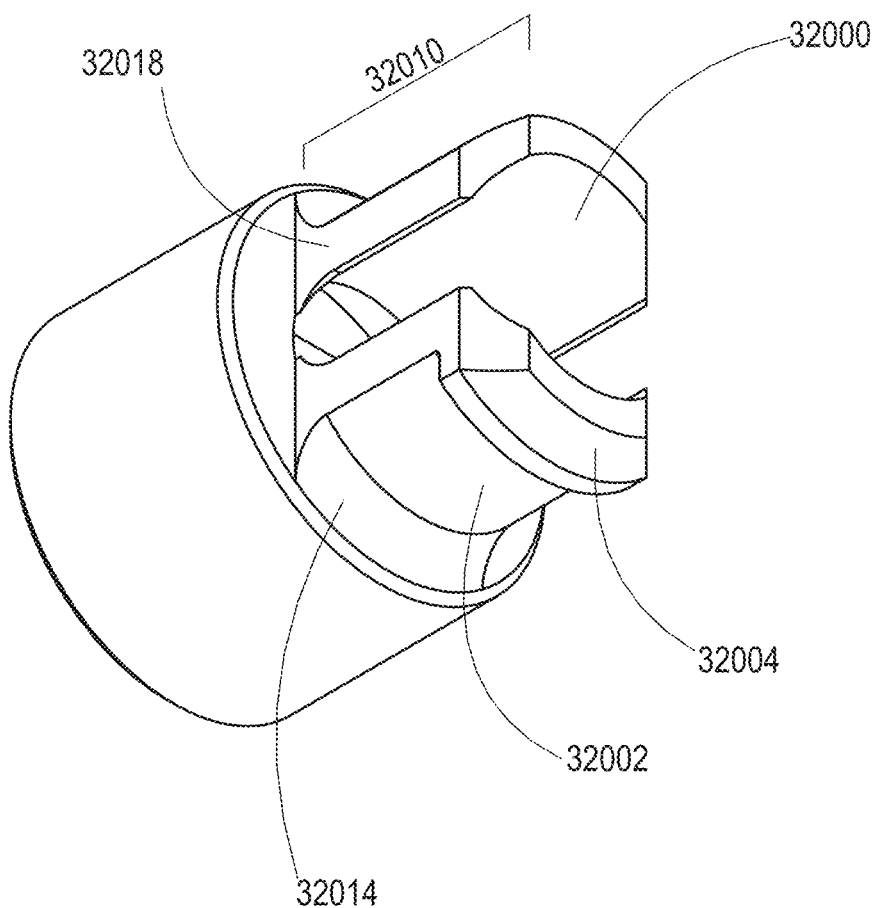
FIGS. 32A-E are views of a link in accordance with FIG. 28 from various directions and cross sections, according to some embodiments of the invention.
Figure 32B:
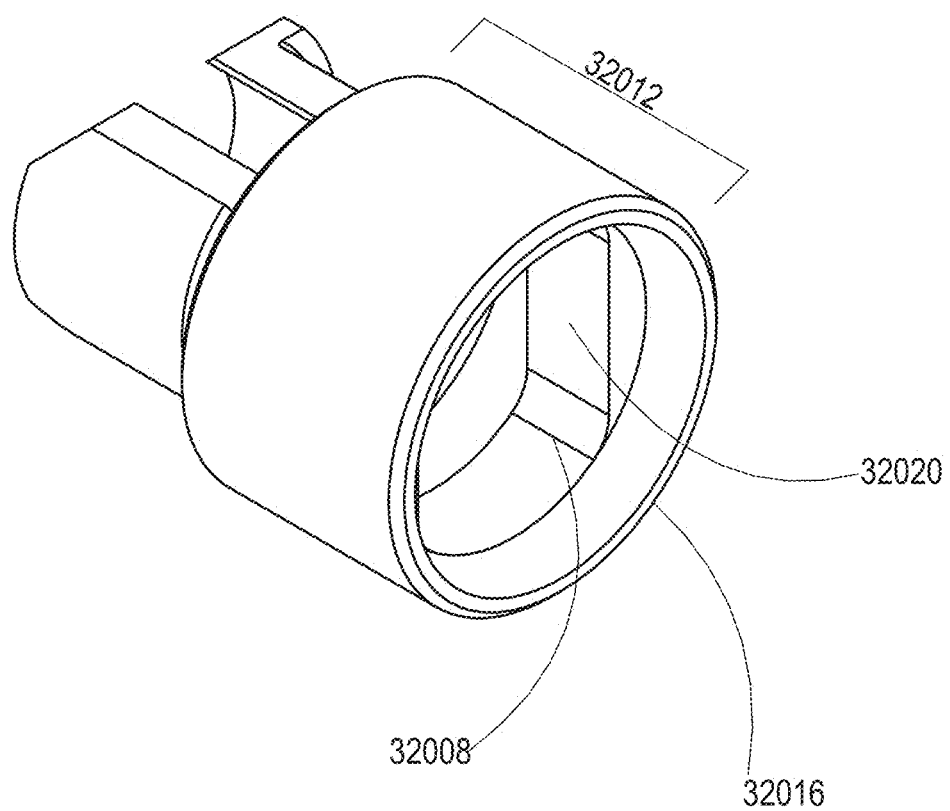
Figure 32C:
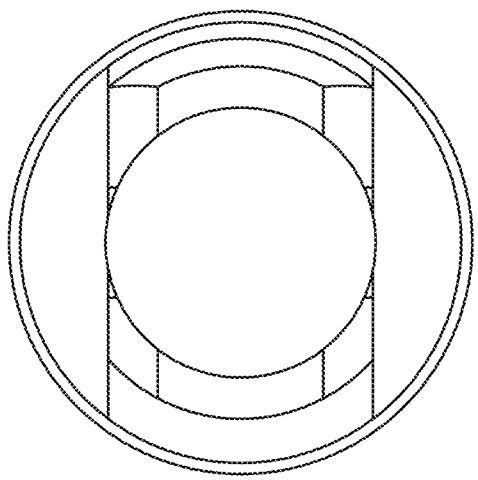
Figure 32D:
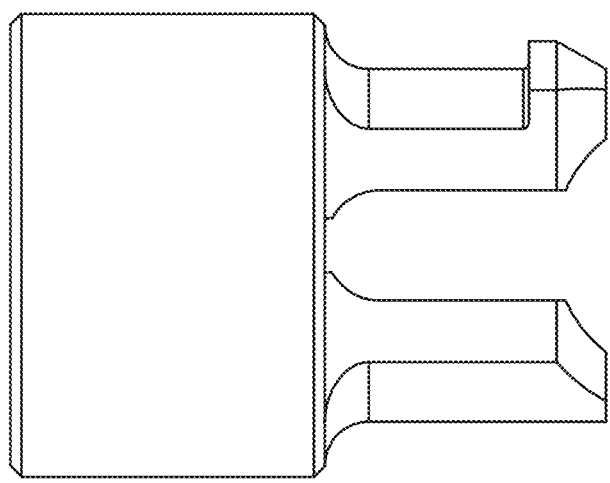
Figure 32E:
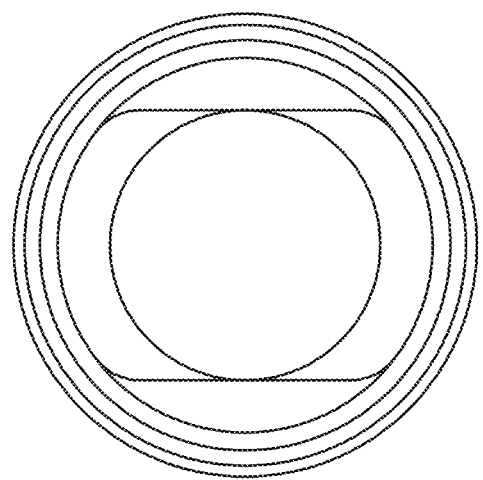

FIGS. 31A-B illustrate advancement of a flexible bone tool in accordance with FIG. 28 into a bone, according to some embodiments of the invention. FIGS. 31A-B generally correspond to the described above in FIGS. 5A-B and the description of corresponding parts will not be repeated.

FIGS. 32A-E are views of a link in accordance with FIG. 28 from various directions and cross sections, according to some embodiments of the invention. FIGS. 32A-E generally correspond to the described above in FIGS. 6A-E and the description of corresponding parts will not be repeated. It is noted that in this exemplary configuration, only one of the tooth like extensions comprises a radial protrusion 32004.

Figure 33A:
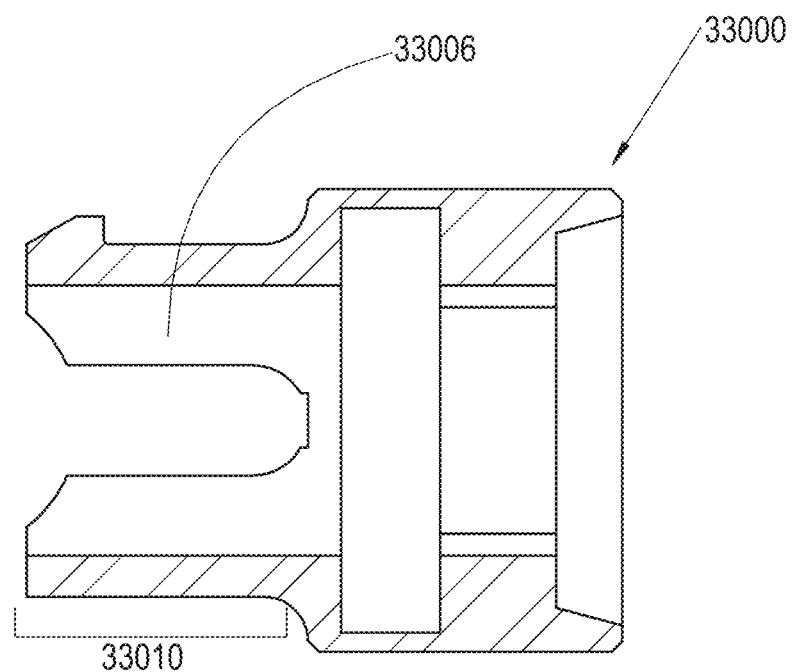
FIGS. 33A-C are cross section views of a link (33A), a receiving subsequent link (33B), rotationally oriented relative to the link of 33A, and the links coupled to each other (33C), according to some embodiments of the invention.
Figure 33B:
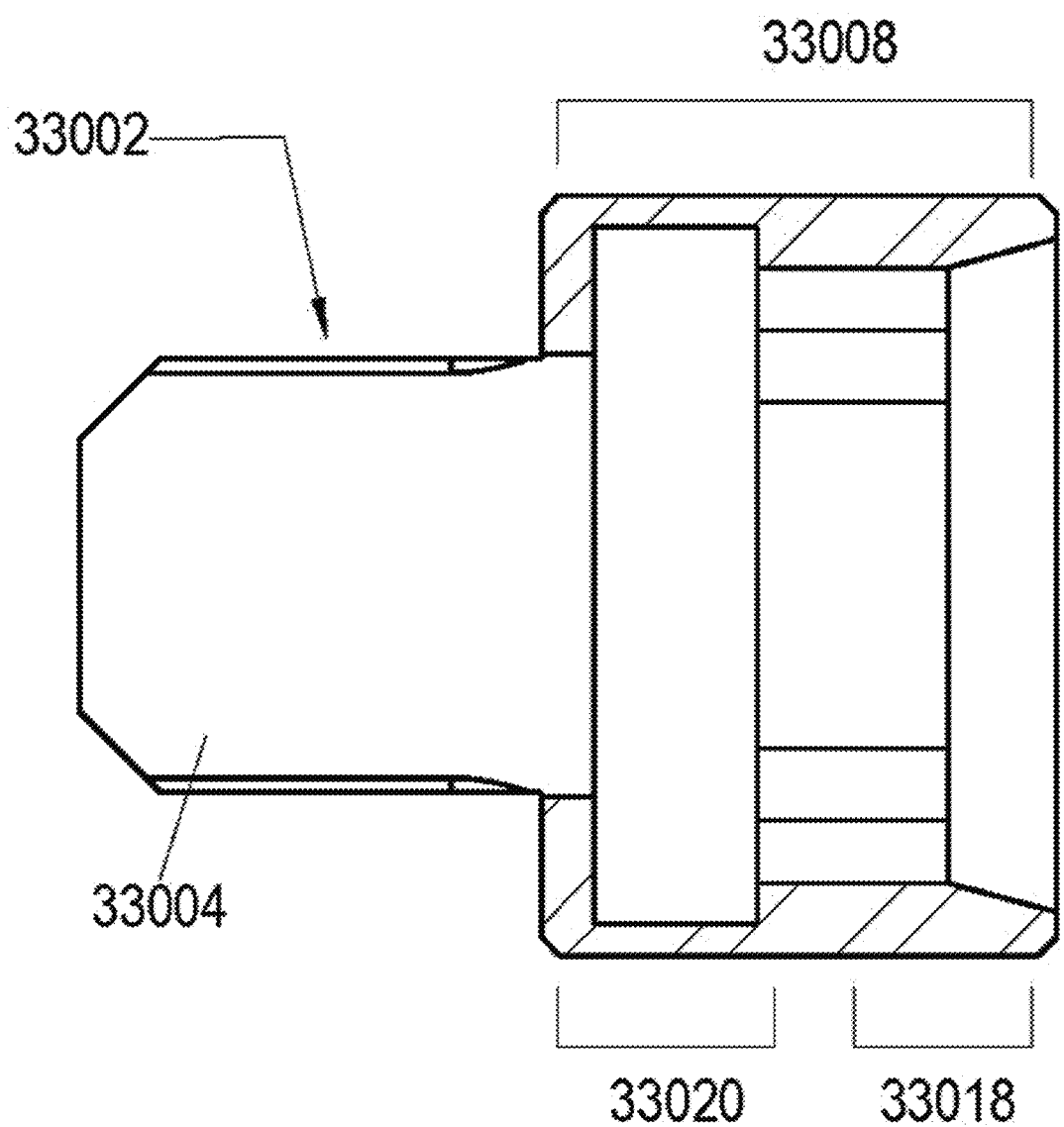
Figure 33C:
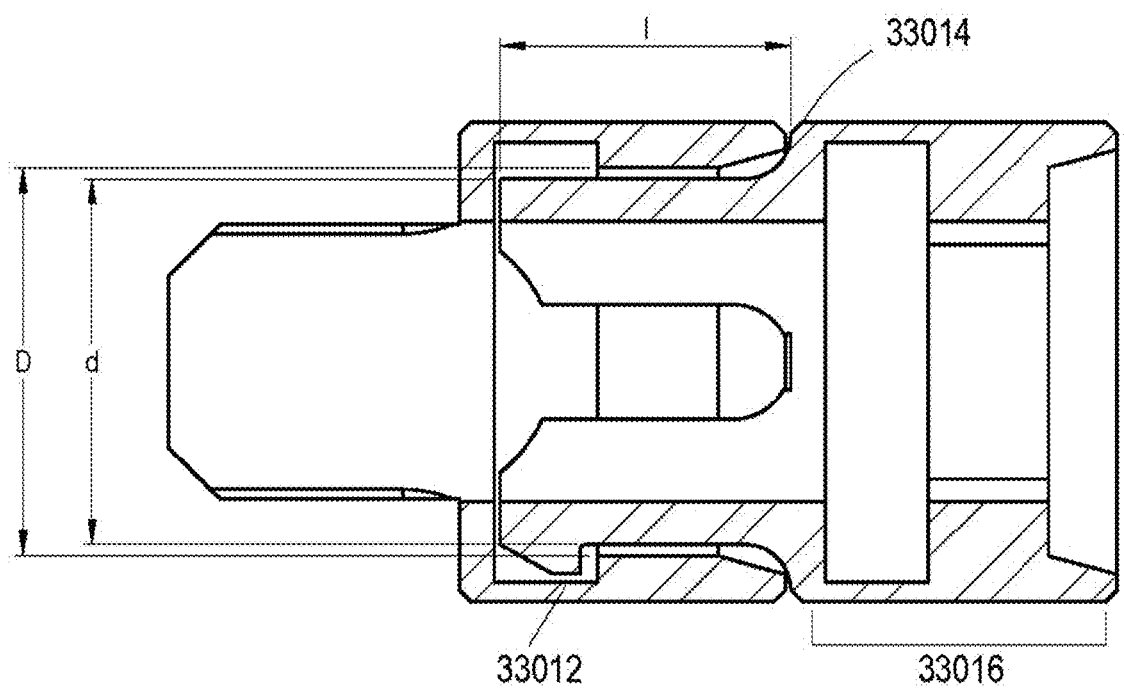
Figure 34B:
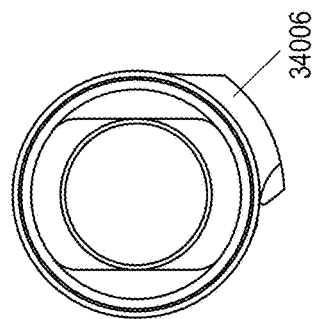
FIGS. 34A-G illustrate a distal cutting head configured to engage a flexible bone tool in accordance with FIG. 28, according to some embodiments of the invention.
Figure 34D:
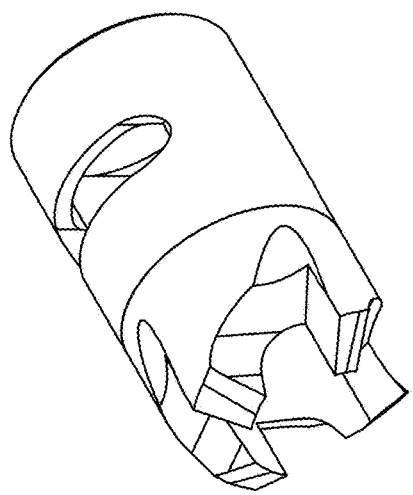
Figure 34A:
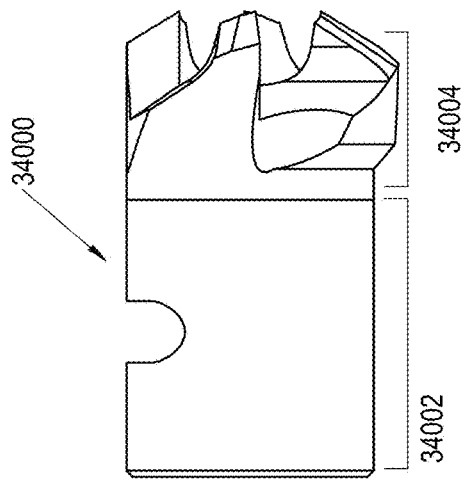
Figure 34C:
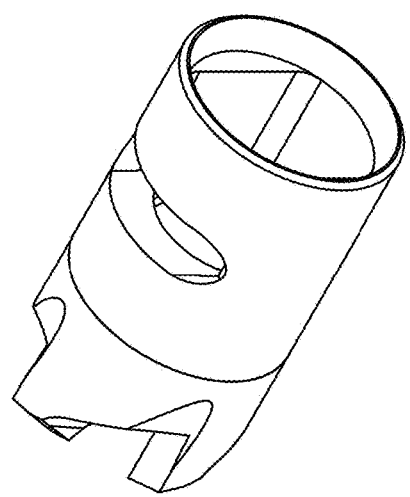
Figure 34F:
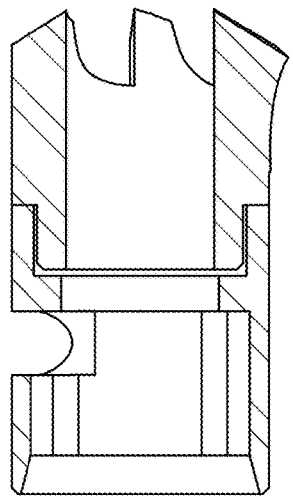
Figure 34E:
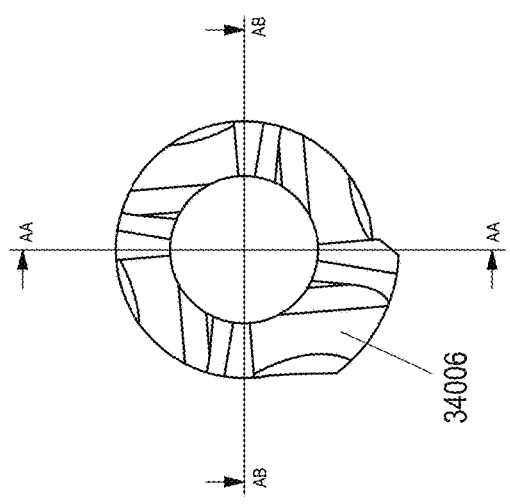
Figure 34G:
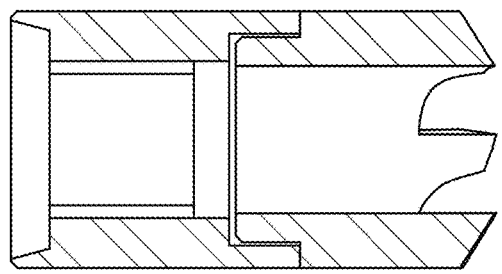

FIGS. 33A-C are cross section views of a link (33A), a receiving subsequent link (33B), rotationally oriented relative to the link of 33A, and the links coupled to each other (33C), according to some embodiments of the invention. FIGS. 33A-C generally correspond to the described above in FIGS. 7A-C and the description of corresponding parts will not be repeated.

FIGS. 34A-G illustrate a distal cutting head configured to engage a flexible bone tool in accordance with FIG. 28, according to some embodiments of the invention.

FIGS. 34A-G generally correspond to the described above in FIGS. 8A-G and the description of corresponding parts will not be repeated.

FIGS. 35A-E illustrate another configuration of a distal cutting head configured to engage a flexible bone tool in accordance with FIG. 28, according to some embodiments of the invention. FIGS. 35A-E generally correspond to the described above in FIGS. 9A-E and the description of corresponding parts will not be repeated.

Figure 36:
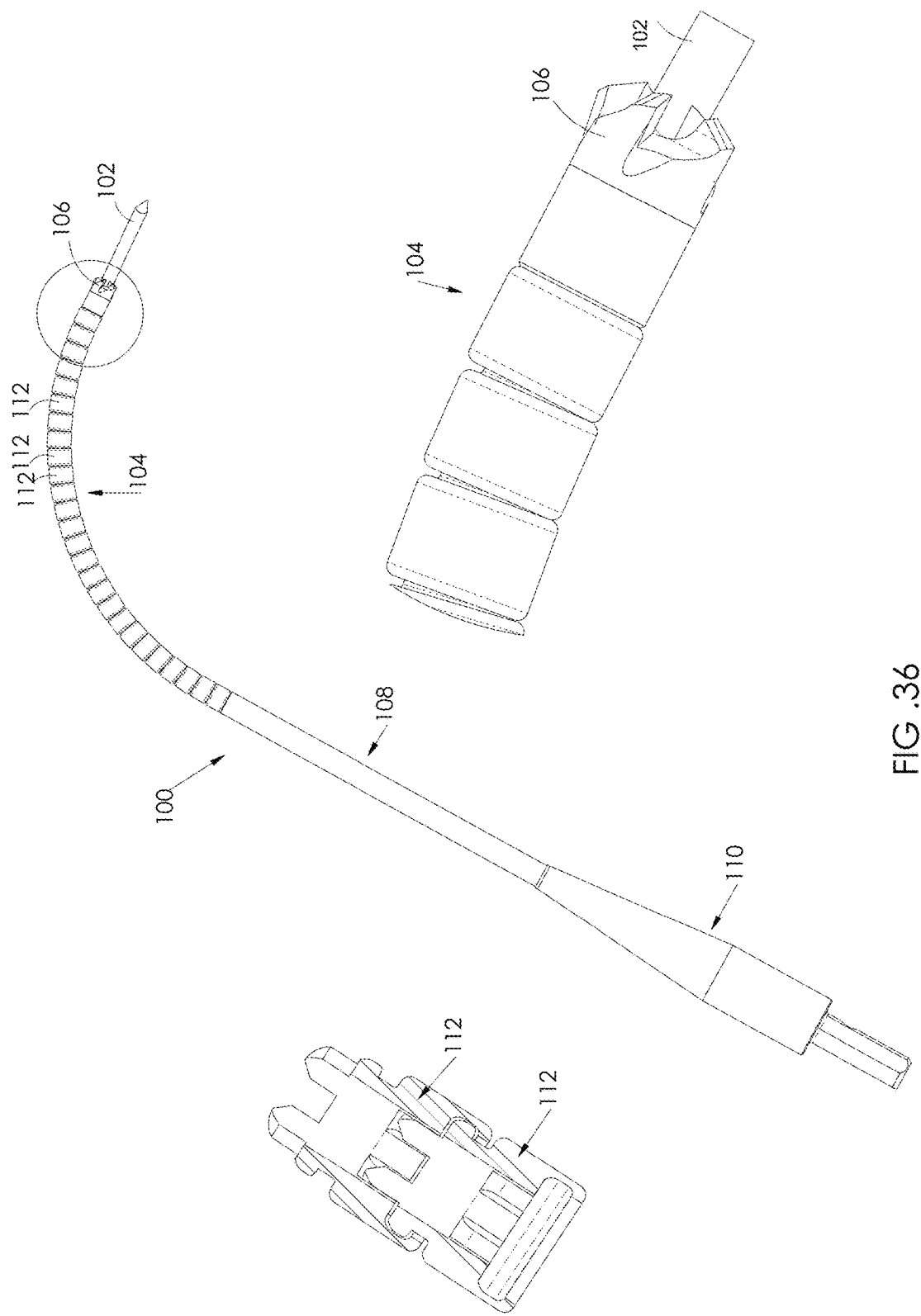
FIG. 36 is a simplified pictorial illustration of a flexible reamer constructed and operative in accordance with an embodiment of the present invention.

Reference is now made to FIG. 36, which is a simplified pictorial illustration of a flexible reamer 100 constructed and operative in accordance with an embodiment of the present invention.

In some embodiments, for example as shown in FIG. 36, the flexible reamer 100 is preferably made of a biocompatible plastic material, such as for example polycarbonate or isoplast and is disposable following a single surgical procedure.

In some embodiments, for example as shown in FIG. 36, the flexible reamer 100 is disposed over a guide pin 102. Optionally, the guide pin 102 is made of a substantially flexible material, such as nitinol. Optionally, the flexible reamer 100 is cannulated in order to allow its positioning over the guide pin 102.

The flexible reamer 100 in an exemplary embodiment of the present invention is comprised of a distal portion 104 with a drilling distal end 106, an intermediate portion 108 and a proximal holding portion 110.

In some embodiments, the distal portion 104 is comprised of a plurality of individual links 112, which are connected each to another in an articulated manner, which allows force transfer from one link to another in a direction corresponding to the direction of the guide pin 102.

In some embodiments, the links 112 are inseparably interconnected each with another in order to form a unitary structure.

In some embodiments, the interconnection between the links 112 and the enablement of force transfer between the plurality of links 112 is provided due to the structure of each link 112, as is further described in detail.

Figure 37B:
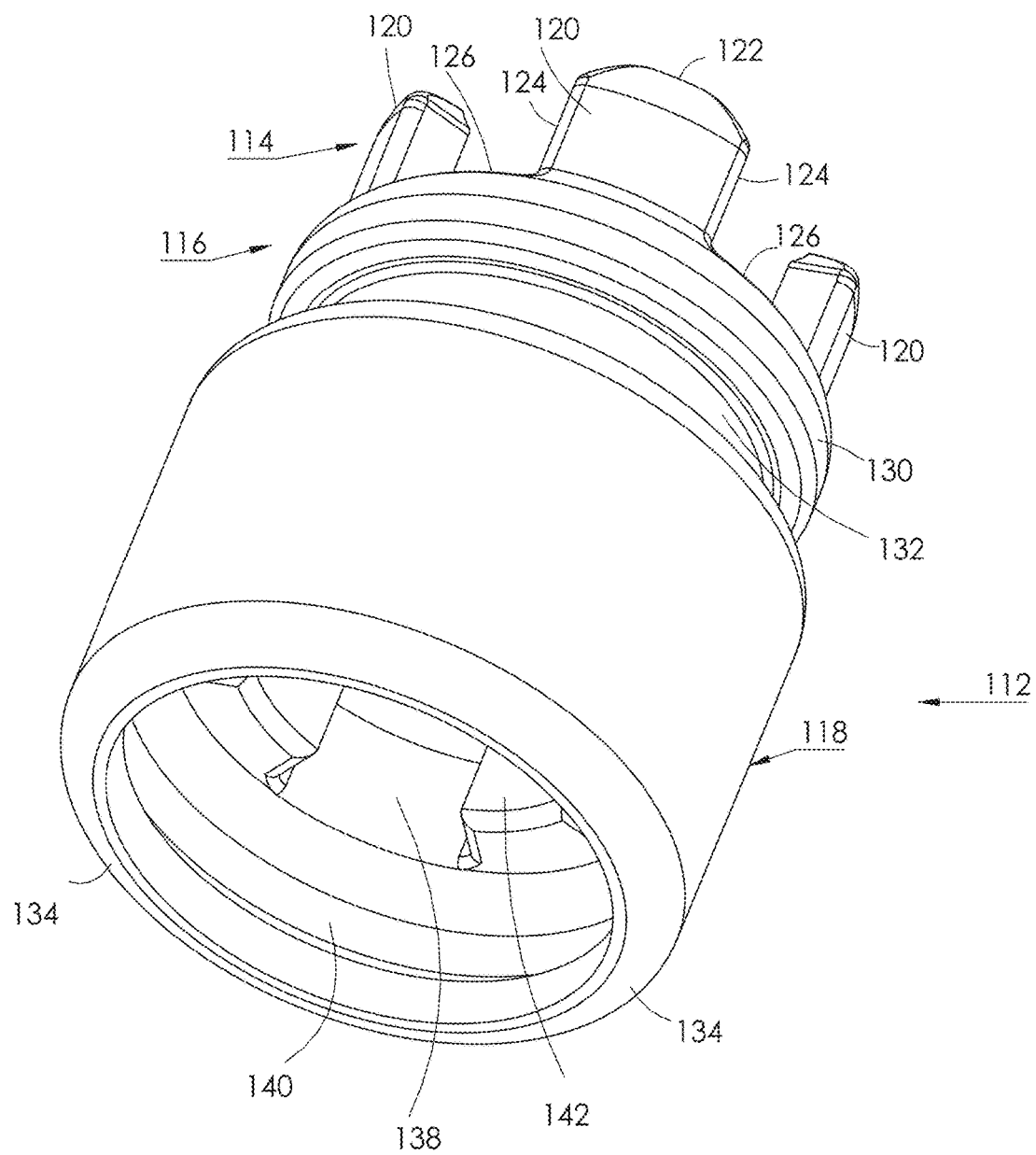
Figures 38A, 38B, 38C:
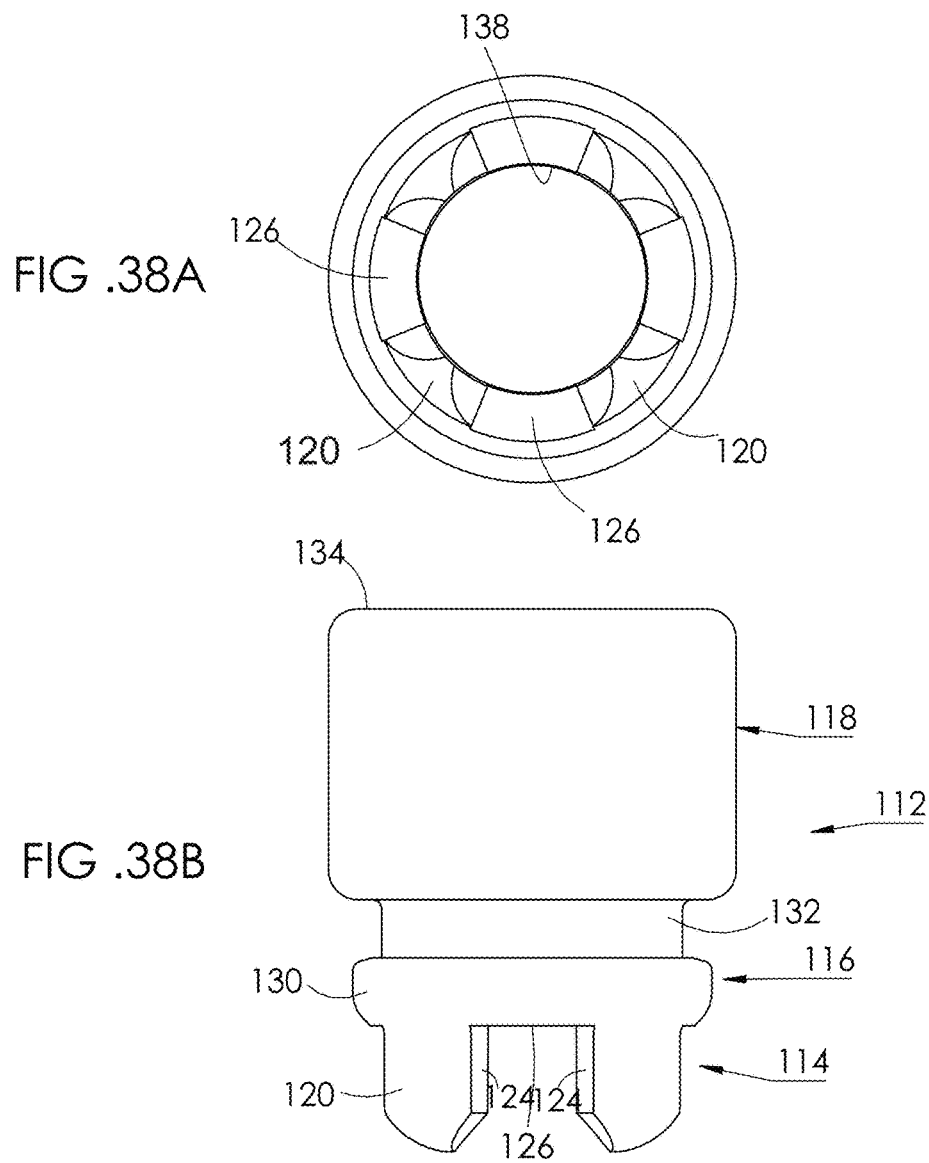
FIGS. 38A-C are respective simplified side, bottom and top view illustrations of the single link shown in FIGS. 2A1-A2-A3 and 2B.

Reference is now made to FIGS. 37A & 37B, which are simplified pictorial illustrations of a single link 112 of the flexible reamer 100 of FIG. 1, shown from the distal end and from the proximal end respectively. Reference is additionally made to FIGS. 38A-C, which are respective simplified side, bottom and top view illustrations of the single link shown in FIGS. 37A-B and to FIGS. 39A & 39B, which are simplified orthogonal section views of the single link shown in FIGS. 37A & 37B, the section views are taken along lines A-A, B-B respectively on FIG. 37A.

It is seen in FIGS. 37A-39B that the single link 112, in some embodiments, is a hollow generally cylindrical element, which is integrally formed of a plastic material and has a distal portion 114, an intermediate portion 116 and a proximal portion 118. The distal portion 114 preferably includes a plurality of gear-like teeth 120 (also referred to in some embodiments described herein as "tooth-like extensions"), which are, in some embodiments, evenly disposed along the circumference of the link 112 and extend distally from the intermediate portion 116 to a distal end 122.

In some embodiments, each gear-like tooth 120 has two mutually facing surfaces 124, which extend distally nearly to the distal end 122.

In some embodiments, the gear-like teeth 120 define alternating recesses 126 between each of the teeth 120 along the circumference of the link 112.

In some embodiments, the longitudinal extent of surfaces 124 provides for enhanced force transfer.

In some embodiments, the intermediate portion 116 includes a radially outwardly extending flange 130. The outer diameter of the flange 130 is generally greater than a diameter of an imaginary cylinder formed by the gear-like teeth 120. The intermediate portion 116 further includes an annular portion 132, positioned proximally to the flange 130 and having an external diameter substantially equal to the diameter of an imaginary cylinder formed by the gear-like teeth 120.

In some embodiments, the flange 130 and the annular portion 132 provide for inseparable snap-fit interconnection between two adjacent links 112. Optionally, the connection between adjacent links can be separated by applying a strong pull out force, for example when adjusting a length of the tool outside the body.

In some embodiments, the proximal portion 118 is generally cylindrical, and its outer diameter is preferably greater than the diameter of flange 130. Optionally, the proximal portion 118 extends proximally from the annular portion 132 to a proximal end 134.

In some embodiments, an inner surface 138 is defined jointly by the distal portion 114, intermediate portion 116 and proximal portion 118. An undercut 140 is formed on the inner surface 138 of the link 112.

In some embodiments, the undercut 140 is provided for enabling inseparable interconnection between two links 112, by receiving a flange 130 of the subsequent link 112 therein.

Figure 39A:
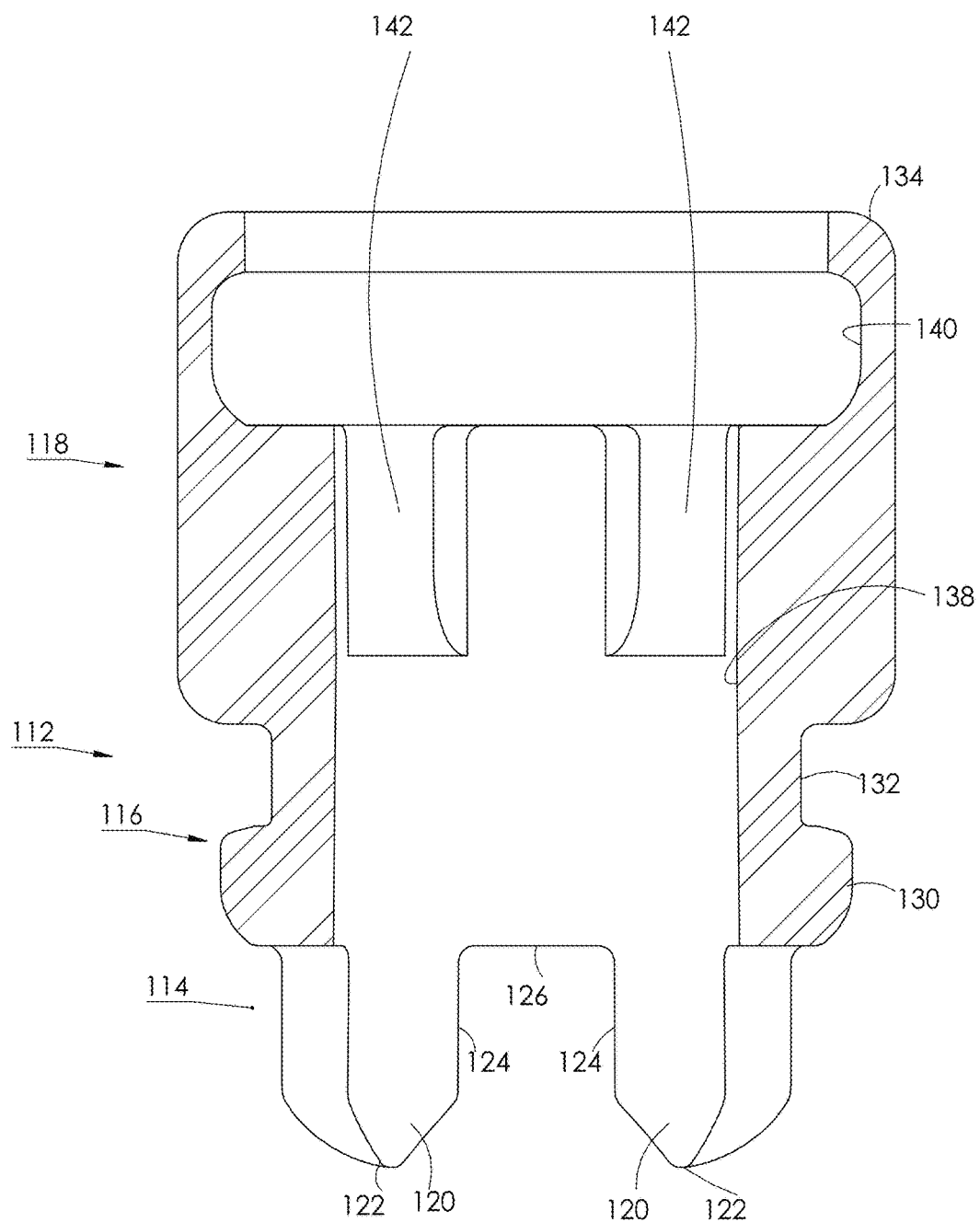
FIGS. 39A-B are simplified orthogonal section views of the single link shown in FIGS. 37A-37B, the section views are taken along lines A-A, B-B respectively on FIG. 37A.
Figure 39B:
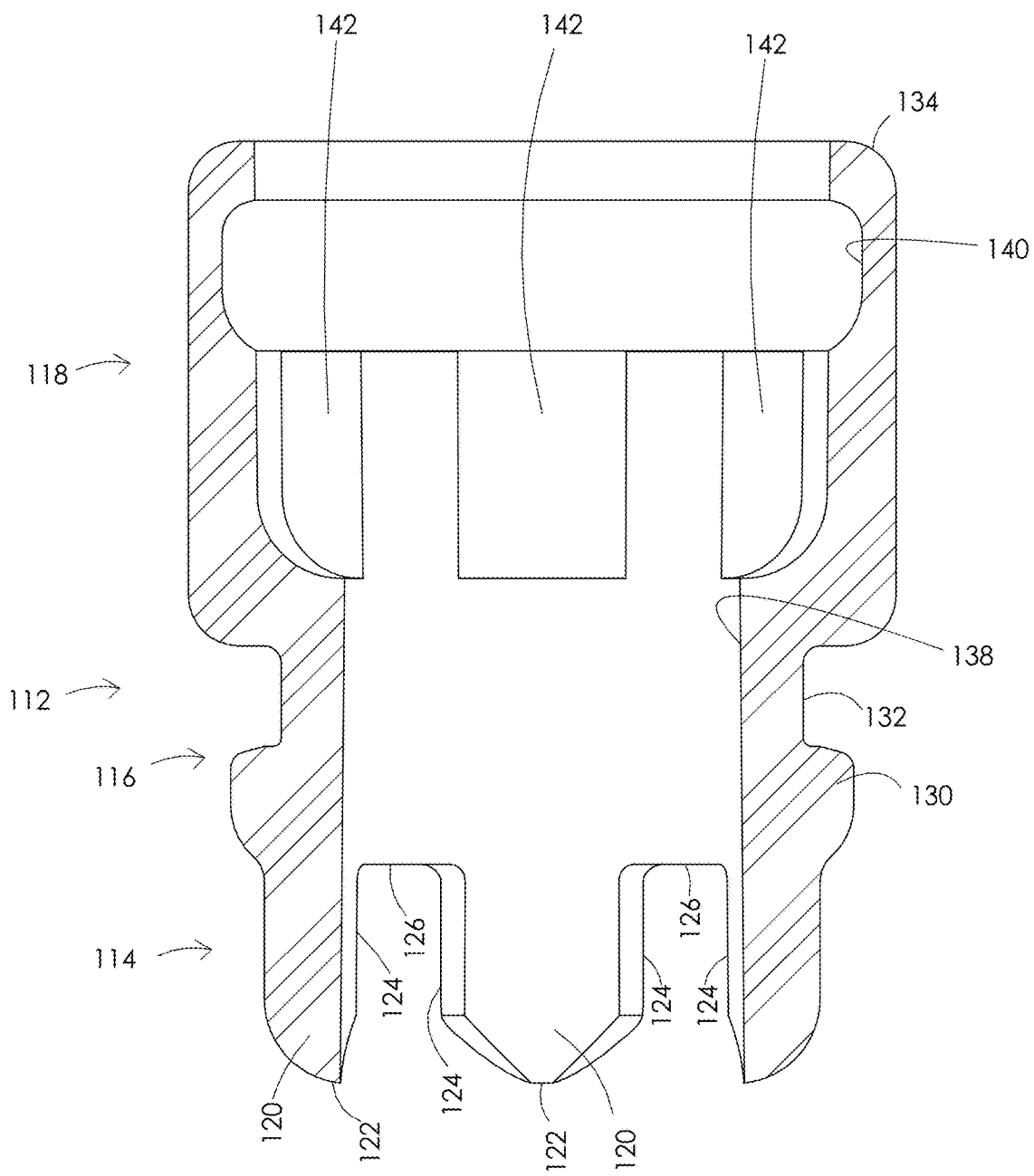

It is further seen specifically in FIGS. 37B, 39A & 39B that in some embodiments, a plurality of corresponding gear-like teeth 142 are preferably evenly disposed along the inner circumference of the link 112 and extend radially inwardly from the inner surface 138 and distally from the undercut 140.

In some embodiments, the corresponding gear-like teeth 142 are provided for meshing with the gear-like teeth 120 on the subsequent link 112 for transferring force between the two subsequent links 112 and providing for articulated movement therebetween.

Figure 40:
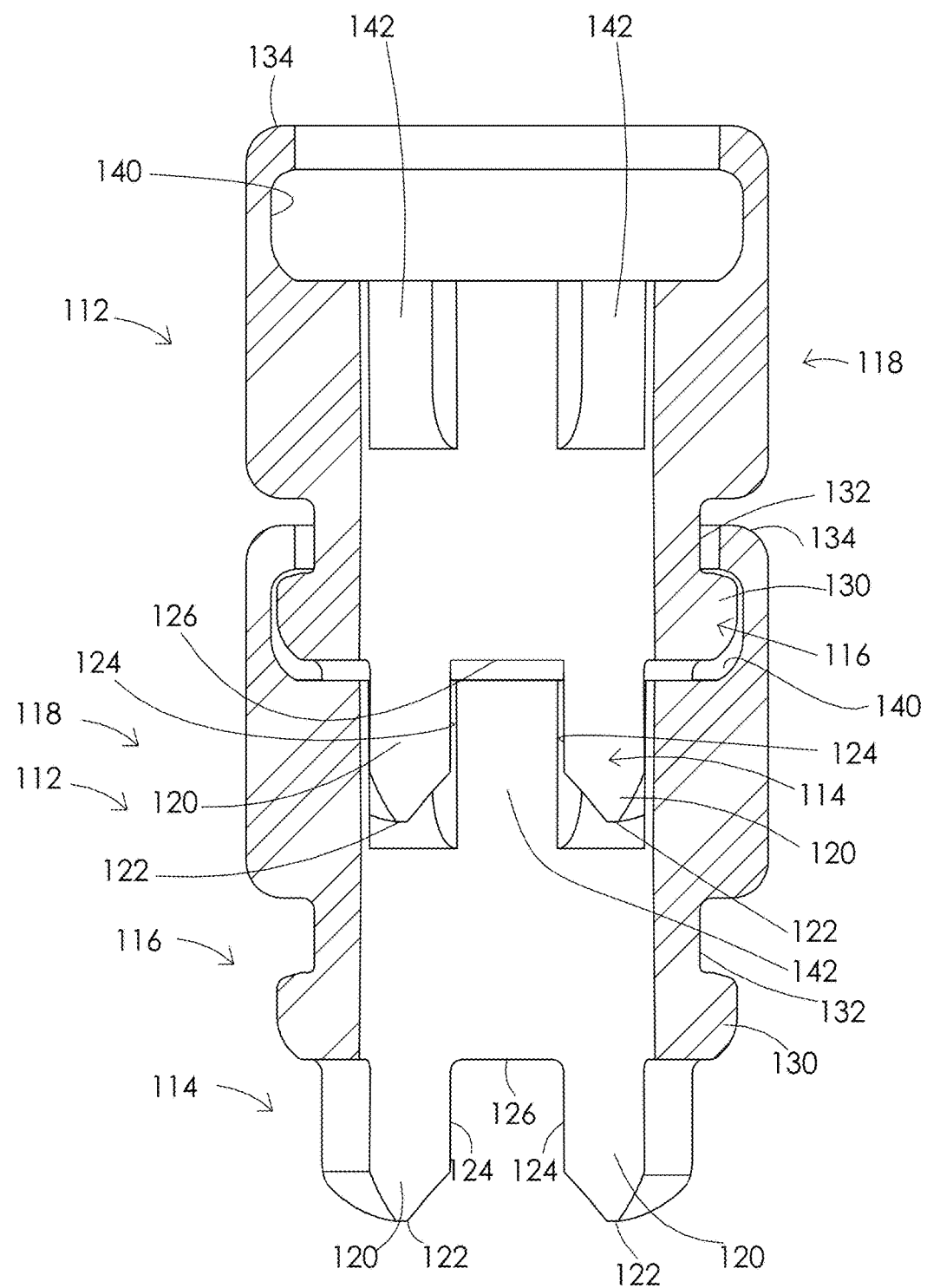
FIG. 40 is a simplified section view of interconnected two links of FIGS. 37A & 37B.

Reference is now made to FIG. 40, which is a simplified section view of interconnected two links 112 of FIGS. 37A & 37B.

It is specifically seen in FIG. 40 that in some embodiments, when two subsequent links 112 are interconnected, the gear-like teeth 142 of a distal link are received within the recesses 126 of a proximal link 112 and the flange 130 of the proximal link 112 is fixedly received within the undercut 140 of the distal link 112 and thus an array of links 112 can be created by interconnecting two subsequent links 112, which are inseparable one from another, enable enhanced force transfer one from another and provide for articulate movement of the distal portion 104 as a unitary structure.

Figure 41:
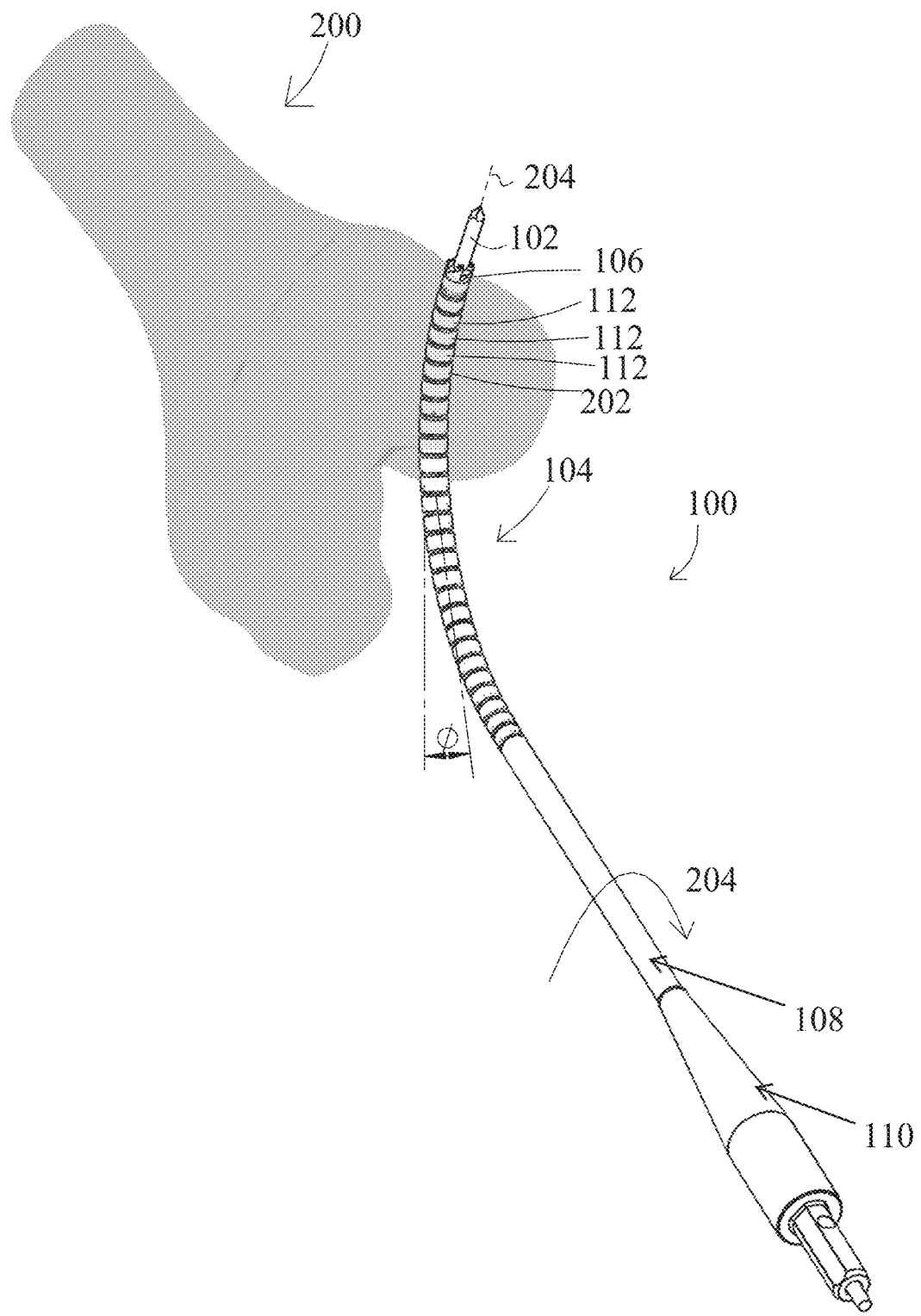
FIG. 41 is a simplified pictorial illustration of the flexible reamer of FIG. 36 inserted into the femoral bone.

FIG. 41 is a simplified pictorial illustration of the flexible reamer 100 of FIG. 36 inserted into a femoral bone 200 in order to create a greater diameter femoral tunnel 202 over a pre-drilled femoral bore.

It is seen in FIG. 41 that the guide pin 102 is inserted through a pre-drilled femoral bore and a flexible reamer 100 is slidable over the guide pin 102 in order to drill a femoral tunnel 202 of a greater diameter. Once a rotational movement indicated by arrow 204 is exerted on the proximal portion 110, it is transferred to the intermediate portion 108 and the distal portion 104.

Due to the flexibility of the distal portion 104 composed of an array of links 112, as described in detail above, the distal end 106 engages the femoral bone 200 at an angle Phi, which is preferably an acute angle relative the longitudinal axis of the formed femoral tunnel 202.

It is appreciated that in another embodiment of the present invention, the flexible reamer 100 may be used in order to provide a radial tunnel, while the guide pin 102 defines an arc and the flexible reamer 100 is advanced within the femoral bone 200 along this arc.

It is further appreciated that proximal portion 110 may be formed with a recess, which provides for relief of torsion strains exerted on it by a power toll while providing rotational movement in a direction indicated by arrow 204.

In some embodiments, a fulcrum point of the distal portion 104 is formed at the most-proximal link 112 in order to provide for integrity of the distal portion 104 during the drilling procedure. Particularly, the weakest connection can be provided between the most-proximal link 112 and the link that is positioned distally adjacent to it, such that in case that the flexible reamer 100 is damaged, it will break at the most proximal point of the links array in order to enable safe retrieval of the flexible reamer 100 as an integral unit towards outside of the patient's body.

Figure 42:
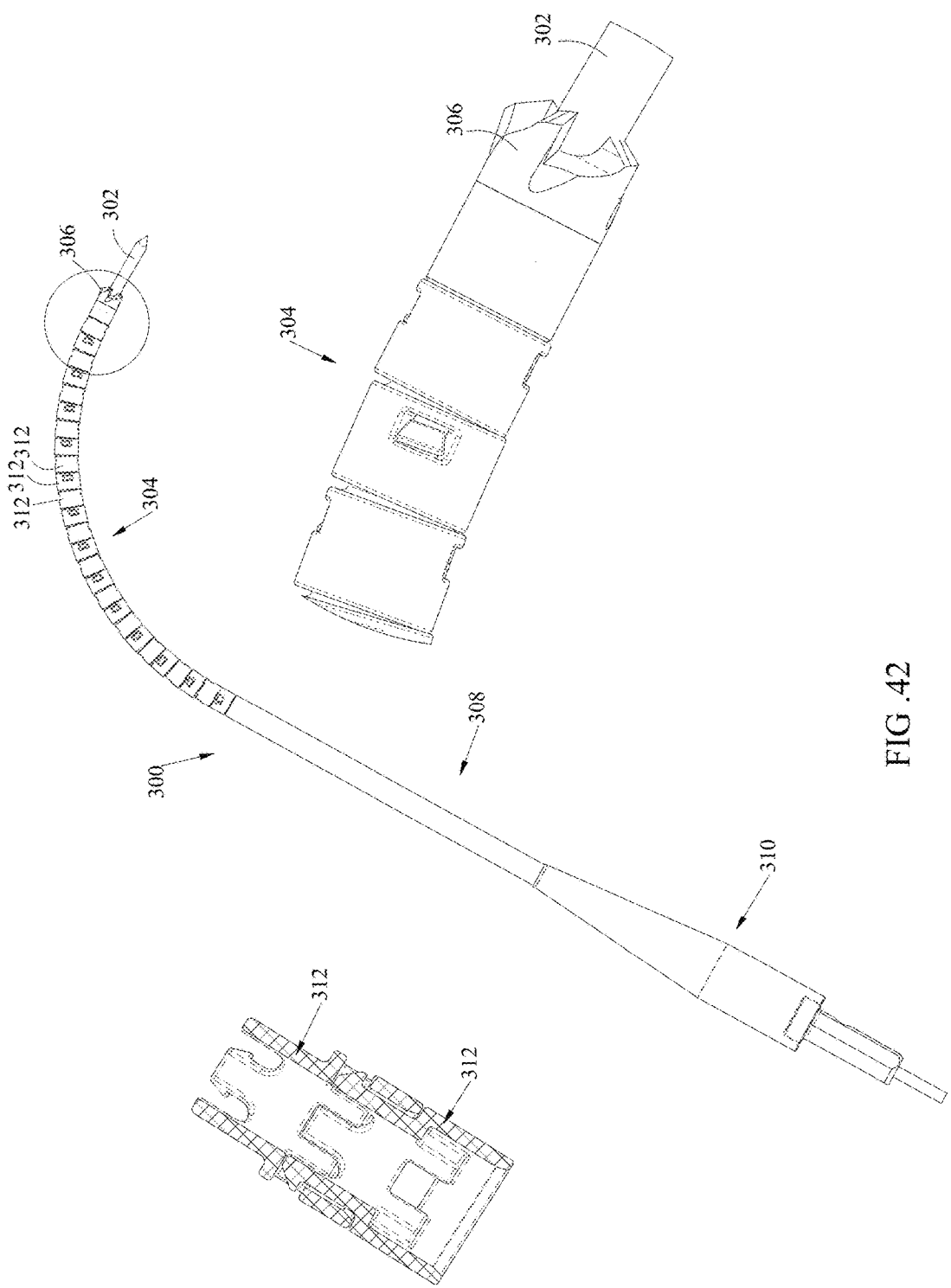
FIG. 42 is a simplified pictorial illustration of a flexible reamer constructed and operative in accordance with another embodiment of the present invention.

Reference is now made to FIG. 42, which is a simplified pictorial illustration of a flexible reamer 300 constructed and operative in accordance with an embodiment of the present invention.

The flexible reamer 300 that is seen in FIG. 42 is preferably made of a biocompatible plastic material, such as for example polycarbonate or isoplast and is disposable following a single surgical procedure.

It is seen in FIG. 42 that in some embodiments the flexible reamer 300 is disposed over a guide pin 302. The guide pin 302 is made of a substantially flexible material, such as nitinol. The flexible reamer 300 is cannulated in order to allow its positioning over the guide pin 302.

The flexible reamer 300 in one embodiment of the present invention is comprised of a distal portion 304 with a drilling distal end 306, an intermediate portion 308 and a proximal holding portion 310.

In some embodiments, the distal portion 304 is comprised of a plurality of individual links 312, which are connected each to another in an articulated manner, which allows force transfer from one link to another in a direction corresponding to the direction of the guide pin 302.

In some embodiments, the links 312 are inseparably interconnected each with another in order to form a unitary structure. Optionally, the connection between adjacent links can be separated by applying a strong pull out force, for example when adjusting a length of the tool outside the body.

In some embodiments, the interconnection between the links 312 and the enablement of force transfer between the plurality of links 312 is provided due to the structure of each link 312, as is further described in detail.

Figure 44C:
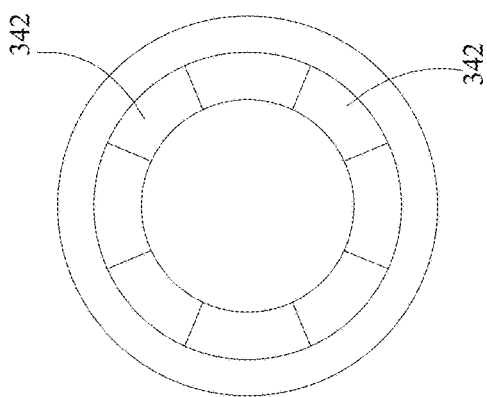
FIGS. 44A-C are respective simplified side, bottom and top view illustrations of the single link shown in FIGS. 43A & 43B.
Figure 44B:
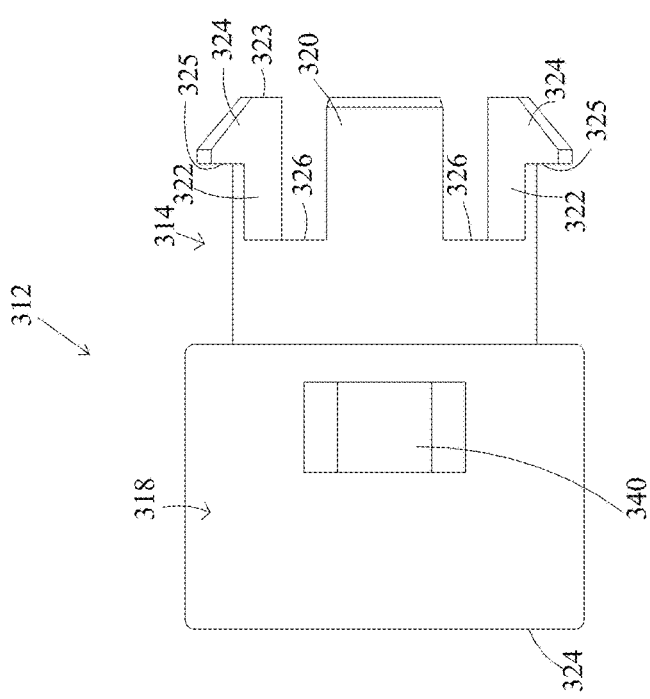
Figure 44A:
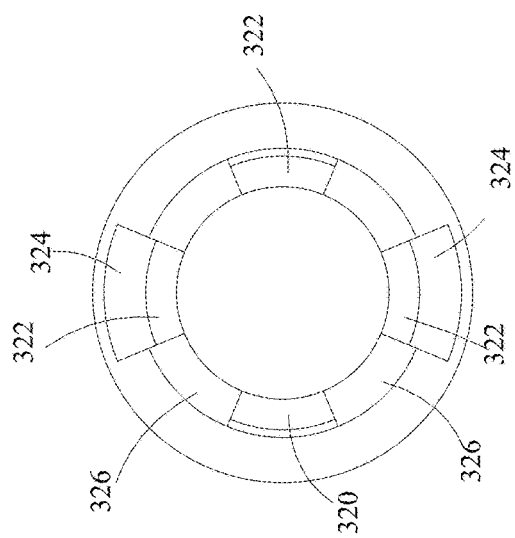

Reference is now made to FIGS. 43A & 43B, which are simplified pictorial illustrations of a single link 312 of the flexible reamer 300 of FIG. 42, shown from the distal end and from the proximal end respectively. Reference is additionally made to FIGS. 44A-44C, which are respective simplified side, bottom and top view illustrations of the single link shown in FIGS. 43A-43B and to FIGS. 45A & 45B, which are simplified orthogonal section views of the single link shown in FIGS. 43 & 43B, the section views are taken along lines A-A, B-B respectively on FIG. 43A.

It is seen in FIGS. 43A-45B that in some embodiments, the single link 312 is a hollow generally cylindrical element, which is integrally formed of a plastic material and has a distal portion 314 and a proximal portion 318. The distal portion 314 preferably includes a plurality of gear-like teeth 320 alternating with restraining teeth 322, the gear-like teeth 320 and the restraining teeth 322 are in some embodiments evenly disposed in an alternating manner along the circumference of the link 312 and extend distally from the proximal portion 318 to a distal end 323.

In some embodiments, each restraining tooth 322 has a radially outwardly extending protrusion 324 at the distal end 323, defining a proximally facing stopping shoulder 325 for interconnection with a subsequent link 312.

In some embodiments, the gear-like teeth 320 and restraining teeth 322 define alternating recesses 326 between them along the circumference of the link 312.

In some embodiments, the restraining teeth 322 provide for inseparable snap-fit interconnection between two adjacent links 312. Optionally, the connection between adjacent links can be separated by applying a strong pull out force, for example when adjusting a length of the tool outside the body.

In some embodiments, the proximal portion 318 is generally cylindrical, and its outer diameter is preferably greater than the diameter of the distal portion 314. The proximal portion 318 extends proximally from the distal portion 314 to a proximal end 334.

In some embodiments, an inner surface 338 is defined jointly by the distal portion 314 and proximal portion 318. Typically two mutually facing apertures 340 are formed through the proximal portion 318 of the link 312.

It is a particular feature of an embodiment of the present invention that the apertures 340 are provided for enabling inseparable interconnection between two links 312, by receiving the restraining teeth 322 of the subsequent link 312 therein.

Figure 45A:
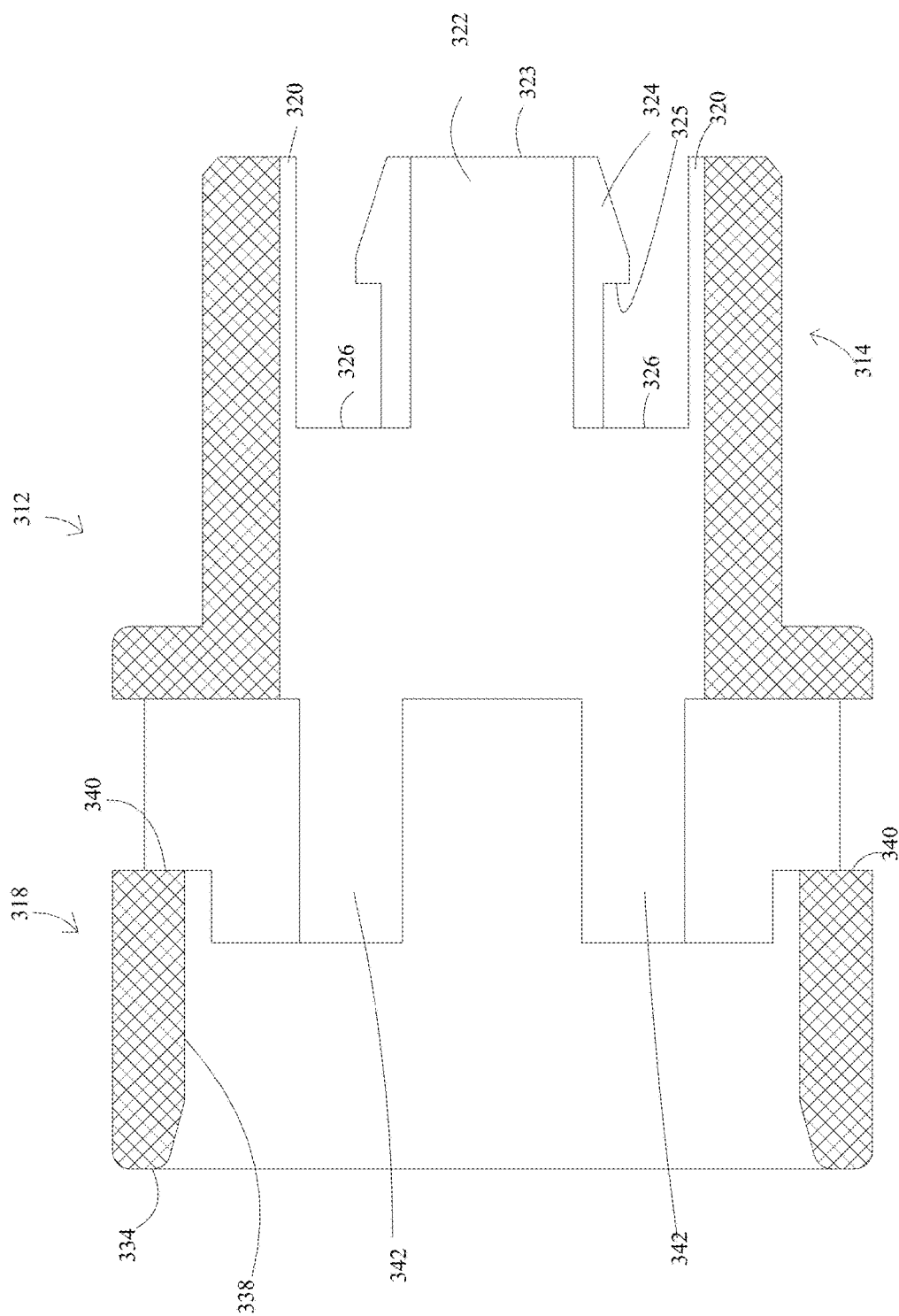
FIGS. 45A-B are simplified orthogonal section views of the single link shown in FIGS. 43A & 43B, the section views are taken along lines A-A, B-B respectively on FIG. 43A.
Figure 45B:
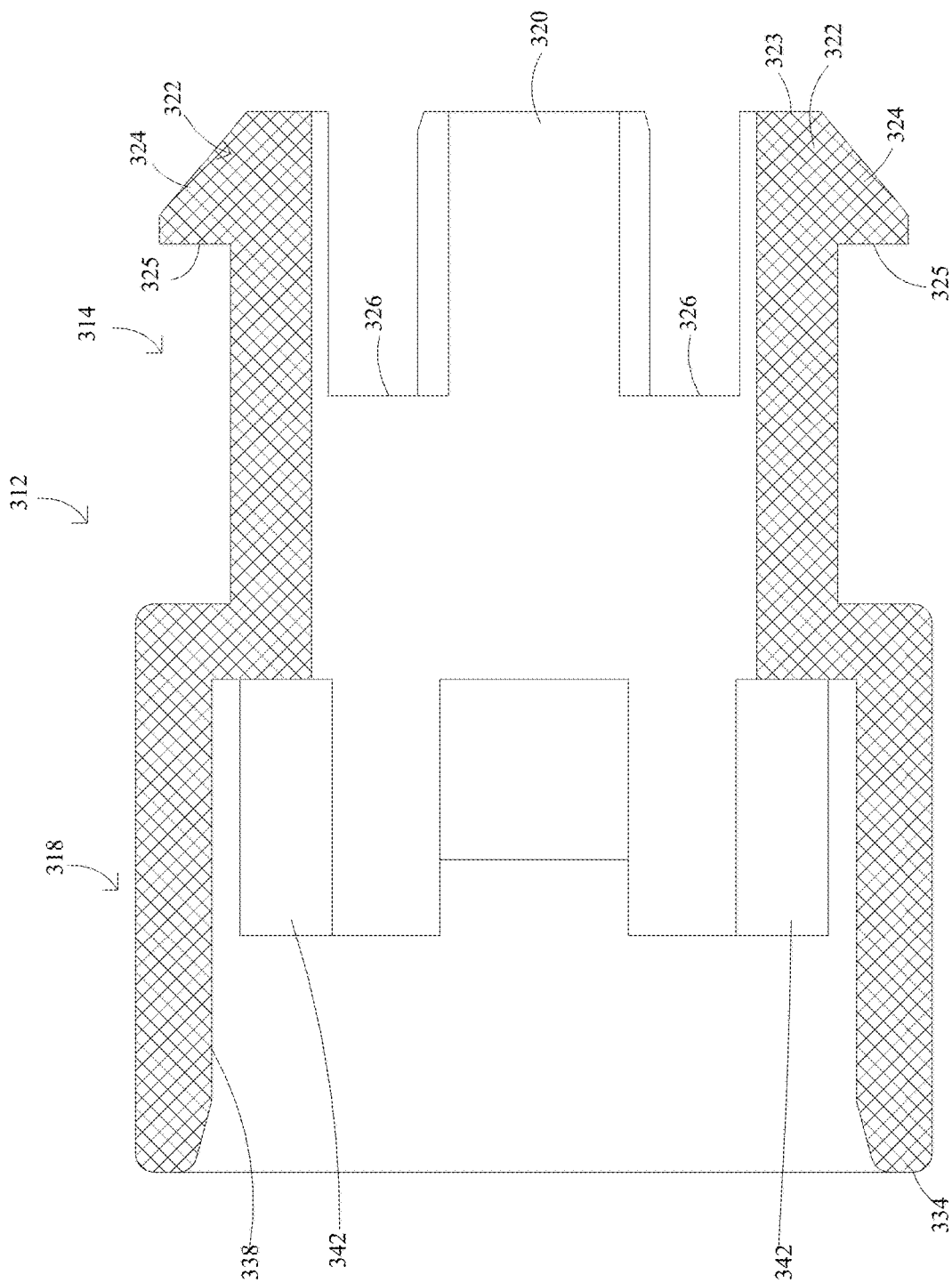

It is further seen specifically in FIGS. 8B, 45A & 45B that in some embodiments a plurality of corresponding gear-like teeth 342 are preferably evenly disposed along the inner circumference of the link 312 and extend radially inwardly from the inner surface 338 and preferably positioned distally from the proximal end 334.

In some embodiments, the corresponding gear-like teeth 342 are provided for meshing with the gear-like teeth 320 and the restraining teeth 322 on the subsequent link 312 for transferring force between the two subsequent links 312 and providing for articulated movement therebetween.

Reference is now made to FIG. 46, which is a simplified section view of interconnected two links 312 of FIGS. 43A & 43B.

It is specifically seen in FIG. 46 that in some embodiments, when two subsequent links 312 are interconnected, the gear-like teeth 342 of a distal link 312 are received within the recesses 326 of a proximal link 312 and the restraining teeth 322 of the proximal link 312 are fixedly received within the apertures 340 of the distal link 312 and thus an array of links 112 can be created by interconnecting two subsequent links 312, which are inseparable one from another, enable enhanced force transfer one from another and provide for articulate movement of the distal portion 304 as a unitary structure.

In some embodiments, when the links 312 are interconnected, the two apertures 340 on one link 312 are facing transversely to the apertures 340 of the subsequent link 312.

Figure 47:
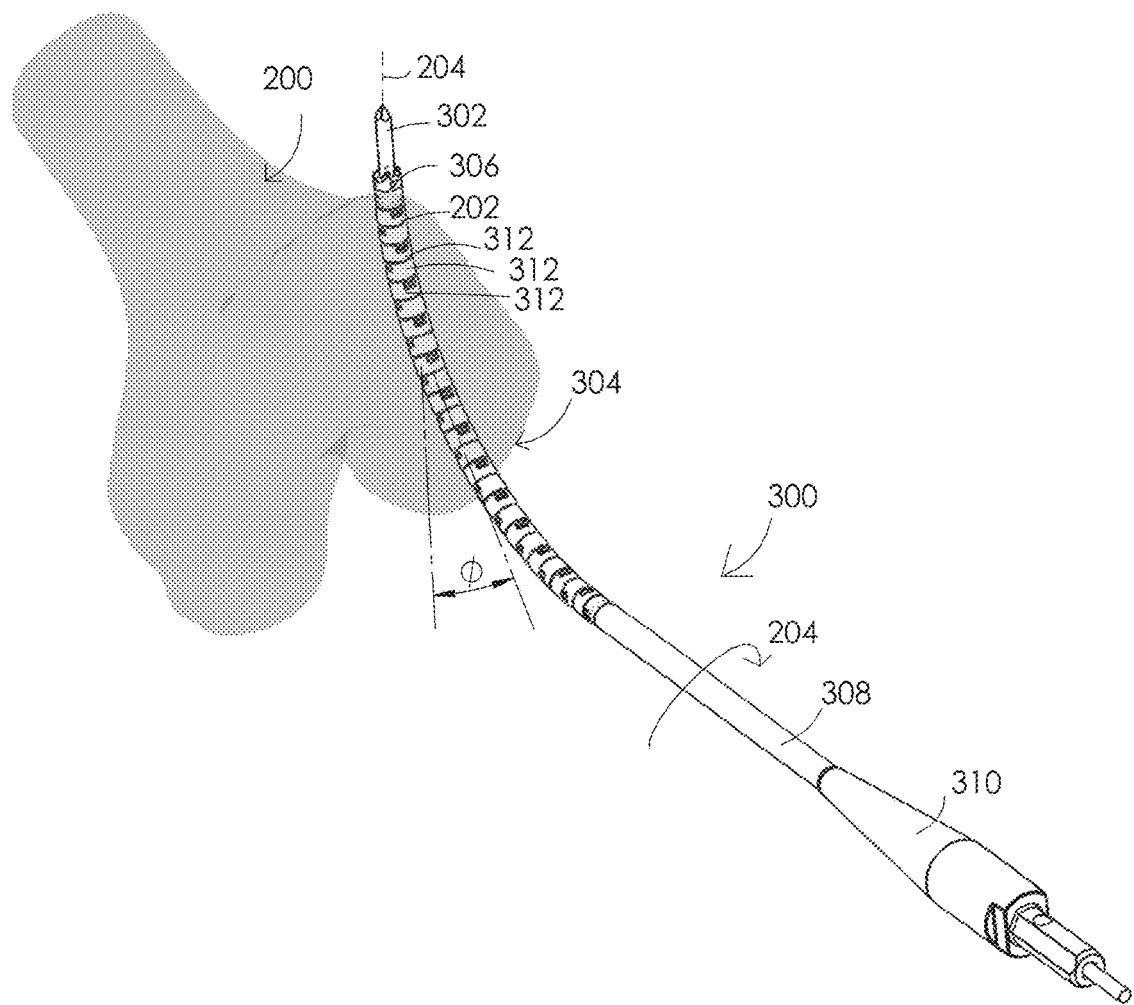
FIG. 47 is a simplified pictorial illustration of the flexible reamer of FIG. 42 inserted into the femoral bone.

FIG. 47 is a simplified pictorial illustration of the flexible reamer 300 of FIG. 42 inserted into a femoral bone 200 in order to create a femoral tunnel 202.

It is seen in FIG. 47 that the guide pin 302 is inserted through a pre-drilled femoral bore and a flexible reamer 300 is slidable over the guide pin 302. Optionally, once a rotational movement indicated by arrow 204 is exerted on the proximal portion 310, it is transferred to the intermediate portion 308 and the distal portion 304.

In some embodiments, due to the flexibility of the distal portion 304 composed of an array of links 312, as described in detail above with reference to FIG. 42-FIG. 46, the distal end 306 engages the femoral bone 200 at an angle Phi, which is preferably an acute angle relative the longitudinal axis of the formed femoral tunnel 202.

It is appreciated that in another embodiment of the present invention, the flexible reamer 300 may be used in order to provide a radial tunnel, while the guide pin 302 defines an arc and the flexible reamer 300 is advanced within the femoral bone 200 along this arc.

It is further appreciated that proximal portion 310 may be formed with a recess, which provides for relief of torsion strains exerted on it by a power toll while providing rotational movement in a direction indicated by arrow 204.

In some embodiments, a fulcrum point of the distal portion 304 is formed at the most-proximal link 312 in order to provide for integrity of the distal portion 304 during the drilling procedure. Particularly, the weakest connection can be provided between the most-proximal link 312 and the link that is positioned distally adjacent to it, such that in case that the flexible reamer 300 is damaged, it will break at the most proximal point of the links array in order to enable safe retrieval of the flexible reamer 300 as an integral unit towards outside of the patient's body.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A flexible bone tool comprising: a bone tissue removal element configured at a distal end of said tool; at least two links coupled proximally to said bone tissue removal element, said links connected to each other by a radial interference connection in which at least one radially outwards extending protrusion of a first link is received within a recess in an inner lumen of a subsequent link, wherein said first link and said subsequent link each comprise a receiving recess, wherein the recesses of both links have substantially the same design and are configured to be rotationally oriented relative to each other such that said receiving portion of said first link is configured at an angle to said receiving portion of said subsequent link.

2. The tool according to claim 1, wherein each of said links comprises an engaging portion and a receiving portion, said engaging portion positioned distally relative to said receiving portion.

3. The tool according to claim 2, wherein said receiving portion comprises an inner lumen open at a proximal end of said link and leading to said recess, said recess being large enough to receive said at least one protrusion without compressing it inwardly.

4. The tool according to claim 3, wherein said connection is a snap-fit connection in which said at least one radial protrusion is compressed inwardly by said inner lumen of said subsequent link and advanced distally until said protrusion is allowed to elastically snap into said recess, interlocking said first link and said subsequent link to each other while allowing bending of the links relative to each other.

5. The tool according to claim 2 , wherein said first link and said subsequent link comprise matching geometries comprise at least one surface shaped to interfere with axial rotation of the links relative to each other.

6. The tool according to claim 5, wherein said matching geometries comprise mutual flat faces that contact each other at least one part, wherein a first flat face is configured on said engaging portion of said first link, and a second flat face is configured within an inner lumen of said receiving portion of said subsequent link.

7. The tool according to claim 2, wherein said recess extends through an outer edge of said receiving portion and said protrusion is long enough to extend through said recess.

8. The tool according to claim 2, wherein said engaging portion comprises at least one tooth like extension extending in a distal direction, and wherein said protrusion extends radially outwards from said tooth like extension.

9. The tool according to claim 2, wherein said first link and said subsequent link comprise matching geometries suitable for transferring torque between said links at a magnitude sufficient for advancing said bone tissue removal element into a bone.

10. The tool according to claim 9, wherein said magnitude of torque ranges between 3N*cm to 30 N*cm.

11. The tool according to claim 2, wherein said recess does not extend beyond an outer edge of said receiving portion and said protrusion is internally received within said receiving portion.

12. The tool according to claim 1, wherein a volume of said at least one radial protrusion occupies no more than 95% of a volume of said recess.

13. The tool according to claim 1, wherein said links define a tubular body configured to bend into a bending radius of 30 mm or higher.

14. The tool according to claim 1, wherein said tool is cannulated, and wherein the cannulation is shaped and sized to allow delivery of said tool over a guide wire.

15. The tool according to claim 1, wherein said links interconnected to each other by a "click" type connection in which a sound indication is provided in the process of connecting the links.

16. The tool according to claim 1, wherein said angle is 90 degrees.

17. The tool according to claim 1, wherein said bone tissue removal element is shaped and sized to form a bore in said bone.

18. The tool according to claim 1, further comprising a holding section a proximal end of said tool, said holding section engageable by a user or a tool.

19. A flexible bone tool comprising: a bone tissue removal element configured at a distal end of said tool; at least two links coupled proximally to said bone tissue removal element, said links interconnected to each other by a "click" type connection in which a sound indication is provided in the process of connecting the links, wherein a first link and a subsequent link each comprise a receiving recess, wherein the recesses of both links have substantially the same design and are configured to be rotationally oriented relative to each other such that said receiving portion of said first link is configured at an angle to said receiving portion of said subsequent link.

* * * * *